US008105603B2

(12) United States Patent
Kelley et al.

(10) Patent No.: US 8,105,603 B2
(45) Date of Patent: Jan. 31, 2012

(54) POLYPEPTIDES THAT BIND APRIL

(75) Inventors: Robert F. Kelley, San Bruno, CA (US); Darshana Ramesh Patel, Burlingame, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 12/405,018

(22) Filed: Mar. 16, 2009

(65) Prior Publication Data
US 2009/0297504 A1    Dec. 3, 2009

Related U.S. Application Data

(62) Division of application No. 10/587,370, filed as application No. PCT/US2004/025247 on Aug. 4, 2004, now abandoned.

(60) Provisional application No. 60/540,271, filed on Jan. 29, 2004.

(51) Int. Cl.
A61K 39/00     (2006.01)
A61K 39/395    (2006.01)
A61K 38/00     (2006.01)
C07K 14/00     (2006.01)
C07H 21/04     (2006.01)
C12N 1/20      (2006.01)

(52) U.S. Cl. ............... 424/185.1; 424/192.1; 424/193.1; 514/1.1; 514/19.6; 530/350; 930/120; 536/23.4; 435/252.3

(58) Field of Classification Search .................. None
See application file for complete search history.

(56) References Cited

U.S. PATENT DOCUMENTS

| | | | |
|---|---|---|---|
| 4,816,567 A | 3/1989 | Cabilly et al. | |
| 5,428,130 A | 6/1995 | Capon et al. | |
| 5,716,805 A | 2/1998 | Srinivasan et al. | |
| 5,969,102 A | 10/1999 | Bram et al. | |
| 6,297,367 B1 | 10/2001 | Tribouley | |
| 6,316,222 B1 | 11/2001 | Bram et al. | |
| 6,403,770 B1 | 6/2002 | Yu et al. | |
| 6,475,987 B1 | 11/2002 | Shu | |
| 6,506,882 B2 | 1/2003 | Yu et al. | |
| 6,509,170 B1 | 1/2003 | Yu et al. | |
| 6,541,224 B2 | 4/2003 | Yu et al. | |
| 6,562,579 B1 | 5/2003 | Yu et al. | |
| 6,635,482 B1 | 10/2003 | Yu et al. | |
| 6,660,843 B1 | 12/2003 | Feige et al. | |
| 6,689,579 B1 | 2/2004 | Yu et al. | |
| 6,716,576 B1 | 4/2004 | Yu et al. | |
| 6,812,327 B1 | 11/2004 | Yu et al. | |
| 6,869,605 B2 | 3/2005 | Browning et al. | |
| 6,875,846 B2 | 4/2005 | Rennert et al. | |
| 6,881,401 B1 | 4/2005 | Yu et al. | |
| 6,969,519 B2 | 11/2005 | Ruben et al. | |
| 2002/0055625 A1 | 5/2002 | Tribouley | |
| 2002/0086018 A1 | 7/2002 | Theill et al. | |
| 2002/0115112 A1 | 8/2002 | Yu et al. | |
| 2002/0165156 A1* | 11/2002 | Browning et al. | 514/12 |
| 2002/0187526 A1 | 12/2002 | Ruben et al. | |
| 2003/0022233 A1 | 1/2003 | Goodwin et al. | |
| 2003/0059937 A1 | 3/2003 | Ruben et al. | |
| 2003/0077659 A1 | 4/2003 | Baker et al. | |
| 2003/0095967 A1 | 5/2003 | MacKay et al. | |
| 2003/0165986 A1 | 9/2003 | Goodwin et al. | |
| 2003/0166864 A1 | 9/2003 | Yu et al. | |
| 2003/0175208 A1 | 9/2003 | Yu et al. | |
| 2003/0195156 A1 | 10/2003 | Min et al. | |
| 2003/0207354 A1 | 11/2003 | Baker et al. | |
| 2003/0223996 A1 | 12/2003 | Ruben et al. | |
| 2004/0072188 A1 | 4/2004 | Ambrose et al. | |
| 2004/0077064 A1 | 4/2004 | Baker et al. | |
| 2004/0175801 A1 | 9/2004 | Yu et al. | |
| 2004/0175802 A1 | 9/2004 | Yu et al. | |
| 2005/0070689 A1 | 3/2005 | Dixit et al. | |
| 2005/0095243 A1 | 5/2005 | Chan et al. | |
| 2005/0100548 A1 | 5/2005 | Browning et al. | |
| 2005/0124543 A1 | 6/2005 | Rennert et al. | |
| 2005/0163775 A1* | 7/2005 | Chan et al. | |
| 2005/0169924 A1* | 8/2005 | Browning et al. | |
| 2005/0186637 A1* | 8/2005 | Yu et al. | |
| 2005/0244411 A1* | 11/2005 | MacKay et al. | |
| 2005/0255532 A1* | 11/2005 | Ruben et al. | |
| 2006/0003380 A1* | 1/2006 | Ruben et al. | |
| 2006/0062789 A1* | 3/2006 | Ruben et al. | |
| 2007/0249530 A1* | 10/2007 | Kelley et al. | |

FOREIGN PATENT DOCUMENTS

| | | | |
|---|---|---|---|
| EP | 869 180 | * | 10/1998 |
| EP | 911 633 | * | 4/1999 |
| WO | WO 94/10308 | * | 5/1994 |
| WO | WO 97/33902 | * | 9/1997 |
| WO | WO 98/18921 | * | 5/1998 |
| WO | WO 98/27114 | * | 6/1998 |
| WO | WO 98/39361 | * | 9/1998 |
| WO | WO 99/00518 | * | 1/1999 |
| WO | WO 99/11791 | * | 3/1999 |
| WO | WO 99/12964 | * | 3/1999 |
| WO | WO 99/12965 | * | 3/1999 |
| WO | WO 99/33980 | | 7/1999 |
| WO | WO 99/50416 | | 10/1999 |
| WO | WO 00/39295 | | 7/2000 |

(Continued)

OTHER PUBLICATIONS

Abel and Maniatis, "Gene regulation. Action of leucine zippers," *Nature* 341:24 (1989).

(Continued)

*Primary Examiner* — Elly-Gerald Stoica
(74) *Attorney, Agent, or Firm* — Clark & Elbing LLP

(57) ABSTRACT

The present invention relates to polypeptides that inhibit APRIL and/or BAFF binding to BCMA, nucleic acid molecules encoding the polypeptides, and compositions comprising the polypeptides. The present invention also relates to methods for treating an immune-related disease or cancer using the polypeptides and compositions of the invention. The present invention also relates to methods for identifying inhibitors of APRIL/BAFF binding to BCMA and APRIL/BAFF signaling.

26 Claims, 8 Drawing Sheets

FOREIGN PATENT DOCUMENTS

| | | |
|---|---|---|
| WO | WO 00/40716 | 7/2000 |
| WO | WO 00/43032 | 7/2000 |
| WO | WO 00/47740 | 8/2000 |
| WO | WO 00/67034 | 11/2000 |
| WO | WO 01/12812 | 2/2001 |
| WO | WO 01/60397 | 8/2001 |
| WO | WO 01/81417 | 11/2001 |
| WO | WO 01/85782 | 11/2001 |
| WO | WO 01/87977 | 11/2001 |
| WO | WO 01/87979 | 11/2001 |
| WO | WO 02/024909 | 3/2002 |
| WO | WO 02/066516 | 8/2002 |
| WO | WO 02/092620 | 11/2002 |
| WO | WO 03/014294 | 2/2003 |
| WO | WO 03/024991 | 3/2003 |
| WO | WO 03/035846 | 5/2003 |
| WO | WO 03/050134 | 6/2003 |
| WO | WO 2004/016737 | 2/2004 |
| WO | WO 2004/094620 | 11/2004 |
| WO | WO 2005/005462 | 1/2005 |
| WO | WO 2005/075511 | 8/2005 |
| WO | WO 2006/052493 | 5/2006 |

OTHER PUBLICATIONS

Aruffo et al., "CD44 is the principal cell surface receptor for hyaluronate," *Cell* 61:1303-1313 (1990).
Banner et al., "Crystal structure of the soluble human 55 kd TNF receptor-human TNFβ complex: implications for TNF receptor activation," *Cell* 73:431-445 (1993).
Batten et al., "BAFF mediates survival of peripheral immature B lymphocytes," *J. Exp. Med.* 192:1453-1465 (2000).
Bodmer et al., "The molecular architecture of the TNF superfamily," *Trends Biochem. Sci.* 27:19-26 (2002).
Caron et al., "Engineered humanized dimeric forms of IgG are more effective antibodies," *J. Exp. Med.* 176:1191-1195 (1992).
Collaborative Computational Project No. 4, "The CCP4 suite: programs for protein crystallography," *Acta. Cryst* D50:760-763 (1994).
Cha et al., "Crystal structure of TRAIL-DR5 complex identifies a critical role of the unique frame insertion in conferring recognition specificity," *J. Biol. Chem.* 275:31171-31177 (2000).
Chamow and Ashkenazi, "Immunoadhesins: principles and applications," *Trends Biotechnol.* 14:52-60 (1996).
Chan et al., "A domain in TNF receptors that mediates ligand-independent receptor assembly and signaling," *Science* 288:2351-2354 (2000).
Cochran et al., "A minimal peptide scaffold for β-turn display: optimizing a strand position in disulfide-cyclized β-hairpins," *J. Amer. Chem. Soc.* 123:625-632 (2001).
Cornilescu et al., "Protein backbone angle restraints from searching a database for chemical shift and sequence homology," *J. Biomol. NMR* 13:289-302 (1999).
Database UniProt 1, "Tumor necrosis factor receptor superfamily member 17 (B-cell maturation protein)," Database Accession No. Q02223, Jul. 1, 1993 (Abstract).
De Vita et al., "Efficacy of selective B cell blockade in the treatment of rheumatoid arthritis: evidence for a pathogenetic role of B cells," *Arthritis Rheum.* 46:2029-2033 (2002).
Do et al., "Attenuation of apoptosis underlies B lymphocyte stimulator enhancement of humoral immune response," *J. Exp. Med.* 192:953-964 (2000).
Doerks et al., "Protein annotation: detective work for function prediction," *Trends Genet.* 14:248-250 (1998).
Edwards and Cambridge, "Sustained improvement in rheumatoid arthritis following a protocol designed to deplete B lymphocytes," *Rheumatology* 40:205-211 (2001).
Edwards et al., "B-lymphocyte depletion therapy in rheumatoid arthritis and other autoimmune disorders," *Biochem. Soc. T.* 30:824-828 (2002).
Edwards et al., "Efficacy and safety of Rituximab, a B-cell targeted chimeric monoclonal antibody: a randomized, placebo-controlled trial in patients with rheumatoid arthritis," *Arthritis Rheum.* 46 (Abstract 446):S197 (2002).
Fleming et al., "Discovery of high-affinity peptide binders to BLyS by phage display," *J. Mol. Recognit.* 18:94-102 (2005).

GenBank Accession No. AAP57629, Jun. 15, 2003.
GenBank Accession No. AF046888, Sep. 25, 1998.
GenBank Accession No. AF136293, Jul. 25, 2001.
Gordon et al., "BAFF/BLyS receptor 3 comprises a minimal TNF receptor-like module that encodes a highly focused ligand-binding site," *Biochemistry* 42:5977-5983 (2003).
Gross et al., "TACI and BCMA are receptors for a TNF homologue implicated in B-cell autoimmune disease," *Nature* 404:995-999 (2000).
Hahne et al., "APRIL, a new ligand of the tumor necrosis factor family, stimulates tumor cell growth," *J. Exp. Med.* 188:1185-1190 (1998).
Hermann et al., "Protein NMR structure determination with automated NOE assignment using the new software CANDID and the torsion angle dynamics algorithm DYANA," *J. Mol. Biol.* 319:209-227 (2002).
Higashida et al., "Treatment of DMARD-refractory rheumatoid arthritis with Rituximab," Presented at the Annual Scientific Meeting of the American College of Rheumatology, New Orleans, LA (2002).
Hoogenboom et al., "Construction and expression of antibody-tumor necrosis factor fusion proteins," *Mol. Immunol.* 28:1027-1037 (1991).
Hoppe et al., "A parallel three stranded α-helical bundle at the nucleation site of collagen triple-helix formation," *FEBS Lett.* 344:191-195 (1994).
Hymowitz et al., "Triggering cell death: the crystal structure of Apo2L/TRAIL in a complex with Death Receptor 5," *Mol. Cell* 4:563-571.
Hymowitz et al., "A unique zinc-binding site revealed by a high-resolution x-ray structure of homotrimeric Apo2L/TRAIL," *Biochemistry* 39:633-640 (2000).
Hymowitz et al., "Structures of APRIL-receptor complexes," *J. Biol. Chem.* 280:7218-7227 (2005).
Kallad et al., "BAFF: B cell survival factor and emerging therapeutic target for autoimmune disorders," *Expert. Opin. Ther. Targets* 7:115-123 (2003).
Karpusas et al., "Crystal structure of extracellular human BAFF, a TNF family member that stimulates B lymphocytes," *J. Mol. Biol.* 315:1145-1154 (2002).
Kayagaki et al., "BAFF/BLyS receptor 3 binds the B cell survival factor BAFF ligand through a discrete surface loop and promotes processing of NF-κB2," *Immunity* 10:515-524 (2002).
Kelly et al., "APRIL/TRDL-1, a tumor necrosis factor-like ligand, stimulates cell death," *Cancer Res.* 60:1021-1027 (2000).
Khare et al., "Severe B cell hyperplasia and autoimmune disease in TALL-1 transgenic mice," *PNAS* 97:3370-3375 (2000).
Kim et al., "Crystal structure of the BAFF-BAFF-R complex and its implications for receptor activation," *Nat. Struct. Biol.* 10:342-348 (2003).
LaBean and Kauffman, "Design of synthetic gene libraries encoding random sequence proteins with desired ensemble characteristics," *Protein Sci.* 2:1249-1254 (1993).
Landschulz et al., "The leucine zipper: a hypothetical common to a new class of DNA binding proteins" *Science* 240:1759-1764 (1988).
Leandro et al., "B lymphocyte depletion in rheumatoid arthritis: early evidence for safety, efficacy and dose response," *Arthritis Rheum.* 44 (Abstract 1905):S370 (2001).
Leandro et al., "An open study of B lymphocyte depletion in systemic lupus erythematosus," *Arthritis Rheum.* 46:2673-2677 (2002).
Leandro et al., "Clinical outcome in 22 patients with rheumatoid arthritis treated with B lymphocyte depletion," *Ann. Rheum. Dis.* 61:883-888 (2002).
Lee and Kelley, "A novel soluble tissue factor variant with an altered factor VIIa binding interface," *J. Biol. Chem.* 273:4149-4154 (1998).
Levine and Pestronk, "IgM antibody-related polyneuropathies: B-cell depletion chemotherapy using Rituximab," *Neurology* 52:1701-1704 (1999).
Liu et al., "Crystal structure of sTALL-1 reveals a virus-like assembly of TNF family ligands," *Cell* 108:383-394 (2002).
Liu et al., "Ligand-receptor binding revealed by the TNF family member TALL-1," *Nature* 423:49-56 (2003).
Locksley et al., "The TNF and TNF receptor superfamilies: integrating mammalian biology," *Cell* 104:487-501 (2001).

Mackay et al., "BAFF and APRIL: a tutorial on B cell survival," *Annu. Rev. Immunol.* 21:231-264 (2003).
Mackay and Ambrose, "The TNF family members BAFF and APRIL: the growing complexity," *Cytokine Growth Factor Rev.* 14:311-324 (2003).
Marsters et al., "Interaction of the TNF homologues BLyS and APRIL with the TNF receptor homologues BCMA and TACI," *Curr. Biol.* 10:785-788 (2000).
Matthews, "Medical heretics," *New Scientist* 170:34-37 (2001).
Medema et al., "The uncertain glory of APRIL," *Cell Death Differ.* 10:1121-1125 (2003).
Mongkolsapaya et al., "Structure of the TRAIL-DR5 complex reveals mechanisms conferring specificity in apoptotic initiation," *Nat. Struct. Biol.* 6:1048-1053 (1999).
Moore et al., "BLyS: member of the tumor necrosis factor family and B lymphocyte stimulator," *Science* 285:260-263 (1999).
Mukhopadhyay et al., "Identification and characterization of a novel cytokine, THANK, a TNF homologue that activates apoptosis, nuclear factor-κB, and c-Jun $NH_2$-terminal kinase," *J. Biol. Chem.* 274:15978-15981 (1999).
Neri et al., "Stereospecific nuclear magnetic resonance assignments of the methyl groups of valine and leucine in the DNA-binding domain of the 434 repressor by biosynthetically directed fractional $^{13}C$ labeling," *Biochemistry* 28:7510-7516 (1989).
Ngo et al., "Computational complexity, protein structure prediction, and the Levinthal paradox," *The Protein Folding Problem and Tertiary Structure Prediction*, pp. 491-495 (1994).
O'Connor et al., "BCMA is essential for the survival of long-lived bone marrow plasma cells," *J. Exp. Med.* 199:91-97 (2004).
Oren et al., "Structural basis of BLyS receptor recognition," *Nat. Struct. Biol.* 9:288-292 (2002).
Otwinowski and Minor, "Processing of x-ray diffraction data collected in oscillation mode," *Methods Enzymol.* 276:307-326 (1997).
Patel et al., "Engineering an APRIL-specific B cell maturation antigen," *J. Biol. Chem.* 279:16727-16735 (2004).
Pelletier et al., "Comparison of soluble decoy IgG fusion proteins of BAFF-R and BCMA as antagonists for BAFF," *J. Biol. Chem.* 278:33127-33133 (2003).
Perrotta and Abuel, "Response of chronic relapsing ITP of 10 years duration to Rituximab," *Blood* (Abstract 3360) 92 (10 Suppl. 1 Pt. 1-2):88b (1998).
Rennert et al., "A soluble form of B cell maturation antigen, a receptor for the tumor necrosis factor family member APRIL, inhibits tumor cell growth," *J. Exp. Med.* 192:1677-1683 (2000).
Salzer et al., "Mutations in TNFRSF13B encoding TACI are associated with common variable immunodeficiency in humans," *Nat. Genet.* 37:820-828 (2005).
Schiemann et al., "An essential role for BAFF in the normal development of B cells through a BCMA-independent pathway," *Science* 293:2111-2114 (2001).
Schneider et al., "BAFF, a novel ligand of the tumor necrosis factor family, stimulates B cell growth," *J. Exp. Med.* 189:1747-1756 (1999).
Seshasayee et al., "Loss of TACI causes fatal lymphoproliferation and autoimmunity, establishing TACI as an inhibitory BLyS receptor," *Immunity* 18:279-288 (2003).
Shopes, "A genetically engineered human IgG mutant with enhanced cytolytic activity," *J. Immunol.* 148:2918-2922 (1992).
Shu et al., "TALL-1 is a novel member of the TNF family that is down-regulated by mitogens," *J. Leukocyte Biol.* 65:680-683 (1999).
Shu and Johnson, "B cell maturation protein is a receptor for the tumor necrosis factor family member TALL-1," *Proc. Natl. Acad. Sci. USA* 97:9156-9161 (2000).
Sidhu et al., "High copy display of large proteins on phage for functional selections," *J. Mol. Biol.* 296:487-495 (2000).
Sidhu, "Phage display for selection of novel binding peptides," *Methods Enzymol.* 328:333-363 (2000).
Sidhu, "Engineering M13 for phage display," *Biomol. Eng.* 18:57-63 (2001).
Skelton et al., "Origins of PDZ domain ligand specificity," *J. Biol. Chem.* 278:7645-7654 (2003).
Skolnick and Fetrow, "From genes to protein structure and function: novel applications of computational approaches in the genomic era," *Trends Biotech.* 18:34-39 (2000).
Stamenkovic et al., "The B lymphocyte adhesion molecule CD22 interacts with leukocyte common antigen CD45RO on T cells and α2-6 sialyltransferase, CD75, on B cells," *Cell* 66:1133-1144 (1991).
Starovasnik et al., "Solution structure of the E-domain of staphylococcal protein A," *Biochemistry* 35:15558-15569 (1996).
Starovasnik et al., "Antibody variable region binding by staphylococcal protein A: thermodynamic analysis and location of the Fv binding site on E-domain," *Protein Sci.* 8:1423-1431 (1999).
Stasi et al., "Rituximab chimeric anti-CD20 monoclonal antibody treatment for adults with chronic idiopathic thrombocytopenic purpura," *Blood* 98:952-957 (2001).
Stein et al., "APRIL modulates B and T cell immunity," *J. Clin. Invest.* 109:1587-1598 (2002).
Stevenson et al., "A chimeric antibody with dual Fc regions (bisFabFc) prepared by manipulations at the IgG hinge," *Anti-Cancer Drug Design* 3:219-230 (1989).
Thompson et al., "BAFF binds to the tumor necrosis factor receptor-like molecule B cell maturation antigen and is important for maintaining the peripheral B cell population," *J. Exp. Med.* 192:129-135 (2000).
Thompson et al., "BAFF-R, a newly identified TNF receptor that specifically interacts with BAFF," *Science* 293:2108-2111 (2001).
Tuscano, "Successful treatment of Infliximab-refractory rheumatoid arthritis with Rituximab," Presented at the Annual Scientific Meeting of the American College of Rheumatology, New Orleans, LA (2002).
UniProtKB Swiss-Prot Entry O14836, last modified on Jan. 1, 1998 and retrieved on Oct. 7, 2008.
Varfolomeev et al., "APRIL-deficient mice have normal immune system development" *Moi. Cell. Biol.* 24:997-1006 (2004).
von Bülow and Bram, "NF-AT activation induced by a CAML-interacting member of the tumor necrosis factor receptor superfamily," *Science* 278:138-141 (1997).
Wallweber et al., "The crystal structure of a proliferation-inducing ligand, APRIL," *J. Mol. Biol.* 343:283-290 (2004).
Ware, "APRIL and BAFF connect autoimmunity and cancer," *J. Exp. Med.* 192:F35-F37 (2000).
Weiss et al., "Rapid mapping of protein functional epitopes by combinatorial alanine scanning," *Proc. Nat. Acad. Sci. USA* 97:8950-8954 (2000).
Wells, "Additivity of mutational effects in proteins," *Biochemistry* 29:8509-8517 (1990).
Wolff et al., "Monoclonal antibody homodimers: enhanced antitumor activity in nude mice," *Cancer Research* 53:2560-2565 (1993).
Wu et al., "Tumor necrosis factor (TNF) receptor superfamily member TACI is a high affinity receptor for TNF family members APRIL and BLyS," *J. Biol. Chem.* 275:35478-35485 (2000).
Yan et al., "Identification of a receptor for BLyS demonstrates a crucial role in humoral immunity," *Nat. Immunol.* 1:37-41 (2000).
Yan et al., "Identification of a novel receptor for B lymphocyte stimulator that is mutated in a mouse strain with severe B cell deficiency," *Curr. Biol.* 11:1547-1552 (2001).
Yan et al., "Activation and accumulation of B cells in TACI-deficient mice," *Nat. Immunol.* 2:638-643 (2001).
Yu et al., "APRIL and TALL-I and receptors BCMA and TACI: system for regulating humoral immunity," *Nat. Immunol.* 1:252-256 (2000).
International Preliminary Report on Patentability for PCT/US2005/039154, issued May 8, 2007.
International Preliminary Report on Patentability for PCT/US2004/017682, issued Dec. 19, 2005.
International Preliminary Report on Patentability for PCT/US2004/025247, issued Jul. 31, 2006.
International Search Report for PCT/US2005/039154, mailed Apr. 10, 2006.
International Search Report for PCT/US2004/017682, mailed Jan. 12, 2005.
International Search Report for PCT/US2004/025247, mailed Jun. 9, 2005.
Written Opinion of the International Searching Authority for PCT/US2005/039154, received Apr. 10, 2006.
Office Action for U.S. Appl. No. 10/587,370, mailed Oct. 16, 2008.

\* cited by examiner

Human BCMA

MLQMAGQCSQ NEYFDSLLHA CIPCQLRCSS
NTPPLTCQRY CNASVTNSVK GTNAILWTCL
GLSLIISLAV FVLMFLLRKI NSEPLKDEFK
NTGSGLLGMA NIDLEKSRTG DEIILPRGLE
YTVEECTCED CIKSKPKVDS DHCFPLPAME
EGATILVTTK TNDYCKSLPA ALSATEIEKS
ISAR

MiniBR3

TPCVPAECFDLLVRHCVACGLLRTPR

FIG. 5

BCMA-(I22K)-Fc fusion

MSALLILALVGAAVASTAG<u>QCSQNEYFDSLLHAC(K)
PCQLRCSSNTPPLTCQRYC</u>NASVTNSVKGVTDKAAHY
TLCPPCPAPELLGGPSVFLFPPKPKDTLMISRTPEVT
CVVVDVSHEDPEVKFNWYVDGVEVHNAKTKPREEQYN
STYRVVSVLTVLHQDWLNGKEYKCKVSNKALPAPIEK
TISKAKGQPREPQVYTLPPSREEMTKNQVSLTCLVKG
FYPSDIAVEWESNGQPENNYKTTPPVLDSDGSFFLYS
KLTVDKSRWQQGNVFSCSVMHEALHNHYTQKSLSLSP
GKO

Fig. 6

POLYPEPTIDES THAT BIND APRIL

CROSS REFERENCE TO RELATED APPLICATIONS

This application is a Divisional Application of U.S. application Ser. No. 10/587,370, filed on May 29, 2007, now abandoned, which is the U.S. National Phase of PCT/US04/25247, filed Aug. 4, 2004, which claims benefit of Provisional Application No. 60/540,271, filed Jan. 29, 2004, each of which is hereby incorporated by reference.

A Sequence Listing is provided in this patent document as a txt file entitled, "50474_007003 Sequence Listing.txt," created Jul. 28, 2009 (size: 42.8 KB).

FIELD OF THE INVENTION

The present invention relates to new polypeptides that bind APRIL but little or no BAFF, bind BAFF but little or no APRIL, or bind APRIL and BAFF, nucleic acid molecules encoding the polypeptides and compositions comprising them. The present invention also relates to methods for preventing and treating immune related diseases and cancer using the compositions of this invention. The present invention also relates to methods for selecting inhibitors of APRIL and/or BAFF signaling using the polypeptides of this invention.

BACKGROUND AND INTRODUCTION OF THE INVENTION

The tumor necrosis factor receptors (TNFR) are a superfamily of transmembrane receptors involved in cell communication within the immune system. TNFR family members are structurally characterized by extracellular cysteine-rich domains (CRD) that form ligand-binding motifs. Generally, members of the TNFR superfamily found on B or T cells are type I transmembrane proteins that have several CRDs (Bodmer, J. L., et al., (2002) *Trends Biochem Sci* 27:19-26). There is, however, a sub-group of TNFR proteins expressed by B cells that are type III transmembrane proteins and contain a reduced number of CRDs: B-Cell Maturation Antigen (BCMA), Transmembrane Activator and CAML Interactor (TACI), and BLyS (BAFF) Receptor 3 (BR3) (Gross, J. A., et al., (2000) *Nature* 404: 995-999; Marsters, S. A., et al., (2000) *Curr Biol* 10:785-788; Thompson, J. S., et al., (2001) *Science* 293:2108-2111; Yu, G., et al., (2000) *Nat Immunol* 1:252-256. The extracellular domain (ECD) of TACI contains two CRDs, the BCMA ECD comprises one CRD, and the ECD of BR3 contains only a partial CRD. Together with the receptor (Fn14) for the TWEAK ligand, BCMA and BR3 are the smallest members of the TNFR superfamily. TACI, BCMA and BR3 lack an intracellular death domain. It is believed that these receptors are involved in the survival, proliferation, and/or differentiation of a variety of cells.

The TNF family member BAFF is the only known ligand for BR3. BAFF-dependent B cell proliferation appears to require BR3; however, BAFF has also been reported to bind TACI and BCMA (Shu, H. B., and Johnson, H. (2000) *Proc Natl Acad Sci USA* 97:9156-9161; Thompson, J. S., et al., (2001) *Science* 293:2108-2111; Yu, G., et al., (2000) *Nat Immunol* 1:252-256). APRIL (also known as TRDL-1, TALL-2 and TNFSF13A), the TNF family member most closely related to BAFF, binds TACI and BCMA (Marsters, S. A., et al., (2000) *Curr Biol* 10:785-788; Thompson, J. BAFF, binds TACI and BCMA (Marsters, S. A., et al., (2000) *Curr Biol* 10:785-788; Thompson, J. S., et al., (2001) *Science* 293: 2108-2111; Yu, G., et al., (2000) *Nat Immunol* 1:252-256). Despite cross-reactivity with receptors, the expression patterns of BAFF and APRIL are distinct; BAFF is expressed by macrophages, monocytes, and dendritic cells, while APRIL is expressed by lymphoid cells and at elevated levels by some tumor cells (Hahne, M., et al., (1998) *J Exp Med* 188:1185-1190).

Tight regulation of BAFF levels appears to be critical for B cell homeostasis. BAFF knockout mice display significant reduction in the development and survival of follicular and marginal B cells while mice expressing a BAFF transgene develop a lupus-like autoimmune syndrome (Gross, J. A., et al., (2000) *Nature* 404:995-999; Mackay, F., et al., (2001) *Science* 293:2111-2114; Khare, S. D., et al., (2000) *Proc Natl Acad Sci USA* 97:3370-3375). A BAFF-specific antagonist, BR3-Fc (Kayagaki, N., et al., (2002) *Immunity* 17, 515-524), together with studies on BAFF knockout mice (Schiemann, B., et al., (2001) *Science* 293:2111-2114), has been used to demonstrate the essential role of BAFF in B cell development.

The role of APRIL in B cell homeostasis is less clear especially since APRIL knockout mice display normal B cell levels (E. Varfolomeev et al., (2004) *Mol. Cell. Biol* 24(3): 997-1006). However, several groups have reported on its activity in cell proliferation and T cell function. For example, APRIL has been shown to be capable of inducing the proliferation of certain tumors cell lines in vitro and in vivo (Hahne, M., et al., (1998) *J. Exp. Med.* 188:1185-1190). APRIL transgenic mice displayed augmented T cell independent B cell responses and increased survival of T cells (Stein J. et al. (2002) *J Clin Invest* 109:1587-98). APRIL expression has also been shown to be upregulated in many tumors including colon and prostate cancers (Hahne, M., et al., (1998) *J Exp Med* 188:1185-1190; Rennert, P., et al., (2000) *J Exp Med* 192:1677-1684; Kelly, K., et al., (2000) *Cancer Res* 60:1021-1027.

Both BCMA-Fc and TACI-Fc can inhibit the proliferation of primary B cells stimulated by APRIL (Yu, G., et al. (2000) *Nat. Immunol.* 1:252-256). Studies have shown the attenuation of autoimmune lupus-like disease progression in mice with BR3-Fc treatment (e.g., Kayagaki, N., et al., (2002) *Immunity* 17:515-524). A soluble form of BCMA (BCMA-Fc) has been shown to inhibit tumor cell growth in Nu/Nu mice implanted with HT29 and A549 tumor cells (Rennert, P., et al. (2000) *J. Exp. Med.* 192:1677-1683).

Several reports have described the nanomolar binding affinity of BAFF to BCMA (Marsters, S. A., et al., (2000) *Curr Biol* 10:785-788; Shu, H. B., and Johnson, H. (2000) *Proc Natl Acad Sci USA* 97:9156-9161; Yu, G., et al., (2000) *Nat Immunol* 1:252-256), however these studies used a bivalent BCMA receptor-Fc fusion construct that could result in measured affinities that are enhanced by avidity. Pelletier et al. has anecdotally reported that a monovalent BCMA-Fc fusion protein created by mutating its Fc region interacts with BAFF with low affinity (Pelletier, M et al. (2003) *JBC* 278 (35):33127-33133). None of these reports explored or identified the residues in BCMA that determine specificity for its binding to APRIL or BAFF as a BCMA monomer or multimer.

SUMMARY OF THE INVENTION

The present invention provides new polypeptide molecules that bind APRIL but bind little or no BAFF, bind BAFF but little or no APRIL, bind APRIL and BAFF, or bind BAFF and/or APRIL with decreased affinity as compared to a native BCMA polypeptide. The polypeptides of this invention are useful for research or medicinal purposes, including treating and diagnosing diseases, detecting APRIL and BAFF levels and developing inhibitors of the APRIL and BAFF signaling pathways. The polypeptides of this invention include monomers and multimers. The present invention provides compositions comprising the polypeptides or the nucleic acid molecules of this invention, methods for producing and using the polypeptides, and nucleic acid molecules encoding the polypeptides of this invention. In one embodiment, the polypeptides of this invention are derived from a BCMA sequence, such as the sequence of the extracellular domain of human BCMA.

In one embodiment, a monomeric polypeptide of this invention binds APRIL with an IC50 value equal to or less than 100 nM and binds BAFF with an IC50 value equal to or greater than 100 uM. In one embodiment, a multimeric polypeptide of this invention binds BAFF with an IC50 value equal to or less than 100 nM and binds APRIL with an affinity that is thirty fold weaker than native BCMA binding to APRIL. In another embodiment, a monomeric polypeptide of this invention binds to BAFF and APRIL with affinities within the same order of magnitude. In another embodiment, a multimeric polypeptide of this invention binds to APRIL with an affinity less than 100 nM or less than 10 nM, with little or no binding to BAFF.

In one embodiment, a polypeptide of this invention is a BCMA variant that has been derived from a mammalian BCMA polypeptide sequence wherein at least one amino acid residue corresponding to a residue selected from the group consisting of Q10, E12, Y13, F14, I22, Q25 and R27 of FIG. 5 has been altered. According to one embodiment, the BCMA variant has at least one substitution corresponding to a mammalian BCMA residue selected from the group consisting of I22K, R27Y, R27A, Q25D, Y13S, Y13F and Y13A. In one preferred embodiment, the BCMA variant is derived from at least the cysteine-rich domain (CRD) of a mammalian BCMA polypeptide. In another preferred embodiment, the BCMA variant is derived from at least the extracellular domain (ECD) sequence of a mammalian BCMA. In yet a further embodiment, the CRD sequence from which the BCMA variant is derived is a CRD sequence of a human BCMA polypeptide (e.g., residues 8-41 of FIG. 5) (SEQ ID NO:22). According to another embodiment, the BCMA variant comprises at least one substitution corresponding to a mammalian BCMA residue at I22K.

In one embodiment, the BCMA variant comprises alterations at an amino acid residue corresponding to I22 and an amino acid residue corresponding to any one of the group consisting of F14 and Q25 of FIG. 5. In one preferred embodiment, the BCMA variant is substituted with I22K in combination with any one or all of the group consisting of F14A and Q25A. In another embodiment, the BCMA variant comprises alterations at an amino acid residue corresponding to R27 and a residue corresponding to any one of the group consisting of Y13 and Q25 of FIG. 5. In one further embodiment, the BCMA variant is substituted with at least R27Y or R27A in combination with Y13S, Y13F or Y13A. In another embodiment, the BCMA variant is substituted with Q25D in combination with R27Y or R27A (Q25D/R27 variant). In another embodiment, the Q25D/R27 variant is further substituted with Y13S, Y13F or Y13A.

In one embodiment, a polypeptide of this invention that binds APRIL comprises the sequence of Formula I:

(Formula I)
(SEQ ID NO: 1)
C-$X_2$-$X_3$-$X_4$-$X_5$-Y-$X_7$-D-$X_9$-L $X_{11}$-$X_{12}$-$X_{13}$-C-K-$X_{16}$-C-
$X_{18}$-$X_{19}$-$X_{20}$-C-$X_{22}$-$X_{23}$-$X_{24}$-$X_{25}$-$X_{26}$-$X_{27}$-$X_{28}$-$X_{29}$-C-
$X_{31}$-$X_{32}$-$X_{33}$-C wherein $X_{11}$ is any amino acid residue except A;

wherein $X_2$, $X_3$, $X_4$, $X_5$, $X_7$, $X_9$, $X_{11}$, $X_{12}$, $X_{13}$, $X_{16}$, $X_{18}$, $X_{19}$, $X_{20}$, $X_{22}$, $X_{23}$, $X_{24}$, $X_{25}$, $X_{26}$, $X_{27}$, $X_{28}$, $X_{29}$, $X_{31}$, $X_{32}$, $X_{33}$ are any amino acid except cysteine.

In a further embodiment, the polypeptide comprising Formula I further comprises the sequence NSVKGT linked carboxy-terminal to the thirty-fourth residue of Formula I.

In a further embodiment, $X_{11}$ is L, I or V in Formula I (SEQ ID NO:3). In another embodiment, $X_{18}$ is selected from the group consisting of Q, D and A in Formula I (SEQ ID NO:4). In another embodiment of Formula I, if $X_{20}$ is Y, then $X_{18}$ is D (SEQ ID NO:5). In another embodiment of Formula I, X20 is R (SEQ ID NO:28). In further embodiment, the sequence of Formula I is selected from the group consisting of:

(SEQ ID NO: 6)
CSQNEYFDSLLHACKPCQLRCSSNTPPLTCQRYC, (SEQ ID NO: 7)
CSQNEYFDSLLHACKPCDLRCSSNTPPLTCQRYC, (SEQ ID NO: 8)
CSQNEYFDSLLHACKPCDLYCSSNTPPLTCQRYC,
and (SEQ ID NO: 9)
CSQNEYFDSLVHACKPCQLRCSSNTPPLTCQRYC.

In a further embodiment, the polypeptide comprising Formula I further comprises the sequence NSVKGT linked carboxy-terminal to the thirty-fourth residue of Formula I (SEQ ID NO:2).

In one embodiment, a polypeptide of this invention that binds BAFF comprises the sequence of Formula II:

(Formula II)
(SEQ ID NO: 10)
C-$X_2$-$X_3$-$X_4$-$X_5$-$X_6$-$X_7$-D-$X_9$-L-$X_{11}$-$X_{12}$-$X_{13}$-C-$X_{15}$-$X_{16}$-C-
$X_{18}$-$X_{19}$-$X_{20}$-C-$X_{22}$-$X_{23}$-$X_{24}$-$X_{25}$-$X_{26}$-$X_{27}$-$X_{28}$-$X_{29}$-C-
$X_{31}$-$X_{32}$-$X_{33}$-C wherein $X_6$ is selected from the group consisting of Y, A, D, S and F;

wherein $X_{11}$ is any amino acid residue except A;

wherein $X_{15}$ is any amino acid residue except A or K;

wherein $X_{18}$ is selected from the group consisting of Q, D and A;

wherein $X_{20}$ is selected from the group consisting of R, Y and A;

wherein $X_2$, $X_3$, $X_4$, $X_5$, $X_7$, $X_9$, $X_{10}$, $X_{12}$, $X_{13}$, $X_{16}$, $X_{19}$, $X_{22}$, $X_{23}$, $X_{24}$, $X_{25}$, $X_{26}$, $X_{27}$, $X_{28}$, $X_{29}$, $X_{31}$, $X_{32}$ and $X_{33}$ are any amino acid except cysteine; and provided that the Formula II does not comprise the sequence

```
CSQNEYFDSLLHACIPCQLRCSSNTPPLTCQRYC.
```

In an embodiment of Formula II, $X_{11}$ is L, I or V (SEQ ID NO:11). In an embodiment of Formula II, $X_{15}$ is I, V or A (SEQ ID NO:12). In an embodiment of Formula II, $X_{18}$ is D and $X_{20}$ is Y (SEQ ID NO:33). In another embodiment of Formula II, the sequence of Formula II is selected from the group consisting of

```
                              (SEQ ID NO: 13)
CSQNEAFDSLLHACIPCQLRCSSNTPPLTCQRYC, (SEQ ID NO: 14)
CSQNESFDSLLHACIPCQLRCSSNTPPLTCQRYC, (SEQ ID NO: 15)
CSQNEFFDSLLHACIPCQLRCSSNTPPLTCQRYC, (SEQ ID NO: 16)
CSQNEYFDSLLHACIPCDLRCSSNTPPLTCQRYC, (SEQ ID NO: 17)
CSQNEYFDSLLHACIPCQLYCSSNTPPLTCQRYC,
and (SEQ ID NO: 18)
CSQNEYFDSLLHACIPCDLYCSSNTPPLTCQRYC.
```

In a further embodiment, the polypeptide comprising Formula II further comprises the sequence NSVKGT linked carboxy-terminal to the thirty-fourth residue (SEQ ID NO: 19).

In yet another embodiment, the polypeptides of this invention comprise heterologous sequences N-terminal, C-terminal or both N-terminal and C-terminal to the sequence of Formula I or Formula II, i.e., heterologous to a BCMA polypeptide. In yet another embodiment, the amino acid sequence of Formula I and Formula II are 85% or more, 90% or more, 95% or more or 99% or more identical to the CRD sequence of a native BCMA.

In yet another embodiment, the polypeptide of this invention is an immunoadhesin. In another embodiment, the polypeptide of this invention is an antibody. In one further embodiment of the invention, the antibody is selected from the group consisting of an F(ab) antibody, F(ab')$_2$ antibody and a scFv antibody. In another embodiment of the invention, the antibody is a multi-specific antibody (e.g., bispecific or trispecific). In another embodiment of the invention, the antibody is a humanized antibody.

In yet another embodiment, the polypeptide of this invention is attached directly or indirectly to an agent selected from the group consisting of a growth inhibitory agent, a cytotoxic agent, a detection agent, an agent that improves the bioavailability of the polypeptide, an agent that improves the half-life of the polypeptide, an agent that improves drug performance by optimizing pharmacokinetics, an agent that decreases immunogenicity of the polypeptide, and an agent that decreases dosing frequency. In another embodiment, the cytotoxic agent is selected from the group consisting of a toxin, an antibiotic and a radioactive isotope. In another embodiment, the agent is a non-proteinaceous polymer such as a molecule comprising polyethylene glycol (PEG). In further embodiment, the nonproteinaceous polymer comprises a hydrophilic, synthetic polymer, such as PEG. In some embodiments, the non-proteinaceous polymer is selected from the group consisting of 2 k PEG, 5 k PEG and 20 k PEG.

The present invention provides nucleic acid molecules that encode the polypeptides of this invention and host cells comprising the nucleic acid molecules. The present invention also provides a method for making the polypeptides of this invention comprising the step of culturing a host cell comprising the nucleic acid molecule of this invention and recovering the protein expressed by the host cell. The present invention further comprises an article of manufacture comprising a polypeptide or nucleic acid molecule of this invention.

The present invention further provides a composition comprising a polypeptide or nucleic acid molecule of this invention optionally further comprising a pharmaceutically acceptable carrier. The composition can further comprise a second therapeutic agent selected from the group consisting of an agent for treating an immune-related disease, a chemotherapeutic agent and a cytotoxic agent.

The present invention provides a method for identifying an inhibitor of APRIL binding to an APRIL receptor comprising the step of detecting an inhibitor that partially or fully blocks a polypeptide of this invention from binding to APRIL. The present invention provides a method for identifying an inhibitor of BAFF binding to a BAFF receptor comprising the step of detecting an inhibitor that partially or fully blocks a polypeptide of this invention from binding to BAFF. The present invention also provides a method for inhibiting APRIL binding to BCMA in a mammal comprising the step of administering a composition of this invention in an amount effective to inhibit binding between APRIL and BCMA in the mammal. The present invention also provides a method for inhibiting BAFF binding to BCMA in a mammal comprising the step of administering a composition of this invention in an amount effective to inhibit binding between BAFF and BCMA in the mammal. The present invention provides a method for inhibiting APRIL signaling in a mammal comprising the step of administering a composition of this invention in an amount effective to inhibit binding between APRIL and BCMA in the mammal. The present invention provides a method for inhibiting BAFF signaling in a mammal comprising the step of administering a composition of this invention in an amount effective to inhibit binding between BAFF and BCMA in the mammal.

The polypeptides of this invention are useful for treating diseases, including diseases characterized by increased levels of expression of BAFF, APRIL and/or BCMA as compared to subjects not suffering from the disease.

The polypeptides of this invention are useful for treating immune-related diseases. In one preferred embodiment, the immune-related disease is an autoimmune disease. In a further embodiment the autoimmune disease is selected from the group consisting of rheumatoid arthritis, multiple sclerosis, systemic lupus erythematosis, myasthenia gravis and insulin dependent diabetes mellitus. In one preferred embodiment, BAFF-inhibiting polypeptides of this invention used to treat or prevent immune-related diseases in patients. In another embodiment, the immune-related disease is a T-cell mediated disease associated with immunosuppression, e.g., graft rejection, graft verses host disease (GVHD) and inflammation (joint pain, swelling anemia or septic shock).

The polypeptides of this invention are useful for treating cancer in a mammal. In one preferred embodiment, polypeptides of this invention are used to treat or prevent a cancer in patients, wherein the cancer to be treated expresses higher levels of APRIL or BAFF than a normal tissue. In one embodiment, the cancer to be treated is selected from the group consisting of a leukemia, a lymphoma, or a myeloma. In another embodiment the cancer to be treated is a gastrointestinal tumor, such as tumor in the rectum, duodenum, colon, stomach and esophagus.

BRIEF DESCRIPTION OF THE DRAWINGS

FIG. 5. Sequence of human BCMA protein (SEQ ID NO:20) and the mini-BR3 (SEQ ID NO: 30).

FIG. 6. The protein sequence of BCMA(I22K)-Fc fusion protein (SEQ ID NO:31). The underlined portion refers to residues 5-51 of human BCMA. The "(K)" refers to a substitution at a residue corresponding to 122 of human BCMA.

DETAILED DESCRIPTION

Figure 1A:
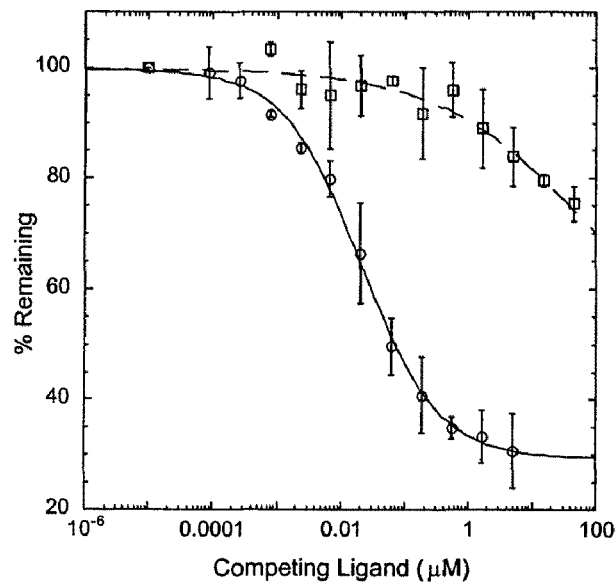
FIG. 1A-C. Competitive displacement ELISA of BCMA ligand interaction, A. Inhibition of BCMA-Z binding to immobilized APRIL (circle) or BAFF (square) in the presence of increasing amounts of the same soluble ligand. Data represent the mean±s.d. of three data sets with IC50 values of 20 nM for APRIL and >65 µM for BAFF. B. Displacement of biotinylated BCMA binding to immobilized APRIL by unbiotinylated BCMA (circle—biotinylated baculovirus BCMA and unlabeled baculovirus BCMA, square—biotinylated baculovirus BCMA and unlabeled BCMA-Z, diamond—biotinylated BCMA-Z and unlabeled baculovirus BCMA, x—biotinylated BCMA-Z and unlabeled BCMA-Z). C. Data shown are for BCMA-Z competing with biotinylated BCMA-Z for binding to immobilized APRIL (circle; IC50=11 nM) or BCMA-Z competing with biotinylated BR3 for binding to immobilized BAFF (square; IC50=8 µM). Data represent the mean±s.d. of three data sets and curves represent fitting to a four-parameter equation.

The terms "BCMA," "BCMA polypeptide," "BCMA protein" when used herein encompasses "native BCMA polypeptides" and "BCMA variants" and homologs and fragments (such as a soluble extracellular portion thereof) and variants thereof, which have a biological activity of a BCMA. For example, a "BCMA" is a designation given to the BCMA polypeptide encoded by the amino acid sequence shown in FIG. 5 (SEQ ID NO:20). According to one preferred embodiment, the BCMA polypeptide is or is derived from a mammalian BCMA. According to another preferred embodiment, the BCMA polypeptide is or is derived from a human BCMA.

A biological activity of a BCMA polypeptide is used herein in the broadest sense, and includes any molecule that binds an APRIL polypeptide but binds little or no a BAFF polypeptide (e.g., a BCMA variant comprising a substitution at a residue corresponding to I22), binds a BAFF polypeptide but binds little or no APRIL polypeptide (e.g., a BCMA variant comprising a substitution at a residue corresponding to R27 and Y13) or binds both APRIL and BAFF polypeptides within a similar order of magnitude (e.g., a BCMA variant comprising a substitution at a residue corresponding to R27 and Q25). In one embodiment, the biological activity of a BCMA polypeptide that binds an APRIL polypeptide but little or no BAFF polypeptide further includes the ability to partially or fully block, inhibit, or neutralize signaling by APRIL. In another embodiment, the biological activity of a BCMA polypeptide that binds a BAFF polypeptide but binds little or no APRIL polypeptide further includes the ability to partially or fully block, inhibit, or neutralize signaling by BAFF. In another embodiment, the biological activity of the BCMA polypeptide that binds both APRIL and BAFF polypeptides further includes the ability to partially or fully block, inhibit, or neutralize signaling by APRIL and BAFF.

According to one embodiment, the polypeptide of this invention comprises an amino acid sequence that is 85% or more identical to a "cysteine-rich domain" (CRD) sequence of a native BCMA. In one preferred embodiment, the CRD is derived from a human BCMA. In another preferred embodiment, the CRD is residue numbers 8-41 of the human BCMA protein described in FIG. 5. In another embodiment, the amino acid sequence is 90% or more identical to a CRD sequence of a native BCMA. In yet another embodiment, the amino acid sequence is 95% or more identical to a CRD sequence of a native BCMA. In yet another embodiment, the amino acid sequence is 99% or more identical to a CRD sequence of a native BCMA.

According to another embodiment, the polypeptide of this invention comprises an amino acid sequence that is 85% or more identical to an extracellular domain (ECD) sequence of a BCMA. In one preferred embodiment, the ECD is derived from a human BCMA. In another preferred embodiment, the ECD approximately residue numbers 1-52 of the human BCMA protein described in FIG. 5. In another embodiment, the amino acid sequence is 90% or more identical to an ECD sequence of a native BCMA. In yet another embodiment, the amino acid sequence is 95% or more identical to an ECD sequence of native BCMA. In yet another embodiment, the amino acid sequence is 99% or more identical to an ECD sequence of native BCMA.

"Percent (%) amino acid sequence identity" with respect to the BCMA polypeptide sequences identified herein is defined as the percentage of amino acid residues in a candidate sequence that are identical with the amino acid residues in the polypeptide being compared, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc. and the source code (Table 1) has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. The ALIGN-2 program should be compiled for use on a UNIX operating system, preferably digital UNIX V4.0D. All sequence comparison parameters are set by the ALIGN-2 program and do not vary.

TABLE 1

```
/*
 *
 * C-C increased from 12 to 15
 * Z is average of EQ
 * B is average of ND
 * match with stop is _M; stop-stop = 0; J (joker) match = 0
 */
#define _M      -8     /* value of a match with a stop */
int        _day[26][26] = {
/*        A  B  C  D  E  F  G  H  I  J  K  L  M  N  O  P  Q  R  S  T  U  V  W  X  Y  Z */
/* A */  { 2, 0,-2, 0, 0,-4, 1,-1,-1, 0,-1,-2,-1, 0,_M, 1, 0,-2, 1, 1, 0, 0,-6, 0,-3, 0},
/* B */  { 0, 3,-4, 3, 2,-5, 0, 1,-2, 0, 0,-3,-2, 2,_M,-1, 1, 0, 0, 0, 0,-2,-5, 0,-3, 1},
/* C */  {-2,-4,15,-5,-5,-4,-3,-3,-2, 0,-5,-6,-5,-4,_M,-3,-5,-4, 0,-2, 0,-2,-8, 0, 0,-5},
/* D */  { 0, 3,-5, 4, 3,-6, 1, 1,-2, 0, 0,-4,-3, 2,_M,-1, 2,-1, 0, 0, 0,-2,-7, 0,-4, 2},
/* E */  { 0, 2,-5, 3, 4,-5, 0, 1,-2, 0, 0,-3,-2, 1,_M,-1, 2,-1, 0, 0, 0,-2,-7, 0,-4, 3},
/* F */  {-4,-5,-4,-6,-5, 9,-5,-2, 1, 0,-5, 2, 0,-4,_M,-5,-5,-4,-3,-3, 0,-1, 0, 0, 7,-5},
/* G */  { 1, 0,-3, 1, 0,-5, 5,-2,-3, 0,-2,-4,-3, 0,_M,-1,-1,-3, 1, 0, 0,-1,-7, 0,-5, 0},
/* H */  {-1, 1,-3, 1, 1,-2,-2, 6,-2, 0, 0,-2,-2, 2,_M, 0, 3, 2,-1,-1, 0,-2,-3, 0, 0, 2},
/* I */  {-1,-2,-2,-2,-2, 1,-3,-2, 5, 0,-2, 2, 2,-2,_M,-2,-2,-2,-1, 0, 0, 4,-5, 0,-1,-2},
/* J */  { 0, 0, 0, 0, 0, 0, 0, 0, 0, 0, 0, 0, 0, 0,_M, 0, 0, 0, 0, 0, 0, 0, 0, 0, 0, 0},
/* K */  {-1, 0,-5, 0, 0,-5,-2, 0,-2, 0, 5,-3, 0, 1,_M,-1, 1, 3, 0, 0, 0,-2,-3, 0,-4, 0},
/* L */  {-2,-3,-6,-4,-3, 2,-4,-2, 2, 0,-3, 6, 4,-3,_M,-3,-2,-3,-3,-1, 0, 2,-2, 0,-1,-2},
/* M */  {-1,-2,-5,-3,-2, 0,-3,-2, 2, 0, 0, 4, 6,-2,_M,-2,-1, 0,-2,-1, 0, 2,-4, 0,-2,-1},
/* N */  { 0, 2,-4, 2, 1,-4, 0, 2,-2, 0, 1,-3,-2, 2,_M,-1, 1, 0, 1, 0, 0,-2,-4, 0,-2, 1},
/* O */  {_M,_M,_M,_M,_M,_M,_M,_M,_M,_M,_M,_M,_M,_M,
0,_M,_M,_M,_M,_M,_M,_M,_M,_M,_M,_M},
/* P */  { 1,-1,-3,-1,-1,-5,-1, 0,-2, 0,-1,-3,-2,-1,_M, 6, 0, 0, 1, 0, 0,-1,-6, 0,-5, 0},
/* Q */  { 0, 1,-5, 2, 2,-5,-1, 3,-2, 0, 1,-2,-1, 1,_M, 0, 4, 1,-1,-1, 0,-2,-5, 0,-4, 3},
/* R */  {-2, 0,-4,-1,-1,-4,-3, 2,-2, 0, 3,-3, 0, 0,_M, 0, 1, 6, 0,-1, 0,-2, 2, 0,-4, 0},
/* S */  { 1, 0, 0, 0, 0,-3, 1,-1,-1, 0, 0,-3,-2, 1,_M, 1,-1, 0, 2, 1, 0,-1,-2, 0,-3, 0},
/* T */  { 1, 0,-2, 0, 0,-3, 0,-1, 0, 0, 0,-1,-1, 0,_M, 0,-1,-1, 1, 3, 0, 0,-5, 0,-3, 0},
/* U */  { 0, 0, 0, 0, 0, 0, 0, 0, 0, 0, 0, 0, 0, 0,_M, 0, 0, 0, 0, 0, 0, 0, 0, 0, 0, 0},
/* V */  { 0,-2,-2,-2,-2,-1,-1,-2, 4, 0,-2, 2, 2,-2,_M,-1,-2,-2,-1, 0, 0, 4,-6, 0,-2,-2},
/* W */  {-6,-5,-8,-7,-7, 0,-7,-3,-5, 0,-3,-2,-4,-4,_M,-6,-5, 2,-2,-5, 0,-6,17, 0, 0,-6},
/* X */  { 0, 0, 0, 0, 0, 0, 0, 0, 0, 0, 0, 0, 0, 0,_M, 0, 0, 0, 0, 0, 0, 0, 0, 0, 0, 0},
/* Y */  {-3,-3, 0,-4,-4, 7,-5, 0,-1, 0,-4,-1,-2,-2,_M,-5,-4,-4,-3,-3, 0,-2, 0, 0,10,-4},
/* Z */  { 0, 1,-5, 2, 3,-5, 0, 2,-2, 0, 0,-2,-1, 1,_M, 0, 3, 0, 0, 0, 0,-2,-6, 0,-4, 4}
};
/*
*/
#include <stdio.h>
#include <ctype.h>
#define MAXJMP   16      /* max jumps in a diag */
#define MAXGAP   24      /* don't continue to penalize gaps larger than this */
#define JMPS     1024    /* max jmps in an path */
#define MX       4       /* save if there's at least MX-1 bases since last jmp */
#define DMAT     3       /* value of matching bases */
#define DMIS     0       /* penalty for mismatched bases */
#define DINS0    8       /* penalty for a gap */
#define DINS1    1       /* penalty per base */
#define PINS0    8       /* penalty for a gap */
#define PINS1    4       /* penalty per residue */
struct jmp {
        short           n[MAXJMP];      /* size of jmp (neg for dely) */
        unsigned short  x[MAXJMP];      /* base no. of jmp in seq x */
};                                      /* limits seq to 2^16 -1 */
struct diag {
        int             score;          /* score at last jmp */
        long            offset;         /* offset of prev block */
```

TABLE 1-continued

```
            short           ijmp;           /* current jmp index */
            struct jmp      jp;             /* list of jmps */
    };
    struct path {
            int             spc;            /* number of leading spaces */
            short           n[JMPS];        /* size of jmp (gap) */
            int             x[JMPS];        /* loc of jmp (last elem before gap) */
    };
    char            *ofile;                 /* output file name */
    char            *namex[2];              /* seq names: getseqs( ) */
    char            *prog;                  /* prog name for err msgs */
    char            *seqx[2];               /* seqs: getseqs( ) */
    int             dmax;                   /* best diag: nw( ) */
    int             dmax0;                  /* final diag */
    int             dna;                    /* set if dna: main( ) */
    int             endgaps;                /* set if penalizing end gaps */
    int             gapx, gapy;             /* total gaps in seqs */
    int             len0, len1;             /* seq lens */
    int             ngapx, ngapy;           /* total size of gaps */
    int             smax;                   /* max score: nw( ) */
    int             *xbm;                   /* bitmap for matching */
    long            offset;                 /* current offset in jmp file */
    struct  diag    *dx;                    /* holds diagonals */
    struct  path    pp[2];                  /* holds path for seqs */
    char            *calloc( ), *malloc( ), *index( ), *strcpy( );
    char            *getseq( ), *g_calloc( );
    /* Needleman-Wunsch alignment program
     *
     * usage: progs file1 file2
     * where file1 and file2 are two dna or two protein sequences.
     * The sequences can be in upper- or lower-case an may contain ambiguity
     * Any lines beginning with ';', '>' or '<' are ignored
     * Max file length is 65535 (limited by unsigned short x in the jmp struct)
     * A sequence with ⅓ or more of its elements ACGTU is assumed to be DNA
     * Output is in the file "align.out"
     *
     * The program may create a tmp file in /tmp to hold info about traceback.
     * Original version developed under BSD 4.3 on a vax 8650
     */
    #include "nw.h"
    #include "day.h"
    static    _dbval[26] = {
        1,14,2,13,0,0,4,11,0,0,12,0,3,15,0,0,0,5,6,8,8,7,9,0,10,0
    };
    static    _pbval[26] = {
        1, 2|(1<<('D'-'A'))|(1<<('N'-'A')), 4, 8, 16, 32, 64,
        128, 256, 0xFFFFFFF, 1<<10, 1<<11, 1<<12, 1<<13, 1<<14,
        1<<15, 1<<16, 1<<17, 1<<18, 1<<19, 1<<20, 1<<21, 1<<22,
        1<<23, 1<<24, 1<<25|(1<<('E'-'A'))|(1<<('Q'-'A'))
    };
    main(ac, av)                                                                    main
            int     ac;
            char    *av[ ];
    {
            prog = av[0];
            if (ac != 3) {
                    fprintf(stderr,"usage: %s file1 file2\n", prog);
                    fprintf(stderr,"where file1 and file2 are two dna or two protein sequences.\n");
                    fprintf(stderr,"The sequences can be in upper- or lower-case\n");
                    fprintf(stderr,"Any lines beginning with ';' or '<' are ignored\n");
                    fprintf(stderr,"Output is in the file \"align.out\"\n");
                    exit(1);
            }
            namex[0] = av[1];
            namex[1] = av[2];
            seqx[0] = getseq(namex[0], &len0);
            seqx[1] = getseq(namex[1], &len1);
            xbm = (dna)? _dbval : _pbval;
            endgaps = 0;                    /* 1 to penalize endgaps */
            ofile = "align.out";            /* output file */
            nw( );                          /* fill in the matrix, get the possible jmps */
            readjmps( );                    /* get the actual jmps */
            print( );                       /* print stats, alignment */
            cleanup(0);                     /* unlink any tmp files */
    }
    /* do the alignment, return best score: main( )
     * dna: values in Fitch and Smith, PNAS, 80, 1382-1386, 1983
     * pro: PAM 250 values
     * When scores are equal, we prefer mismatches to any gap, prefer
     * a new gap to extending an ongoing gap, and prefer a gap in seqx
```

TABLE 1-continued

```
 * to a gap in seq y.
 */
nw( )
{
        char            *px, *py;           /* seqs and ptrs */
        int             *ndely, *dely;      /* keep track of dely */
        int             ndelx, delx;        /* keep track of delx */
        int             *tmp;               /* for swapping row0, row1 */
        int             mis;                /* score for each type */
        int             ins0, ins1;         /* insertion penalties */
        register        id;                 /* diagonal index */
        register        ij;                 /* jmp index */
        register        *col0, *col1;       /* score for curr, last row */
        register        xx, yy;             /* index into seqs */
        dx = (struct diag *)g_calloc("to get diags", len0+len1+1, sizeof(struct diag));
        ndely = (int *)g_calloc("to get ndely", len1+1, sizeof(int));
        dely = (int *)g_calloc("to get dely", len1+1, sizeof(int));
        col0 = (int *)g_calloc("to get col0", len1+1, sizeof(int));
        col1 = (int *)g_calloc("to get col1", len1+1, sizeof(int));
        ins0 = (dna)? DINS0 : PINS0;
        ins1 = (dna)? DINS1 : PINS1;
        smax = −10000;
        if (endgaps) {
                for (col0[0] = dely[0] = −ins0, yy = 1; yy <= len1; yy++) {
                        col0[yy] = dely[yy] = col0[yy−1] − ins1;
                        ndely[yy] = yy;
                }
                col0[0] = 0;        /* Waterman Bull Math Biol 84 */
        }
        else
                for (yy = 1; yy <= len1; yy++)
                        dely[yy] = −ins0;
        /* fill in match matrix
         */
        for (px = seqx[0], xx = 1; xx <= len0; px++, xx++) {
                /* initialize first entry in col
                 */
                if (endgaps) {
                        if (xx == 1)
                                col1[0] = delx = −(ins0+ins1);
                        else
                                col1[0] = delx = col0[0] − ins1;
                        ndelx = xx;
                }
                else {
                        col1[0] = 0;
                        delx = −ins0;
                        ndelx = 0;
                }
                for (py = seqx[1], yy = 1; yy <= len1; py++, yy++) {
                        mis = col0[yy−1];
                        if (dna)
                                mis += (xbm[*px−'A']&xbm[*py−'A'])? DMAT : DMIS;
                        else
                                mis += _day[*px−'A'][*py−'A'];
                        /* update penalty for del in x seq;
                         * favor new del over ongong del
                         * ignore MAXGAP if weighting endgaps
                         */
                        if (endgaps || ndely[yy] < MAXGAP) {
                                if (col0[yy] − ins0 >= dely[yy]) {
                                        dely[yy] = col0[yy] − (ins0+ins1);
                                        ndely[yy] = 1;
                                } else {
                                        dely[yy] −= ins1;
                                        ndely[yy]++;
                                }
                        } else {
                                if (col0[yy] − (ins0+ins1) >= dely[yy]) {
                                        dely[yy] = col0[yy] − (ins0+ins1);
                                        ndely[yy] = 1;
                                } else
                                        ndely[yy]++;
                        }
                        /* update penalty for del in y seq;
                         * favor new del over ongong del
                         */
                        if (endgaps || ndelx < MAXGAP) {
                                if (col1[yy−1] − ins0 >= delx) {
```

TABLE 1-continued

```
                        delx = col1[yy-1] - (ins0+ins1);
                        ndelx = 1;
                } else {
                        delx -= ins1;
                        ndelx++;
                }
        } else {
                if (col1[yy-1] - (ins0+ins1) >= delx) {
                        delx = col1[yy-1] - (ins0+ins1);
                        ndelx = 1;
                } else
                        ndelx++;
        }
        /* pick the maximum score; we're favoring
         * mis over any del and delx over dely
         */
                                                                ...nw
        id = xx - yy + len1 - 1;
        if (mis >= delx && mis >= dely[yy])
                col1[yy] = mis;
        else if (delx >= dely[yy]) {
                col1[yy] = delx;
                ij = dx[id].ijmp;
                if (dx[id].jp.n[0] && (!dna || (ndelx >= MAXJMP
                    && xx > dx[id].jp.x[ij]+MX) || mis > dx[id].score+DINS0)) {
                        dx[id].ijmp++;
                        if (++ij >= MAXJMP) {
                                writejmps(id);
                                ij = dx[id].ijmp = 0;
                                dx[id].offset = offset;
                                offset += sizeof(struct jmp) + sizeof(offset);
                        }
                }
                dx[id].jp.n[ij] = ndelx;
                dx[id].jp.x[ij] = xx;
                dx[id].score = delx;
        }
        else {
                col1[yy] = dely[yy];
                ij = dx[id].ijmp;
if (dx[id].jp.n[0] && (!dna || (ndely[yy] >= MAXJMP
                    && xx > dx[id].jp.x[ij]+MX) || mis > dx[id].score+DINS0)) {
                        dx[id].ijmp++;
                        if (++ij >= MAXJMP) {
                                writejmps(id);
                                ij = dx[id].ijmp = 0;
                                dx[id].offset = offset;
                                offset += sizeof(struct jmp) + sizeof(offset);
                        }
                }
                dx[id].jp.n[ij] = -ndely[yy];
                dx[id].jp.x[ij] = xx;
                dx[id].score = dely[yy];
        }
        if (xx == len0 && yy < len1) {
                /* last col
                 */
                if (endgaps)
                        col1[yy] -= ins0+ins1*(len1-yy);
                if (col1[yy] > smax) {
                        smax = col1[yy];
                        dmax = id;
                }
        }
    }
    if (endgaps && xx < len0)
            col1[yy-1] -= ins0+ins1*(len0-xx);
    if (col1[yy-1] > smax) {
            smax = col1[yy-1];
            dmax = id;
    }
    tmp = col0; col0 = col1; col1 = tmp;
  }
  (void) free((char *)ndely);
  (void) free((char *)dely);
  (void) free((char *)col0);
  (void) free((char *)col1);                          }
/*
 *
 * print( ) -- only routine visible outside this module
```

TABLE 1-continued

```
*
* static:
* getmat( ) -- trace back best path, count matches: print( )
* pr_align( ) -- print alignment of described in array p[ ]: print( )
* dumpblock( ) -- dump a block of lines with numbers, stars: pr_align( )
* nums( ) -- put out a number line: dumpblock( )
* putline( ) -- put out a line (name, [num], seq, [num]): dumpblock( )
* stars( ) - -put a line of stars: dumpblock( )
* stripname( ) -- strip any path and prefix from a seqname
*/
#include "nw.h"
#define SPC        3
#define P_LINE     256      /* maximum output line */
#define P_SPC      3        /* space between name or num and seq */
extern    _day[26][26];
int       olen;             /* set output line length */
FILE      *fx;              /* output file */
print( )                                                                       print
{
        int     lx, ly, firstgap, lastgap;    /* overlap */
        if ((fx = fopen(ofile, "w")) == 0) {
                fprintf(stderr,"%s: can't write %s\n", prog, ofile);
                cleanup(1);
        }
        fprintf(fx, "<first sequence: %s (length = %d)\n", namex[0], len0);
        fprintf(fx, "<second sequence: %s (length = %d)\n", namex[1], len1);
        olen = 60;
        lx = len0;
        ly = len1;
        firstgap = lastgap = 0;
        if (dmax < len1 - 1) {          /* leading gap in x */
                pp[0].spc = firstgap = len1 - dmax - 1;
                ly -= pp[0].spc;
        }
        else if (dmax > len1 - 1) {    /* leading gap in y */
                pp[1].spc = firstgap = dmax - (len1 - 1);
                lx -= pp[1].spc;
        }
        if (dmax0 < len0 - 1) {        /* trailing gap in x */
                lastgap = len0 - dmax0 -1;
                lx -= lastgap;
        }
        else if (dmax0 > len0 - 1) {   /* trailing gap in y */
                lastgap = dmax0 - (len0 - 1);
                ly -= lastgap;
        }
        getmat(lx, ly, firstgap, lastgap);
        pr_align( );
}
/*
* trace back the best path, count matches
*/
static
getmat(lx, ly, firstgap, lastgap)                                              getmat
        int     lx, ly;                       /* "core" (minus endgaps) */
        int     firstgap, lastgap;            /* leading trailing overlap */
{
        int             nm, i0, i1, siz0, siz1;
        char            outx[32];
        double          pct;
        register        n0, n1;
        register char   *p0, *p1;
        /* get total matches, score
         */
        i0 = i1 = siz0 = siz1 = 0;
        p0 = seqx[0] + pp[1].spc;
        p1 = seqx[1] + pp[0].spc;
        n0 = pp[1].spc + 1;
        n1 = pp[0].spc + 1;
        nm = 0;
        while ( *p0 && *p1 ) {
                if (siz0) {
                        p1++;
                        n1++;
                        siz0--;
                }
                else if (siz1) {
                        p0++;
                        n0++;
                        siz1--;
```

TABLE 1-continued

```
                }
                else {
                        if (xbm[*p0-'A']&xbm[*p1-'A'])
                                nm++;
                        if (n0++ == pp[0].x[i0])
                                siz0 = pp[0].n[i0++];
                        if (n1++ == pp[1].x[i1])
                                siz1 = pp[1].n[i1++];
                        p0++;
                        p1++;
                }
        }
        /* pct homology:
         * if penalizing endgaps, base is the shorter seq
         * else, knock off overhangs and take shorter core
         */
        if (endgaps)
                lx = (len0 < len1)? len0 : len1;
        else
                lx = (lx < ly)? lx : ly;
        pct = 100.*(double)nm/(double)lx;
        fprintf(fx, "\n");
        fprintf(fx, "<%d match%s in an overlap of %d: %.2f percent similarity\n",
                nm, (nm == 1)? "" : "es", lx, pct);
        fprintf(fx, "<gaps in first sequence: %d", gapx);                       ...getmat
        if (gapx) {
                (void) sprintf(outx, " (%d %s%s)",
                        ngapx, (dna)? "base":"residue", (ngapx == 1)? "":"s");
                fprintf(fx,"%s", outx);
        fprintf(fx, ", gaps in second sequence: %d", gapy);
        if (gapy) {
                (void) sprintf(outx, " (%d %s%s)",
                        ngapy, (dna)? "base":"residue", (ngapy == 1)? "":"s");
                fprintf(fx,"%s", outx);
        }
        if (dna)
                fprintf(fx,
                "\n<score: %d (match = %d, mismatch = %d, gap penalty = %d + %d per base)\n",
                smax, DMAT, DMIS, DINS0, DINS1);
        else
                fprintf(fx,
                "\n<score: %d (Dayhoff PAM 250 matrix, gap penalty = %d + %d per residue)\n",
                smax, PINS0, PINS1);
        if (endgaps)
                fprintf(fx,
                "<endgaps penalized. left endgap: %d %s%s, right endgap: %d %s%s\n",
                firstgap, (dna)? "base" : "residue", (firstgap == 1)? "" : "s",
                lastgap, (dna)? "base" : "residue", (lastgap == 1)? "" : "s");
        else
                fprintf(fx, "<endgaps not penalized\n");
}
static          nm;             /* matches in core -- for checking */
static          lmax;           /* lengths of stripped file names */
static          ij[2];          /* jmp index for a path */
static          nc[2];          /* number at start of current line */
static          ni[2];          /* current elem number -- for gapping */
static          siz[2];
static char     *ps[2];         /* ptr to current element */
static char     *po[2];         /* ptr to next output char slot */
static char     out[2][P_LINE]; /* output line */
static char     star[P_LINE];   /* set by stars( ) */
/*
 * print alignment of described in struct path pp[ ]
 */
static
pr_align( )                                                                     pr_align
{
        int             nn;     /* char count */
        int             more;
        register        i;
        for (i = 0, lmax = 0; i < 2; i++) {
                nn = stripname(namex[i]);
                if (nn > lmax)
                        lmax = nn;
                nc[i] = 1;
                ni[i] = 1;
                siz[i] = ij[i] = 0;
                ps[i] = seqx[i];
                po[i] = out[i];                 }
        for (nn = nm = 0, more = 1; more; ) {                                   ...pr_align
```

TABLE 1-continued

```
        for (i = more = 0; i < 2; i++) {
                /*
                 * do we have more of this sequence?
                 */
                if (!*ps[i])
                        continue;
                more++;
                if (pp[i].spc) {        /* leading space */
                        *po[i]++ = ' ';
                        pp[i].spc--;
                }
                else if (siz[i]) {      /* in a gap */
                        *po[i]++ = '-';
                        siz[i]--;
                }
                else {                  /* we're putting a seq element
                                         */
                        *po[i] = *ps[i];
                        if (islower(*ps[i]))
                                *ps[i] = toupper(*ps[i]);
                        po[i]++;
                        ps[i]++;
                        /*
                         * are we at next gap for this seq?
                         */
                        if (ni[i] == pp[i].x[ij[i]]) {
                                /*
                                 * we need to merge all gaps
                                 * at this location
                                 */
                                siz[i] = pp[i].n[ij[i]++];
                                while (ni[i] == pp[i].x[ij[i]])
                                        siz[i] += pp[i].n[ij[i]++];
                        }
                        ni[i]++;
                }
        }
        if (++nn == olen || !more && nn) {
                dumpblock( );
                for (i = 0; i < 2; i++)
                        po[i] = out[i];
                nn = 0;
        }
        }
}
/*
 * dump a block of lines, including numbers, stars: pr__align( )
 */
static
dumpblock( )                                                            dumpblock
{
        register i;
        for (i = 0; i < 2; i++)
*po[i]-- = '\0';                                                        ...dumpblock (void) putc('\n', fx);
        for (i = 0; i < 2; i++) {
                if (*out[i] && (*out[i] != ' ' || *(po[i]) != ' ')) {
                        if (i == 0)
                                nums(i);
                        if (i == 0 && *out[1])
                                stars( );
                        putline(i);
                        if (i == 0 && *out[1])
                                fprintf(fx, star);
                        if (i == 1)
                                nums(i);
                }
        }
}
/*
 * put out a number line: dumpblock( )
 */
static
nums(ix)                                                                nums
        int     ix;     /* index in out[ ] holding seq line */
{
        char            nline[P__LINE];
        register        i, j;
        register char   *pn, *px, *py;
```

TABLE 1-continued

```
            for (pn = nline, i = 0; i < lmax+P_SPC; i++, pn++)
                    *pn = ' ';
            for (i = nc[ix], py = out[ix]; *py; py++, pn++) {
                    if (*py == ' ' || *py == '-')
                            *pn = ' ';
                    else {
                            if (i%10 == 0 || (i == 1 && nc[ix] != 1)) {
                                    j = (i < 0)? -i : i;
                                    for (px = pn; j; j /= 10, px--)
                                            *px = j%10 + '0';
                                    if (i < 0)
                                            *px = '-';
                            }
                            else
                                    *pn = ' ';
                            i++;
                    }
            }
            *pn = '\0';
            nc[ix] = i;
            for (pn = nline; *pn; pn++)
                    (void) putc(*pn, fx);
            (void) putc('\n', fx);
    }
    /*
    * put out a line (name, [num], seq, [num]): dumpblock( )
    */
    static                                                                          putline
    putline(ix)
            int     ix;                             {                               ...putline
            int     i;
            register char   *px;
            for (px = namex[ix], i = 0; *px && *px != ':'; px++, i++)
                    (void) putc(*px, fx);
            for (; i < lmax+P_SPC; i++)
                    (void) putc(' ', fx);
            /* these count from 1:
            * ni[ ] is current element (from 1)
            * nc[ ] is number at start of current line
            */
            for (px = out[ix]; *px; px++)
                    (void) putc(*px&0x7F, fx);
            (void) putc('\n', fx);
    }
    /*
    * put a line of stars (seqs always in out[0], out[1]): dumpblock( )
    */
    static                                                                          stars
    stars( )
    {
            int     i;
            register char   *p0, *p1, cx, *px;
            if (!*out[0] || (*out[0] == ' ' && *(po[0]) == ' ') ||
              !*out[1] || (*out[1] == ' ' && *(po[1]) == ' '))
                    return;
            px = star;
            for (i = lmax+P_SPC; i; i--)
                    *px++ = ' ';
            for (p0 = out[0], p1 = out[1]; *p0 && *p1; p0++, p1++) {
                    if (isalpha(*p0) && isalpha(*p1)) {
                            if (xbm[*p0-'A']&xbm[*p1-'A']) {
                                    cx = '*';
                                    nm++;
                            }
                            else if (!dna && __day[*p0-'A'][*p1-'A'] > 0)
                                    cx = '.';
                            else
                                    cx = ' ';
                    }
                    else
                            cx = ' ';
                    *px++ = cx;
            }
            *px++ = '\n';
            *px = '\0';
    }
    /*
    * strip path or prefix from pn, return len: pr_align( )
    */
```

TABLE 1-continued

```
static
stripname(pn)                                                                       stripname
        char        *pn;      /* file name (may be path) */
{
        register char       *px, *py;
        py = 0;
        for (px = pn; *px; px++)
                if (*px == '/')
                        py = px + 1;
        if (py)
                (void) strcpy(pn, py);
        return(strlen(pn));
}
/*
* cleanup( ) -- cleanup any tmp file
* getseq( ) -- read in seq, set dna, len, maxlen
* g_calloc( ) -- calloc( ) with error checkin
* readjmps( ) -- get the good jmps, from tmp file if necessary
* writejmps( ) -- write a filled array of jmps to a tmp file: nw( )
*/
#include "nw.h"
#include <sys/file.h>
char      *jname = "/tmp/homgXXXXXX";         /* tmp file for jmps */
FILE      *fj;
int       cleanup( );                          /* cleanup tmp file */
long      lseek( );
/*
* remove any tmp file if we blow
*/
cleanup(i)                                                                          cleanup
        int         i;
{
        if (fj)
                (void) unlink(jname);
        exit(i);
}
/*
* read, return ptr to seq, set dna, len, maxlen
* skip lines starting with ';', '<', or '>'
* seq in upper or lower case
*/
char      *
getseq(file, len)                                                                   getseq
        char        *file;    /* file name */
        int         *len;     /* seq len */
{
        char               line[1024], *pseq;
        register char      *px, *py;
        int                natgc, tlen;
        FILE               *fp;
        if ((fp = fopen(file,"r")) == 0) {
                fprintf(stderr,"%s: can't read %s\n", prog, file);
                exit(1);
        }
        tlen = natgc = 0;
        while (fgets(line, 1024, fp)) {
                if (*line == ';' || *line == '<' || *line == '>')
                        continue;
                for (px = line; *px != '\n'; px++)
                        if (isupper(*px) || islower(*px))
                                tlen++;
        }
        if ((pseq = malloc((unsigned)(tlen+6))) == 0) {
                fprintf(stderr,"%s: malloc( ) failed to get %d bytes for %s\n", prog, tlen+6, file);
                exit(1);
        }
        pseq[0] = pseq[1] = pseq[2] = pseq[3] = '\0';
                                                                                    ...getseq
        py = pseq + 4;
        *len = tlen;
        rewind(fp);
        while (fgets(line, 1024, fp)) {
                if (*line == ';' || *line == '<' || *line == '>')
                        continue;
                for (px = line; *px != '\n'; px++) {
                        if (isupper(*px))
                                *py++ = *px;
                        else if (islower(*px))
                                *py++ = toupper(*px);
                        if (index("ATGCU",*(py-1)))
```

TABLE 1-continued

```
                        natgc++;
                }
        }
        *py++ = '\0';
        *py = '\0';
        (void) fclose(fp);
        dna = natgc > (tlen/3);
        return(pseq+4);
}
char    *
g_calloc(msg, nx, sz)                                                                   g_calloc
        char            *msg;           /* program, calling routine */
        int             nx, sz;         /* number and size of elements */
{
        char                    *px, *calloc( );
        if ((px = calloc((unsigned)nx, (unsigned)sz)) == 0) {
                if (*msg) {
                        fprintf(stderr, "%s: g_calloc( ) failed %s (n=%d, sz=%d)\n", prog, msg,
nx, sz);
                        exit(1);
                }
        }
        return(px);
}
/*
 * get final jmps from dx[ ] or tmp file, set pp[ ], reset dmax: main( )
 */
readjmps( )                                                                             readjmps
{
        int             fd = -1;
        int             siz, i0, i1;
        register i, j, xx;
        if (fj) {
                (void) fclose(fj);
                if ((fd = open(jname, O_RDONLY, 0)) < 0) {
                        fprintf(stderr, "%s: can't open( ) %s\n", prog, jname);
                        cleanup(1);
                }
        }
        for (i = i0 = i1 = 0, dmax0 = dmax, xx = len0; ; i++) {
                while (1) {
                        for (j = dx[dmax].ijmp; j >= 0 && dx[dmax].jp.x[j] >= xx; j--)
                                ;
                                                                                        ...readjmps
                        if (j < 0 && dx[dmax].offset && fj) {
                                (void) lseek(fd, dx[dmax].offset, 0);
                                (void) read(fd, (char *)&dx[dmax].jp, sizeof(struct jmp));
                                (void) read(fd, (char *)&dx[dmax].offset,
sizeof(dx[dmax].offset));
                                dx[dmax].ijmp = MAXJMP-1;
                        }
                        else
                                break;
                }
                if (i >= JMPS) {
                        fprintf(stderr, "%s: too many gaps in alignment\n", prog);
                        cleanup(1);
                }
                if (j >= 0) {
                        siz = dx[dmax].jp.n[j];
                        xx = dx[dmax].jp.x[j];
                        dmax += siz;
                        if (siz < 0) {                  /* gap in second seq */
                                pp[1].n[i1] = -siz;
                                xx += siz;
                                /* id = xx - yy + len1 - 1
                                 */
                                pp[1].x[i1] = xx - dmax + len1 - 1;
                                gapy++;
                                ngapy -= siz;
/* ignore MAXGAP when doing endgaps */
                                siz = (-siz < MAXGAP || endgaps)? -siz : MAXGAP;
                                i1++;
                        }
                        else if (siz > 0) {             /* gap in first seq */
                                pp[0].n[i0] = siz;
                                pp[0].x[i0] = xx;
                                gapx++;
                                ngapx += siz;
/* ignore MAXGAP when doing endgaps */
```

TABLE 1-continued

```
                    siz = (siz < MAXGAP || endgaps)? siz : MAXGAP;
                    i0++;
                }
            }
            else
                    break;
        }
        /* reverse the order of jmps
        */
        for (j = 0, i0--; j < i0; j++, i0--) {
            i = pp[0].n[j]; pp[0].n[j] = pp[0].n[i0]; pp[0].n[i0] = i;
            i = pp[0].x[j]; pp[0].x[j] = pp[0].x[i0]; pp[0].x[i0] = i;
        }
        for (j = 0, i1--; j < i1; j++, i1--) {
            i = pp[1].n[j]; pp[1].n[j] = pp[1].n[i1]; pp[1].n[i1] = i;
            i = pp[1].x[j]; pp[1].x[j] = pp[1].x[i1]; pp[1].x[i1] = i;
        }
        if (fd >= 0)
                    (void) close(fd);
        if (fj) {
                    (void) unlink(jname);
                    fj = 0;
                    offset = 0;              }              }
/*
* write a filled jmp struct offset of the prev one (if any): nw( )
*/
writejmps(ix)                                                              writejmps
        int     ix;
{
        char    *mktemp( );
        if (!fj) {
                if (mktemp(jname) < 0) {
                        fprintf(stderr, "%s: can't mktemp( ) %s\n", prog, jname);
                        cleanup(1);
                }
                if ((fj = fopen(jname, "w")) == 0) {
                        fprintf(stderr, "%s: can't write %s\n", prog, jname);
                        exit(1);
                }
        }
        (void) fwrite((char *)&dx[ix].jp, sizeof(struct jmp), 1, fj);
        (void) fwrite((char *)&dx[ix].offset, sizeof(dx[ix].offset), 1, fj);
```

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y wherein X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations using this method, Tables 2 and 3 demonstrate how to calculate the % amino acid sequence identity of the amino acid sequence designated "Comparison Protein" to the amino acid sequence designated "BCMA", wherein "BCMA" represents the amino acid sequence of polypeptide of interest, "Comparison Protein" represents the amino acid sequence of a polypeptide against which the "BCMA" polypeptide of interest is being compared, and "X", "Y" and "Z" each represent different hypothetical amino acid residues. Unless specifically stated otherwise, all % amino acid sequence identity values used herein are obtained as described in the immediately preceding paragraph using the ALIGN-2 computer program.

TABLE 2

| BCMA | XXXXXXXXXXXXXXX | (Length = 15 amino acids) |
|---|---|---|
| Comparison Protein | XXXXXYYYYYYY | (Length = 12 amino acids) |

% amino acid sequence identity = (the number of identically matching amino acid residues between the two polypeptide sequences as determined by ALIGN-2) divided by (the total number of amino acid residues of the BCMA polypeptide) = 5 divided by 15 = 33.3%.

TABLE 3

| BCMA | XXXXXXXXXX | (Length = 10 amino acids) |
|---|---|---|
| Comparison Protein | XXXXXYYYYYYZZYZ | (Length = 15 amino acids) |

% amino acid sequence identity = (the number of identically matching amino acid residues between the two polypeptide sequences as determined by ALIGN-2) divided by (the total number of amino acid residues of the BCMA polypeptide) = 5 divided by 10 = 50%.

A "native" or "native sequence" polypeptide according to this invention is a polypeptide which has an amino acid sequence that is the same as an amino acid sequence from a polypeptide from nature. Such native polypeptide can be isolated from nature or be produced by recombinant or synthetic means.

A BCMA "variant" or "mutant" according to this invention is derived from all or a portion of a native BCMA ECD amino acid sequence, but does not comprise the exact CRD sequence of the native BCMA polypeptide. According to one embodiment, the BCMA variant contains the same number and relative positions of cysteines of the CRD of a native BCMA. According to another embodiment, a BCMA variant is a polypeptide that has a decreased affinity for BAFF as compared to a native BCMA or an ECD of a native BCMA (e.g., by mutating any one or all of residues corresponding to F14, I22 or Q25 of FIG. 5, optionally substituting with alanine). According to another embodiment, a BCMA variant is a polypeptide that has a decreased affinity for APRIL as compared to a native BCMA or an ECD of a native BCMA (e.g., by mutating any one or all of residues corresponding to R27 and Y13 of FIG. 5, optionally substituting with alanine). According to another embodiment, a BCMA variant is a polypeptide that has a decreased affinity for APRIL and BAFF as compared to a native BCMA or an ECD of a native BCMA (e.g., by mutating any one or all of residues corresponding to D15, L18 and L17 of FIG. 5, optionally substituting with alanine). In one preferred embodiment of this invention, the BCMA variant is derived from a human BCMA. It should be understood that BCMA variants according to this invention includes soluble polypeptides, for example, polypeptides lacking the BCMA transmembrane region.

Alteration(s) to a polypeptide can be made by chemically or physically changing amino acid residue(s) as compared to the unaltered form of the polypeptide, for example, by substitution with other amino acid residue(s), other mutation such as deletion of residue(s), or chemical addition or modification of residue(s). Recombinant nucleic acid methods are useful for altering polypeptides so that the polypeptide expressed from the engineered nucleic acid molecule contains the alteration (e.g., substitution and deletion of residues). Alterations of a residue can also be achieved by direct change to a polynucleotide of interest, e.g., by chemical reaction with amino acid residue(s). It should be understood that a polypeptide of this invention can have additional alterations, other than those alterations specifically disclosed herein, as compared to a native sequence BCMA.

A BCMA "extracellular domain" or "ECD" refers to a form of the BCMA polypeptide which is essentially free of the BCMA transmembrane and cytoplasmic domains. Examples of ECD of BCMA include residues 1-52 (SEQ ID NO:21) or 5-51 of the human BCMA described in FIG. 5.

A soluble polypeptide according to this invention (example soluble BCMA) is a polypeptide that is soluble in water and lacks appreciable affinity for lipids. A soluble BCMA polypeptide can be made, e.g., by removing the transmembrane domain of BCMA and optionally removing the cytoplasmic domain.

It should be understood that a multimer according to this invention refers to a numerical value indicating two or more polypeptides of this invention. In one preferred embodiment, the multimer is an n-mer, wherein n is 3-10 polypeptides. According to another embodiment, a multimeric complex of polypeptides according to this invention are substantially free of n-mers with values greater than 10 and/or a molecular weight of greater than two million daltons.

The BAFF polypeptide signaling promotes, among other things, B cell survival and B cell maturation. The inhibition, blockage or neutralization of BAFF signaling results in, among other things, the partial or full block, inhibition, or neutralization of one or more biological activities of a BAFF polypeptide, in vitro or in vivo. Biologically active BAFF can potentiate any one or combination of the following events: an increased survival of B cells, an increased level of IgG and/or IgM, an increased numbers of plasma cells, and processing of NF-κb2/100 to p 52 NF-κb in splenic B cells (e.g., Batten, M et al., (2000) *J. Exp. Med.* 192:1453-1465; Moore, et al., (1999) *Science* 285:260-263; Kayagaki, et al., *Immunity* (2002) 10:515-524).

Inhibition, blockage or neutralization of APRIL signaling can be identified by using any one or combination of methods known in the art. For example, an inhibitor can partially or fully block, inhibit, or neutralize (1) costimulation of primary B and T cells by APRIL in vitro or (2) stimulation of IgM production from peripheral blood B cells by APRIL (Yu, G., et al., (2000) *Nat. Immunol.* 1:252-256; Marsters, S. A., et al., (200) *Curr. Biol.* 10:785-788). In another example, an inhibitor can reduce the expansion of the B cell population and T cell activation after administration of APRIL in vivo (Yu, G., et al., (2000) *Nat. Immunol.* 1:252-256). In yet another example, an inhibitor can be tested for the reduction of the growth of a tumor implanted into mice after administration with the inhibitor (Rennert, P., et al. (2000) *J. Exp. Med.* 192:1677-1683).

The term "BLyS," "BLyS polypeptide," or "BAFF" specifically encompasses naturally-occurring full-length, truncated, secreted and soluble forms (e.g., an extracellular domain sequence) of mammalian BAFF, naturally-occurring variant forms (e.g., alternatively spliced forms), naturally-occurring allelic variants of mammalian BAFF and recombinantly expressed full-length, truncated, secreted and soluble forms of BAFF having an amino acid sequence of a naturally-occurring BAFF.

Examples of "BAFF polypeptides" are shown below:

```
Human BAFF sequence
                                            (SEQ ID NO: 23)
MDDSTEREQS RLTSCLKKRE EMKLKECVSI LPRKESPSVR

SSKDGKLLAA TLLLALLSCC LTVVSFYQVA ALQGDLASLR

AELQGHHAEK LPAGAGAPKA GLEEAPAVTA GLKIFEPPAP

GEGNSSQNSR NKRAVQGPEE TVTQDCLQLI ADSETPTIQK

GSYTFVPWLL SFKRGSALEE KENKILVKET GYFFIYGQVL

YTDKTYAMGH LIQRKKVHVF GDELSLVTLF RCIQNMPETL

PNNSCYSAGI AKLEEGDELQ LAIPRENAQI SLDGDVTFFG

ALKLL

Mouse BAFF sequence
                                            (SEQ ID NO: 24)
MDESAKTLPP PCLCFCSEKG EDMKVGYDPI TPQKEEGAWF

GICRDGRLLA ATLLLALLSS SFTAMSLYQL AALQADLMNL

RMELQSYRGS ATPAAAGAPE LTAGVKLLTP AAPRPHNSSR

GHRNRRAFQG PEETEQDVDL SAPPAPCLPG CRHSQHDDNG

MNLRNIIQDC LQLIADSDTP TIRKGTYTFV PWLLSFKRGN

ALEEKENKIV VRQTGYFFIY SQVLYTDPIF AMGHVIQRKK

VHVFGDELSL VTLFRCIQNM PKTLPNNSCY SAGIARLEEG

DEIQLAIPRE NAQISRNGDD TFFGALKLL
```

The term "APRIL polypeptide," "APRIL," and "APRIL protein" specifically encompasses naturally-occurring full-length, truncated, secreted and soluble forms (e.g., an extracellular domain sequence) of mammalian APRIL, naturally-occurring variant forms (e.g., alternatively spliced forms), naturally-occurring allelic variants of mammalian APRIL and recombinantly expressed full-length, truncated, secreted and soluble forms of APRIL having an amino acid sequence of a naturally-occurring APRIL. The term "APRIL" includes those polypeptides described in Hahne et al., *J. Exp. Med.*, 188:1185-1190 (1998); GenBank Accession No. AF046888; WO 99/00518 published Jan. 7, 1999; WO 99/12965 published Mar. 18, 1999; WO 99/33980 published Jul. 8, 1999; WO 97/33902 published Sep. 18, 1997; WO 99/11791 published Mar. 11, 1999; EP 911,633 published Mar. 28, 1999; and WO 99/50416 published Oct. 7, 1999.

Examples of APRIL polypeptides are shown below:

```
Human APRIL sequence
                                        (SEQ ID NO: 25)
MPASSPFLLAPKGPPGNMGGPVREPALSVALWLSWGAALGAVACAMALLT

QQTELQSLRREVSRLQGTGGPSQNGEGYPWQSLPEQSSDALEAWENGERS

RKRRAVLTQKQKKQHSVLHLVPINATSKDDSDVTEVMWQPALRRGRGLQA

QGYGVRIQDAGVYLLYSQVLFQDVTFTMGQVVSREGQGRQETLFRCIRSM

PSHPDRAYNSCYSAGVFHLHQGDILSVIIPRARAKLNLSPHGTFLGFVKL

Mouse APRIL sequence
                                        (SEQ ID NO: 26)
MPASSPGHMGGSVREPALSVALWLSWGAVLGAVTCAVALLIQQTELQSLR

REVSRLQRSGGPSQKQGERPWQSLWEQSPDVLEAWKDGAKSRRRRAVLTQ

KHKKKHSVLHLVPVNITSKDSDVTEVMWQPVLRRGRGLEAQGDIVRVWDT

GIYLLYSQVLFHDVTFTMGQVVSREGQGRRETLFRCIRSMPSDPDRAYNS

CYSAGVFHLHQGDIITVKIPRANAKLSLSPHGTFLGFVKL
```

According to one embodiment, an inhibitor according this invention is a "small" molecule or a "small organic" molecule that is 1500 daltons or less.

The term "antibody" is used in the broadest sense and specifically covers, for example, monoclonal antibodies, polyclonal antibodies, antibodies with polyepitopic specificity, single chain antibodies, and fragments of antibodies. According to one embodiment, a polypeptide of this invention is fused into an antibody framework, for example, in the variable region or in a CDR such that the antibody can bind to and inhibit a ligand binding to its receptor. The antibodies comprising a polypeptide of this invention can be chimeric, humanized, or human. The antibodies comprising a polypeptide of this invention can be an antibody fragment. Antibodies and methods of generating them are described in more detail below.

The term "monoclonal antibody" as used herein refers to an antibody obtained from a population of substantially homogeneous antibodies, i.e., the individual antibodies comprising the population are identical except for possible naturally occurring mutations that can be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by recombinant DNA methods (see, e.g., U.S. Pat. No. 4,816,567). The "monoclonal antibodies" can also be isolated from phage antibody libraries using the techniques described in Clackson et al., *Nature*, 352:624-628 (1991) and Marks et al., *J. Mol. Biol.*, 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA*, 81:6851-6855 (1984)). Methods of making chimeric antibodies are known in the art.

"Humanized" forms of non-human antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies are human immunoglobulins (recipient antibody) in which residues from a complementarity-determining region (CDR) of the recipient are replaced by residues from a CDR of a non-human species (donor antibody) such as mouse, rat or rabbit or another source having the desired specificity, affinity, and capacity. In some instances, Fv framework region (FR) residues of the human immunoglobulin are replaced by corresponding non-human residues. Furthermore, humanized antibodies can comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., *Nature*, 321:522-525 (1986); Reichmann et al., *Nature*, 332:323-329 (1988); and Presta, L., *Curr. Op. Struct. Biol.*, 2:593-596 (1992). Methods of making humanized antibodies are known in the art.

Human antibodies can also be produced using various techniques known in the art, including phage-display libraries. Hoogenboom and Winter, *J. Mot. Biol.*, 227:381 (1991); Marks et al., *J. Mol. Biol.*, 222:581 (1991). The techniques of Cole et al. and Boerner et al., are also available for the preparation of human monoclonal antibodies. Cole et al., *Monoclonal Antibodies and Cancer Therapy*, Alan R. Liss, p. 77 (1985); Boerner et al., *J. Immunol.*, 147(1):86-95 (1991).

A "composition" of this invention comprises a polypeptide of this invention, optionally in combination with a pharmaceutically acceptable carrier. The composition can further comprise an additional therapeutic agent to treat the indication intended. In one embodiment, the composition comprises a second therapeutic agent selected from a drug for treating an immune-related disease and a drug for treating a cancer. In another embodiment, the drug for treating a cancer is selected from the group consisting of a cytotoxic agent, a chemotherapeutic agent, a growth inhibiting agent and a chemotherapeutic agent.

"Carriers" as used herein include pharmaceutically acceptable carriers, excipients, or stabilizers which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The word "label" or "detection agent" when used herein refers to a detectable compound or composition which is conjugated directly or indirectly to the polypeptide, antibody, antagonist or composition so as to generate a "labeled" a polypeptide, antibody, antagonist or composition. The label can be detectable by itself (e.g. radioisotope labels or fluorescent labels) or, in the case of an enzymatic label, can catalyze chemical alteration of a substrate compound or composition which is detectable (e.g., by FRET).

Various tag polypeptides and their respective antibodies are well known in the art. Tagged polypeptides and antibodies of this invention are contemplated. Examples include poly-histidine (poly-his) or poly-histidine-glycine (poly-his-gly) tags; the flu HA tag polypeptide and its antibody 12CA5 [Field et al., *Mol. Cell. Biol.*, 8:2159-2165 (1988)]; the c-myc tag and the 8F9, 3C7, 6E10, G4, B7 and 9E10 antibodies thereto [Evan et al., *Molecular and Cellular Biology*, 5:3610-3616 (1985)]; and the Herpes Simplex virus glycoprotein D (gD) tag and its antibody [Paborsky et al., *Protein Engineering*, 3(6):547-553 (1990)]. The FLAG-peptide [Hopp et al., *BioTechnology*, 6:1204-1210 (1988)] is recognized by an anti-FLAG M2 monoclonal antibody (Eastman Kodak Co., New Haven, Conn.). Purification of a protein containing the FLAG peptide can be performed by immunoaffinity chromatography using an affinity matrix comprising the anti-FLAG M2 monoclonal antibody covalently attached to agarose (Eastman Kodak Co., New Haven, Conn.). Other tag polypeptides include the KT3 epitope peptide [Martin et al., *Science*, 255:192-194 (1992)]; an α-tubulin epitope peptide [Skinner et al., *J. Biol. Chem.*, 266:15163-15166 (1991)]; and the T7 gene 10 protein peptide tag [Lutz-Freyermuth et al., *Proc. Natl. Acad. Sci USA*, 87:6393-6397 (1990)].

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below.

A "chemotherapeutic agent" is a chemical compound useful in the treatment of cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhône-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above. esperamicins (see U.S. Pat. No. 4,675,187), melphalan and other related nitrogen mustards. Also included in this definition are hormonal agents that act to regulate or inhibit hormone action such as tamoxifen and onapristone.

A "growth inhibitory agent" when used herein refers to a compound or composition which inhibits growth of a cell, either in vitro or in vivo. Examples of growth inhibitory agents include agents that block cell cycle progression (at a place other than S phase), such as agents that induce G1 arrest and M-phase arrest. Classical M-phase blockers include the vincas (vincristine and vinblastine), taxol, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds. Chapter 1, entitled "Cell cycle regulation, oncogens, and antineoplastic drugs" by Murakami et al. (WB Saunders: Philadelphia, 1995), especially p. 13.

"Isolated," when used to describe the various proteins disclosed herein, means protein that has been identified and separated and/or recovered away from a component of its natural environment. Contaminant components of its natural environment are materials that would typically interfere with diagnostic or therapeutic uses for the protein, and may include enzymes, hormones, and other proteinaceous or non-proteinaceous solutes. In preferred embodiments, the protein will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated protein includes protein in situ within recombinant cells, since at least one component of the protein natural environment will not be present. Ordinarily, however, isolated protein will be prepared by at least one purification step.

A "heterologous" component refers to a component that is introduced into or produced within a different entity from that in which it is naturally located. For example, a polynucleotide derived from one organism and introduced by genetic engineering techniques into a different organism is a heterologous polynucleotide which, if expressed, can encode a heterologous polypeptide. Similarly, a promoter or enhance that is removed from its native coding sequence and operably linked to a different coding sequence is a heterologous promoter or enhancer. Similarly, a non-BCMA polypeptide sequence that is fused to a BCMA polypeptide is a heterologous protein sequence.

"Mammal" for purposes of treatment or therapy refers to any animal classified as a mammal, including humans, domestic and farm animals, and zoo, sports, or pet animals, such as dogs, horses, cats, cows, etc. Preferably, the mammal is human.

The term "therapeutically effective amount" refers to an amount of a composition of this invention effective to "alleviate" or "treat" a disease or disorder in a subject or mammal. Generally, alleviation of a disease or disorder involves the lessening of one or more symptoms or medical problems associated with the disease or disorder. In some embodiments, polypeptides and compositions of this invention can be used to prevent the onset or reoccurrence of the disease or disorder in a subject or mammal. For example, in a subject with autoimmune disease, a polypeptide of this invention can be used to prevent or alleviate flare-ups. In one embodiment, if the immune-disease to be treated is a B-cell mediate disease, it is an amount that results in the reduction in the number of B cells (B cell depletion) in the mammal. In the case of cancer, the therapeutically effective amount of the drug can reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic.

The terms "cancer", "cancerous", and "malignant" refer to or describe the physiological condition in mammals that is typically characterized by unregulated cell growth. Examples of cancer include but are not limited to, carcinoma including adenocarcinoma, lymphoma, blastoma, melanoma, sarcoma, and leukemia. More particular examples of such cancers include squamous cell cancer, small-cell lung cancer, non-small cell lung cancer, gastrointestinal cancer, Hodgkin's and non-Hodgkin's lymphoma, pancreatic cancer, glioblastoma, cervical cancer, ovarian cancer, liver cancer such as hepatic carcinoma and hepatoma, bladder cancer, breast cancer, colon cancer, colorectal cancer, endometrial carcinoma, salivary gland carcinoma, kidney cancer such as renal cell carcinoma and Wilms' tumors, basal cell carcinoma, melanoma, prostate cancer, vulval cancer, thyroid cancer, testicular cancer, esophageal cancer, and various types of head and neck cancer. Optionally, the cancer will express, or have associated with the cancer cell, increased BAFF, APRIL and/or BCMA levels. In one embodiment, the cancers for treatment herein include lymphoma, leukemia and myeloma, and subtypes thereof, such as Burkitt's lymphoma, multiple myeloma, acute lymphoblastic or lymphocytic leukemia, non-Hodgkin's and Hodgkin's lymphoma, and acute myeloid leukemia.

The term "immune related disease" means a disease in which a component of the immune system of a mammal causes, mediates or otherwise contributes to a morbidity in the mammal. Also included are diseases in which stimulation or intervention of the immune response has an ameliorative effect on progression of the disease. Included within this term are autoimmune diseases, immune-mediated inflammatory diseases, non-immune-mediated inflammatory diseases, infectious diseases, and immunodeficiency diseases. Examples of immune-related and inflammatory diseases, some of which are immune or T cell mediated, which can be treated according to the invention include 1, rheumatoid arthritis, juvenile chronic arthritis, spondyloarthropathies, systemic sclerosis (scleroderma), idiopathic inflammatory myopathies (dermatomyositis, polymyositis), Sjogren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barré syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory and fibrotic lung diseases such as inflammatory bowel disease (ulcerative colitis: Crohn's disease), gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonias, idiopathic pulmonary fibrosis and hypersensitivity pneumonitis, transplantation associated diseases including graft rejection and graft-versus-host-disease. Infectious diseases include AIDS (HIV infection), hepatitis A, B, C, D, and E, bacterial infections, fungal infections, protozoal infections and parasitic infections.

"Autoimmune disease" is used herein in a broad, general sense to refer to disorders or conditions in mammals in which destruction of normal or healthy tissue arises from humoral or cellular immune responses of the individual mammal to his or her own tissue constituents. Examples include, but are not limited to, lupus erythematous, thyroiditis, rheumatoid arthritis, psoriasis, multiple sclerosis, autoimmune diabetes, and inflammatory bowel disease (IBD).

As used herein, "B cell depletion" refers to a reduction in B cell levels in an animal or human after drug or antibody treatment, as compared to the level before treatment. B cell levels are measurable using well known assays such as by getting a complete blood count, by FACS analysis staining for known B cell markers, and by methods such as described in the Experimental Examples. B cell depletion can be partial or complete. In a patient receiving a B cell depleting drug, B cells are generally depleted for the duration of time when the drug is circulating in the patient's body and the time for recovery of B cells.

The term "T-cell mediated" disease means a disease in which T cells directly or indirectly mediate or otherwise contribute to the morbidity in a mammal. The T cell mediated disease by be associated with cell mediated effects, lymphokine mediated effects, etc. and even effects associated with B cells if the B cells are stimulated, for example, by the lymphokines secreted by T cells.

Methods and Materials

Generally, the methods of the invention for inhibiting BAFF or APRIL binding their receptors in mammalian cells comprise exposing the cells to a desired amount of a polypeptide of this invention which fully or partially blocks BAFF or APRIL interaction with their receptors. In one embodiment, the amount of polypeptide employed will be an amount effective to affect the binding and/or activity of BAFF or APRIL to achieve a therapeutic effect. This can be accomplished in vitro or in vivo in accordance, for instance, with the methods described below and in the Examples. Exemplary conditions or disorders to be treated with a polypeptide of this invention include conditions in mammals clinically referred to as autoimmune diseases, including but not limited to rheumatoid arthritis, multiple sclerosis, psoriasis, and lupus or other pathological conditions, including cancer and T-cell mediated diseases. Diagnostic methods are also provided herein. For instance, the polypeptides of the invention can be used to detect APRIL or BAFF in mammals or in vitro assays, including detection in mammals known to be or suspected of having a BAFF or APRIL-related pathological condition or expressing abnormal amounts of APRIL or BAFF (e.g., lupus patients and NZF/WF1 mice). According to one embodiment, polypeptides of this invention are used, e.g., in immunoassays to detect or quantitate BAFF or APRIL in a sample. According to another embodiment, a sample, such as cells obtained from a mammal, can be incubated in the presence of a labeled polypeptide of this invention, and detection of the labeled polypeptide is performed. Such assays, including various clinical assay procedures, are known in the art, for instance as described in Voller et al., *Immunoassays*, University Park, 1981.

A. Materials

According to one embodiment, the polypeptides of this invention are selected from the group consisting of covalently modified forms of the polypeptides (e.g., immunoadhesins, labeled polypeptides, protected polypeptides, conjugated polypeptides etc.). Various techniques that are employed for making these forms of polypeptides are described below. Methods for labeling polypeptides and conjugating molecules to polypeptides are known in the art.

Compositions of the invention can be prepared using recombinant techniques known in the art. The description below relates to methods of producing such polypeptides by culturing host cells transformed or transfected with a vector containing the encoding nucleic acid and recovering the polypeptide from the cell culture. (See, e.g., Sambrook et al., *Molecular Cloning: A Laboratory Manual* (New York: Cold Spring Harbor Laboratory Press, 1989); Dieffenbach et al., *PCR Primer: A Laboratory Manual* (Cold Spring Harbor Laboratory Press, 1995)).

The nucleic acid (e.g., cDNA or genomic DNA) encoding the desired polypeptide can be inserted into a replicable vector for further cloning (amplification of the DNA) or for expression. Various vectors are publicly available. The vector components generally include, but are not limited to, one or more of the following: a signal sequence, an origin of replication, one or more marker genes, an enhancer element, a promoter, and a transcription termination sequence, each of which is described below. Optional signal sequences, origins of replication, marker genes, enhancer elements and transcription terminator sequences that can be employed are known in the art and described in further detail in WO97/25428.

Expression and cloning vectors usually contain a promoter that is recognized by the host organism and is operably linked to the encoding nucleic acid sequence. Promoters are untranslated sequences located upstream (5') to the start codon of a structural gene (generally within about 100 to 1000 bp) that control the transcription and translation of a particular nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to the encoding DNA by removing the promoter from the source DNA by restriction enzyme digestion and inserting the isolated promoter sequence into the vector.

Promoters suitable for use with prokaryotic and eukaryotic hosts are known in the art. Construction of suitable vectors containing one or more of the above-listed components employs standard ligation techniques. Isolated plasmids or DNA fragments are cleaved, tailored, and religated in the form desired to generate the plasmids required. For analysis to confirm correct sequences in plasmids constructed, the ligation mixtures can be used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced using standard techniques known in the art. [See, e.g., Messing et al., *Nucleic Acids Res.*, 9:309 (1981); Maxam et al., *Methods in Enzymology*, 65:499 (1980)].

Expression vectors that provide for the transient expression in mammalian cells of the encoding DNA can be employed. In general, transient expression involves the use of an expression vector that is able to replicate efficiently in a host cell, such that the host cell accumulates many copies of the expression vector and, in turn, synthesizes high levels of a desired polypeptide encoded by the expression vector [Sambrook et al., supra]. Transient expression systems, comprising a suitable expression vector and a host cell, allow for the convenient positive identification of polypeptides encoded by cloned DNAs, as well as for the rapid screening of such polypeptides for desired biological or physiological properties.

Other methods, vectors, and host cells suitable for adaptation to the synthesis of the desired polypeptide in recombinant vertebrate cell culture are described in Gething et al., Nature, 293:620-625 (1981); Mantei et al., Nature, 281:40-46 (1979); EP 117,060; and EP 117,058.

Suitable host cells for cloning or expressing the DNA in the vectors herein include prokaryote, yeast, or higher eukaryote cells. Suitable prokaryotes for this purpose include but are not limited to eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. Preferably, the host cell secrete minimal amounts of proteolytic enzymes.

In addition to prokaryotes, eukaryotic microbes such as filamentous fungi or yeast are suitable cloning or expression hosts for vectors. Suitable host cells for the expression of glycosylated polypeptide are derived from multicellular organisms. Examples of all such host cells are described further in WO97/25428.

Host cells are transfected and preferably transformed with the above-described expression or cloning vectors and cultured in nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, CaPO4 and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., Gene, 23:315 (1983) and WO 89/05859 published 29 Jun. 1989. In addition, plants can be transfected using ultrasound treatment as described in WO 91/00358 published 10 Jan. 1991.

For mammalian cells without such cell walls, the calcium phosphate precipitation method of Graham and van der Eb, Virology, 52:456-457 (1978) can be employed. General aspects of mammalian cell host system transformations have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci.* (USA), 76:3829 (1979). However, other methods for introducing DNA into cells, such as by nuclear microinjection, electroporation, bacterial protoplast fusion with intact cells, or polycations, e.g., polybrene, polyornithine, can also be used. For various techniques for transforming mammalian cells, see Keown et al., *Methods in Enzymology*, 185:527-537 (1990) and Mansour et al., *Nature*, 336: 348-352 (1988).

Prokaryotic cells can be cultured in suitable culture media as described generally in Sambrook et al., supra. Examples of commercially available culture media include Ham's F10 (Sigma), Minimal Essential Medium ("MEM", Sigma), RPMI-1640 (Sigma), and Dulbecco's Modified Eagle's Medium ("DMEM", Sigma). Any such media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In general, principles, protocols, and practical techniques for maximizing the productivity of mammalian cell cultures can be found in *Mammalian Cell Biotechnology: A Practical Approach*, M. Butler, ed. (IRL Press, 1991).

The expressed polypeptides can be recovered from the culture medium as a secreted polypeptide, although may also be recovered from host cell lysates when directly produced without a secretory signal. If the polypeptide is membrane-bound, it can be released from the membrane using a suitable detergent solution (e.g. Triton-X 100) or its extracellular region can be released by enzymatic cleavage.

When the polypeptide is produced in a recombinant cell other than one of human origin, it is free of proteins or polypeptides of human origin. However, it is usually necessary to recover or purify the polypeptide from recombinant cell proteins or polypeptides to obtain preparations that are substantially homogeneous. As a first step, the culture medium or lysate may be centrifuged to remove particulate cell debris. The following are procedures exemplary of suitable purification procedures: by fractionation on an ion-exchange column; ethanol precipitation; hydrophobic interaction chromatography; reverse phase HPLC; chromatography on silica or on a cation-exchange resin such as DEAE; chromatofocusing; SDS-PAGE; ammonium sulfate precipitation; gel filtration using, for example, Sephadex G-75; and protein A Sepharose columns to remove contaminants such as IgG.

Variants according to this invention can be prepared by introducing appropriate nucleotide changes into the DNA, and/or by synthesis of the polypeptide (e.g., Kunkel mutagenesis). Those skilled in the art will appreciate that amino acid changes may alter post-translational processes of the polypeptide, such as changing the number or position of glycosylation sites or altering the membrane anchoring characteristics.

Variations in polypeptides of this invention described herein, can be made, for example, using any of the techniques and guidelines for conservative and non-conservative mutations set forth, for instance, in U.S. Pat. No. 5,364,934. Variations can be a substitution, deletion or insertion of one or more codons encoding the polypeptide that results in a change in the amino acid sequence of the polypeptide. Amino acid substitutions can be the result of replacing one amino acid with another amino acid having similar structural and/or chemical properties, such as the replacement of a leucine with a serine, i.e., conservative amino acid replacements. Insertions or deletions can optionally be in the range of about 1 to 5 amino acids. The variation allowed can be determined by systematically making insertions, deletions or substitutions of amino acids in the sequence and testing the resulting variants for activity exhibited by the full-length or mature native sequence.

TABLE 4

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in function or immunological identity of the polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: Norleucine, Met, Ala, Val, Leu, Ile;
(2) neutral hydrophilic: Cys, Ser, Thr; Asn, Gln
(3) acidic: Asp, Glu;
(4) basic: His, Lys, Arg;
(5) residues that influence chain orientation: Gly, Pro; and
(6) aromatic: Trp, Tyr, Phe.

Non-conservative substitutions will entail exchanging a member of one of these classes for another class. Such substituted residues also may be introduced into the conservative substitution sites or, more preferably, into the remaining (non-conserved) sites.

The term "amino acid" within the scope of the present invention is used in its broadest sense and is meant to include the naturally occurring L α-amino acids or residues. The commonly used one and three letter abbreviations for naturally occurring amino acids are used herein (Lehninger, A. L., Biochemistry, 2d ed., pp. 71-92, (1975), Worth Publishers, New York). The term includes D-amino acids as well as chemically modified amino acids such as amino acid analogs, naturally occurring amino acids that are not usually incorporated into proteins such as norleucine, and chemically synthesized compounds having properties known in the art to be characteristic of an amino acid. For example, analogs or mimetics of phenylalanine or proline, which allow the same conformational restriction of the peptide compounds as natural Phe or Pro are included within the definition of amino acid. Such analogs and mimetics are referred to herein as "functional equivalents" of an amino acid. Other examples of amino acids are listed by Roberts and Vellaccio (The Peptides: Analysis, Synthesis, Biology,) Eds. Gross and Meiehofer, Vol. 5 p 341, Academic Press, Inc, N.Y. 1983, which is incorporated herein by reference.

Amino acids can be grouped according to similarities in the properties of their side chains (in A. L. Lehninger, in Biochemistry, second ed., pp. 73-75, Worth Publishers, New York (1975)):

(1) nonpolar: Ala, Val, Leu, Ile, Pro, Phe, Trp, Met
(2) uncharged polar: Gly, Ser, Thr, Cys, Tyr, Asn, Gln
(3) acidic: Asp, Glu
(4) basic: Lys, Arg, His The term "conservative" amino acid substitution as used within this invention is meant to refer to amino acid substitutions which substitute functionally equivalent amino acids. Conservative amino acid changes result in silent changes in the amino acid sequence of the resulting peptide. For example, one or more amino acids of a similar polarity act as functional equivalents and result in a silent alteration within the amino acid sequence of the peptide. In general, substitutions within a group can be considered conservative with respect to structure and function. However, the skilled artisan will recognize that the role of a particular residue is determined by its context within the three-dimensional structure of the molecule in which it occurs. For example, Cys residues may occur in the oxidized (disulfide) form, which is less polar than the reduced (thiol) form. The long aliphatic portion of the Arg side chain can constitute a critical feature of its structural or functional role, and this may be best conserved by substitution of a nonpolar, rather than another basic residue. Also, it will be recognized that side chains containing aromatic groups (Trp, Tyr, and Phe) can participate in ionic-aromatic or "cation-pi" interactions. In these cases, substitution of one of these side chains with a member of the acidic or uncharged polar group may be conservative with respect to structure and function. Residues such as Pro, Gly, and Cys (disulfide form) can have direct effects on the main chain conformation, and often may not be substituted without structural distortions.

Peptides synthesized by the standard solid phase synthesis techniques described here, for example, are not limited to amino acids encoded by genes for substitutions involving the amino acids. Commonly encountered amino acids which are not encoded by the genetic code, include, for example, those described in International Publication No. WO 90/01940, as well as, for example, 2-amino adipic acid (Aad) for Glu and Asp; 2-aminopimelic acid (Apm) for Glu and Asp; 2-aminobutyric (Abu) acid for Met, Leu, and other aliphatic amino acids; 2-aminoheptanoic acid (Ahe) for Met, Leu and other aliphatic amino acids; 2-aminoisobutyric acid (Aib) for Gly; cyclohexylalanine (Cha) for Val, and Leu and Ile; homoarginine (Har) for Arg and Lys; 2,3-diaminopropionic acid (Dpr) for Lys, Arg and His; N-ethylglycine (EtGly) for Gly, Pro, and Ala; N-ethylglycine (EtGly) for Gly, Pro, and Ala; N-ethylasparagine (EtAsn) for Asn, and Gln; Hydroxyllysine (Hyl) for Lys; allohydroxyllysine (AHyl) for Lys; 3-(and 4) hydroxyproline (3Hyp, 4Hyp) for Pro, Ser, and Thr; allo-isoleucine (Alle) for Ile, Leu, and Val; -amidinophenylalanine for Ala; N-methylglycine (MeGly, sarcosine) for Gly, Pro, and Ala; N-methylisoleucine (MeIle) for Ile; Norvaline (Nva) for Met and other aliphatic amino acids; Norleucine (Nle) for Met and other aliphatic amino acids; Ornithine (Orn or Or) for Lys, Arg and His; Citrulline (Cit) and methionine sulfoxide (MSO) for Thr, Asn and Gln; -methylphenylalanine (MePhe), trimethylphenylalanine, halo (F, Cl, Br, and I)phenylalanine, triflourylphenylalanine, for Phe.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis [Wells et al., *Gene,* 34:315 (1985)], restriction selection mutagenesis [Wells et al., *Philos. Trans. R. Soc. London SerA,* 317:415 (1986)] or other known techniques can be performed on the cloned DNA to produce the variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant [Cunningham and Wells, *Science,* 244: 1081-1085 (1989)]. Alanine is also typically preferred because it is the most common amino acid. Further, it is frequently found in both buried and exposed positions [Creighton, *The Proteins*, (W.H. Freeman & Co., N.Y.); Chothia, *J Mol. Biol.*, 150:1 (1976)]. If alanine substitution does not yield adequate amounts of variant, an isoteric amino acid can be used.

Immunoadhesin molecules comprising the polypeptides of this invention are further contemplated for use in the methods herein. In one embodiment, the molecule comprises a fusion of a polypeptide of this invention with an immunoglobulin or a particular region of an immunoglobulin. For a bivalent form of the immunoadhesin, such a fusion usefully comprise the Fc region of an IgG molecule. In a further embodiment, the Fc region is from a human IgG1 molecule. In one embodiment, the immunoglobulin fusion includes the hinge, CH2 and CH3, or the hinge, CH1, CH2 and CH3 regions of an IgG1 molecule. For the production of immunoglobulin fusions, see also U.S. Pat. No. 5,428,130 issued Jun. 27, 1995 and Chamow et al., *TIBTECH,* 14:52-60 (1996).

The simplest and most straightforward immunoadhesin design often combines the binding domain(s) of the adhesin (e.g. polypeptide of this invention) with the Fc region of an immunoglobulin heavy chain. Ordinarily, when preparing the immunoadhesins of the present invention, nucleic acid encoding the binding domain of the adhesin will be fused C-terminally to nucleic acid encoding the N-terminus of an immunoglobulin constant domain sequence, however N-terminal fusions are also possible.

Typically, in such fusions the encoded chimeric polypeptide will retain at least functionally active hinge, CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain. The precise site at which the fusion is made is not critical; particular sites are well known and can be selected in order to optimize the biological activity, secretion, or binding characteristics of the immunoadhesin.

In a preferred embodiment, the adhesin sequence is fused to the N-terminus of the Fc region of immunoglobulin G1 (IgG1). It is possible to fuse the entire heavy chain constant region to the adhesin sequence. However, more preferably, a sequence beginning in the hinge region just upstream of the papain cleavage site which defines IgG Fc chemically (i.e. residue 216, taking the first residue of heavy chain constant region to be 114), or analogous sites of other immunoglobulins is used in the fusion. In a particularly preferred embodiment, the adhesin amino acid sequence is fused to (a) the hinge region and CH2 and CH3 or (b) the CH1, hinge, CH2 and CH3 domains, of an IgG heavy chain.

For bispecific immunoadhesins, the immunoadhesins are assembled as multimers, and particularly as heterodimers or heterotetramers. Generally, these assembled immunoglobulins will have known unit structures. A basic four chain structural unit is the form in which IgG, IgD, and IgE exist. A four chain unit is repeated in the higher molecular weight immunoglobulins; IgM generally exists as a pentamer of four basic units held together by disulfide bonds. IgA globulin, and occasionally IgG globulin, may also exist in multimeric form in serum. In the case of multimer, each of the four units may be the same or different.

Various exemplary assembled immunoadhesins within the scope herein are schematically diagrammed below:
(a) ACL-ACL;
(b) ACH-(ACH, ACL-ACH, ACL-VHCH, or VLCL-ACH);
(c) ACL-ACH-(ACL-ACH, ACL-VHCH, VLCL-ACH, or VLCL-VHCH);
(d) ACL-VHCH-(ACH, or ACL-VHCH, or VLCL-ACH);
(e) VLCL-ACH-(ACL-VHCH, or VLCL-ACH); and
(f) (A-Y)n-(VLCL-VHCH)2,
wherein each A represents identical or different adhesin amino acid sequences;
VL is an immunoglobulin light chain variable domain;
VH is an immunoglobulin heavy chain variable domain;
CL is an immunoglobulin light chain constant domain;
CH is an immunoglobulin heavy chain constant domain;
n is an integer greater than 1;
Y designates the residue of a covalent cross-linking agent.

In the interests of brevity, the foregoing structures only show key features; they do not indicate joining (J) or other domains of the immunoglobulins, nor are disulfide bonds shown. However, where such domains are required for binding activity, they shall be constructed to be present in the ordinary locations which they occupy in the immunoglobulin molecules.

Alternatively, the adhesin sequences can be inserted between immunoglobulin heavy chain and light chain sequences, such that an immunoglobulin comprising a chimeric heavy chain is obtained. In this embodiment, the adhesin sequences are fused to the 3' end of an immunoglobulin heavy chain in each arm of an immunoglobulin, either between the hinge and the CH2 domain, or between the CH2 and CH3 domains. Similar constructs have been reported by Hoogenboom et al., *Mol. Immunol.*, 28:1027-1037 (1991).

Although the presence of an immunoglobulin light chain is not required in the immunoadhesins of the present invention, an immunoglobulin light chain might be present either covalently associated to an adhesin-immunoglobulin heavy chain fusion polypeptide, or directly fused to the adhesin. In the former case, DNA encoding an immunoglobulin light chain is typically coexpressed with the DNA encoding the adhesin-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Methods suitable for the preparation of such structures are, for example, disclosed in U.S. Pat. No. 4,816,567, issued 28 Mar. 1989.

Immunoadhesins are most conveniently constructed by fusing the cDNA sequence encoding the adhesin portion in-frame to an immunoglobulin cDNA sequence. However, fusion to genomic immunoglobulin fragments can also be used (see, e.g. Aruffo et al., *Cell*, 61:1303-1313 (1990); and Stamenkovic et al., *Cell*, 66:1133-1144 (1991)). The latter type of fusion can requires the presence of Ig regulatory sequences for expression. cDNAs encoding IgG heavy-chain constant regions can be isolated based on published sequences from cDNA libraries derived from spleen or peripheral blood lymphocytes, by hybridization or by polymerase chain reaction (PCR) techniques. The cDNAs encoding the "adhesin" and the immunoglobulin parts of the immunoadhesin can be inserted in tandem into a plasmid vector that directs efficient expression in the chosen host cells.

Leucine zipper forms of these molecules are also contemplated by the invention. "Leucine zipper" is a term in the art used to refer to a leucine rich sequence that enhances, promotes, or drives dimerization or trimerization of its fusion partner (e.g., the sequence or molecule to which the leucine zipper is fused or linked to). Various leucine zipper polypeptides have been described in the art. See, e.g., Landschulz et al., *Science*, 240:1759 (1988); U.S. Pat. No. 5,716,805; WO 94/10308; Hoppe et al., *FEBS Letters*, 344:1991 (1994); Maniatis et al., *Nature*, 341:24 (1989). Those skilled in the art will appreciate that a leucine zipper sequence can be fused at either the 5' or 3' end of the polypeptide of this invention.

The polypeptides of the present invention can also be modified in a way to form chimeric molecules by fusing the polypeptide to another, heterologous polypeptide or amino acid sequence. According to one embodiment, such heterologous polypeptide or amino acid sequence is one which acts to oligimerize the chimeric molecule. In one embodiment, such a chimeric molecule comprises a fusion of the polypeptide with a tag polypeptide which provides an epitope to which an anti-tag antibody can selectively bind. The epitope tag is generally placed at the amino- or carboxyl-terminus of the polypeptide. The presence of such epitope-tagged forms of the polypeptide can be detected using an antibody against the tag polypeptide. Also, provision of the epitope tag enables the polypeptide to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159-2165 (1988)]; the c-myc tag and the 8F9, 3C7, 6E10, G4, B7 and 9E10 antibodies thereto [Evan et al., *Mol. Cell. Biol.*, 5:3610-3616 (1985)]; and the Herpes Simplex virus glycoprotein D (gD) tag and its antibody [Paborsky et al., *Protein Engineering*, 3(6):547-553 (1990)]. Other tag polypeptides include the Flag-peptide [Hopp et al., *BioTechnology*, 6:1204-1210 (1988)]; the KT3 epitope peptide [Martin et al., *Science*, 255:192-194 (1992)]; an "-tubulin epitope peptide [Skinner et al., *J. Biol. Chem.*, 266:15163-15166 (1991)]; and the T7 gene 10 protein peptide tag [Lutz-Freyermuth et al., *Proc. Natl. Acad. Sci. USA*, 87:6393-6397 (1990)].

It is contemplated that the polypeptides of this invention will be used to create antibodies comprising the polypeptides.

It can be desirable to modify an antibody of the invention with respect to effector function, so as to enhance the effectiveness of the antibody in treating an immune related disease, for example. For example cysteine residue(s) may be introduced in the Fc region, thereby allowing interchain disulfide bond formation in this region. The homodimeric antibody thus generated can have improved internalization capability and/or increased complement-mediated cell killing and antibody-dependent cellular cytotoxicity (ADCC). See Caron et al., *J Exp Med* 176:1191-1195 (1992) and Shopes, B., *J. Immunol.* 148:2918-2922 (1992). Homodimeric antibodies with enhanced anti-tumor activity can also be prepared using heterobifunctional cross-linkers as described in Wolff et al. *Cancer Research* 53:2560-2565 (1993). Alternatively, an antibody can be engineered which has dual Fc regions and can thereby have enhanced complement lysis and ADCC capabilities. See Stevenson et al., *Anti-Cancer Drug Design*, 3:219-230 (1989).

The binding specificity of monoclonal antibodies can be determined by immunoprecipitation or by an in vitro binding assay, such as radioimmunoassay (RIA) or enzyme-linked immunoabsorbent assay (ELISA). The binding affinity of the monoclonal antibody can, for example, be determined by the Scatchard analysis of Munson et al., *Anal. Biochem.*, 107:220 (1980).

Antibodies or antibody fragments comprising a polypeptide of this invention can be isolated from antibody phage libraries generated using the techniques described in McCafferty et al., *Nature*, 348:552-554 (1990). Clackson et al., *Nature*, 352:624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.*, 21:2265-2266 (1993)).

The DNA also cam be modified, for example, by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

Methods for humanizing non-human antibodies have been described in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522-525 (1986); Riechmann et al., *Nature*, 332:323-327 (1988); Verhoeyen et al., *Science*, 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework region (FR) for the humanized antibody (Sims et al., *J. Immunol.*, 151:2296 (1993); Chothia et al., *J. Mol. Biol.*, 196:901 (1987)).

Another method uses a particular framework region derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various techniques have been developed for the production of antibody fragments. Traditionally, these fragments were derived via proteolytic digestion of intact antibodies (see, e.g., Morimoto et al, *Journal of Biochemical and Biophysical Methods* 24:107-117 (1992) and Brennan et al, *Science*, 229: 81 (1985)). However, these fragments can now also be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., Bio/Technology 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. The antibody fragment can also be a "linear antibody", e.g., as described in U.S. Pat. No. 5,641,870 for example. Such linear antibody fragments may be monospecific or bispecific.

Bispecific antibodies are antibodies that have binding specificities for at least two different epitopes (e.g., an epitope on APRIL and an epitope on BAFF). In one embodiment, an anti-BAFF or anti-APRIL binding arm can be combined with an arm which binds to a triggering molecule on a leukocyte such as a T-cell receptor molecule (e.g. CD2 or CD3), or Fc receptors for IgG (FcR), such as FcRI (CD64), FcRII (CD32) and FcRIII (CD16) or NK receptors (e.g., NKG2D) so as to focus cellular defense mechanisms to the cells expressing APRIL or BAFF. Bispecific antibodies may also be used to localize cytotoxic agents to the B cell. These antibodies possess a B cell marker-binding arm and an arm which binds the cytotoxic agent (e.g. saporin, vinca alkaloid, ricin A chain, methotrexate or radioactive isotope hapten). Bispecific antibodies can be prepared as full length antibodies or antibody fragments (e.g. F(ab')$_2$ bispecific antibodies).

Methods for making bispecific antibodies are known in the art. According to a one approach, antibody variable domains comprising a polypeptide of this invention are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al, *Methods in Enzymology*, 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676, 980), and for treatment of HIV infection (WO 91/00360, WO 92/200373, and EP 03089). Heteroconjugate antibodies can be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al, *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al, *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al, *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al, *Proc. Natl. Acad. Sci. USA*, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991).

Additional amino acid sequence modification(s) of the polypeptides of this invention, including antibodies, described herein are contemplated. For example, it may be desirable to improve the binding affinity and/or other biological properties of a polypeptide of this invention. Amino acid sequence variants of the polypeptides of this invention can be prepared by introducing appropriate nucleotide changes into the nucleic acid encoding it, or by peptide synthesis. Such modifications include, for example, deletions from, and/or insertions into and/or substitutions of, residues within the amino acid sequences of the antagonist. Any combination of deletion, insertion, and substitution is made to arrive at the final construct, provided that the final construct possesses the desired characteristics, a biological activity of BCMA. The amino acid changes also cam alter post-translational processes of the antagonist, such as changing the number or position of glycosylation sites.

A useful method for identification of other residues or regions of the polypeptides of this invention that are preferred locations for mutagenesis is called "alanine scanning mutagenesis" as described by Cunningham and Wells *Science*, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antagonist variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include a polypeptide of this invention with an N-terminal methionyl residue or the a polypeptide of this invention fused to a cytotoxic polypeptide. Other insertional variants of the polypeptide include the fusion to the N- or C-terminus of the polypeptide to an agent that increases the serum half-life of the polypeptide (e.g., a serum albumin binding peptide).

Another type of variant is an amino acid substitution variant. These variants have at least one amino acid residue in the antagonist molecule replaced by different residue. The sites of greatest interest for substitutional mutagenesis of antibody antagonists include the hypervariable regions, but FR alterations are also contemplated. Conservative substitutions are shown in Table 4 above under the heading of "preferred substitutions". If such substitutions result in a change in biological activity, then more substantial changes, denominated "exemplary substitutions" in Table 4 can be introduced and the products screened.

To increase the half-life of the immunoadhesins, antibodies or other polypeptides of this invention, one can attach a salvage receptor binding epitope to the antibody (especially an antibody fragment), immunoadhesin or polypeptide of this invention as described in U.S. Pat. No. 5,739,277, for example (e.g., the nucleic acid encoding the salvage receptor binding epitope can be linked in frame to a nucleic acid encoding a polypeptide sequence of this invention so that the fusion protein expressed by the nucleic acid molecule comprises the epitope and a polypeptide sequence of this invention). As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule. Antibodies with substitutions in an Fc region thereof and increased serum half-lives are also described in WO00/42072 (Presta, L.). In another embodiment, the serum half-life can also be increased, for example, by attaching serum albumin or a portion of serum albumin that binds to the FcRn receptor or a serum albumin binding peptide described in WO01/45746 to an immunoadhesin, antibody or polypeptide of this invention. See also, Dennis, M. S., et al., (2002) *JBC* 277(38): 35035-35043 for serum albumin binding peptide sequences.

Agents that can be attached directly or indirectly to a polypeptide of this invention to enhance its therapeutic or diagnostic use include, for example, non-proteinaceous polymers comprising polyethylene glycol (PEG). There are several methods for conjugating polypeptides to other molecules (e.g., polymers, small molecules, detection reagents) known in the art. For example, a polypeptide and a polymer comprising polyethylene glycol, each bearing a special functionality that is mutually reactive toward the other, can be joined in solution via a linkage. The polypeptides can be "preactivated" with an appropriate functional group at a specific site. Ligation of the polypeptide with PEG can take place in aqueous phase and be easily monitored by reverse phase analytical HPLC. The PEGylated polypeptides can be easily purified by preparative HPLC and characterized by analytical HPLC, amino acid analysis and laser desorption mass spectrometry.

a. Polypeptide Reactive Sites

In some embodiments, a polypeptide of this invention is covalently bonded via one or more of the amino acid residues of the polypeptide to a terminal reactive group on the polymer, depending mainly on the reaction conditions, the molecular weight of the polymer, etc. In some embodiments, multiple polypeptides are conjugated to a polymer having two or more terminal reactive groups. The polymer with the reactive group(s) is designated herein as activated polymer. The reactive group can react with free amino or other reactive groups on the polypeptide. Potential reactive sites include: N-terminal amino groups, epsilon amino groups on lysine residues, as well as other amino, imino, carboxyl, sulfhydryl, hydroxyl, and other hydrophilic groups. It will be understood, however, that the type and amount of the reactive group chosen, as well as the type of polymer employed, to obtain optimum results, can be varied depending on the particular polypeptide employed. In some embodiments, a reactive residue, (e.g., lysine (K), a modified, non-natural amino acid, or other small molecule) may be substituted at a position suitable for conjugation.

In some embodiments, the polypeptide comprises a sequence selected from the group consisting of Formula I (SEQ ID NO:1), CSQNEYFDSLLHACKPCQLRCSSNTP-PLTCQRYC (SEQ ID NO:6), CSQNEYFDSLLHACK-PCDLRCSSNTPPLTCQRYC (SEQ ID NO:7), CSQNEY-FDSLVHACKPCDLYCSSNTPPLTCQRYC (SEQ ID NO:8), CSQNEYFDSLVHACKPCQLRCSSNTP-PLTCQRYC (SEQ ID NO:9), Formula II (SEQ ID NO:10), CSQNEAFDSLLHACIPCQLRCSSNTPPLTCQRYC (SEQ ID NO: 13), CSQNESFDSLLHACIPCQLRCSSNTP-PLTCQRYC (SEQ ID NO:14), CSQNEFFDSLLHACIPC-QLRCSSNTPPLTCQRYC (SEQ ID NO:15), CSQNEYFD-SLLHACIPCDLRCSSNTPPLTCQRYC (SEQ ID NO:16), CSQNEYFDSLLHACIPCQLYCSSNTPPLTCQRYC (SEQ ID NO:17), and CSQNEYFDSLLHACIPCDLYCSSNTP-PLTCQRYC (SEQ ID NO:18) and further has a terminal reactive group. In some embodiments, the polypeptide of this invention comprises more than one of a polypeptide of this invention conjugated together. For example, the polypeptides that are linked together can have the same sequence or have different sequences and a terminal reactive group. In another embodiment, these polypeptides can be joined to one another through the use of a linker.

While conjugation at any reactive amino acid on the polypeptide is contemplated, in some embodiments, the reactive amino acid is lysine, which is linked to the reactive group of the activated polymer through its free epsilon-amino group, or glutamic or aspartic acid, which is linked to the polymer through an amide bond.

The degree of polymer conjugation with each polypeptide can vary, for example, depending upon the number of reactive sites on the polypeptide, the molecular weight, hydrophilicity and other characteristics of the polymer, and the particular polypeptide derivatization sites chosen. In some embodiments, the conjugate has a final molar ratio of 1 to 10 polymer molecules per polypeptide molecule, but greater numbers of polymer molecules attached to the polypeptides of the invention are also contemplated. In another embodiment, the conjugate has a final molar ratio of 1 to 10 polypeptide molecules per polymer molecule. The desired amount of derivatization can be achieved by using an experimental matrix in which the time, temperature and other reaction conditions are varied to change the degree of substitution, after which the level of polymer substitution of the conjugates can determined by size exclusion chromatography or other means known in the art.

b. Activated Polymers

In some embodiments, the polymer contains only a single group which is reactive. In one preferred embodiment, the polymer-polypeptide reaction conditions are maximized to reduce cross-linking, or to purify the reaction products through gel filtration or ion exchange chromatography to recover substantially homogenous derivatives. In some embodiments, the polymer is covalently bonded directly to the polypeptide without the use of a multifunctional crosslinking agent.

In other embodiments, the polymer contains two or more reactive groups that can link multiple polypeptides to the polymer backbone. For example, a homobifunctional PEG molecule has a reactive group on each end of a linear PEG, such that a polypeptide is covalently attached at each end. In some embodiments, branched PEG molecules are used to provide multiple reactive sites for polypeptide conjugation. Gel filtration or ion exchange chromatography can be used to recover the desired derivative in substantially homogeneous form.

The covalent modification reaction can take place by any appropriate method generally used for reacting biologically active materials with inert polymers. In some embodiments, the reactions are at about pH 5-9 if the reactive groups on the polypeptide are lysine groups. An example process can involve preparing an activated polymer (the polymer typically having at least one terminal hydroxyl group to be activated), preparing an active substrate from this polymer, and thereafter reacting the polypeptide with the active substrate to produce the modified polypeptide. The above modification reaction can be performed by several methods, which may involve one or more steps. Examples of modifying agents that can be used to produce the activated polymer in a one-step reaction include cyanuric acid chloride (2,4,6-trichloro-S-triazine) and cyanuric acid fluoride.

In some embodiments, the modification reaction takes place in two steps wherein the polymer is reacted first with an acid anhydride such as succinic or glutaric anhydride to form a carboxylic acid, and the carboxylic acid is then reacted with a compound capable of reacting with the carboxylic acid to form an activated polymer with a reactive ester group that is capable of reacting with the polypeptide. Examples of such compounds include N-hydroxysuccinimide, 4-hydroxy-3-nitrobenzene sulfonic acid, and the like. In one preferred embodiment, preferably N-hydroxysuccinimide or 4-hydroxy-3-nitrobenzene sulfonic acid is used. For example, monomethyl substituted PEG can be reacted at elevated temperatures, preferably about 100-110° C. for four hours, with glutaric anhydride. The monomethyl PEG-glutaric acid thus produced is then reacted with N-hydroxysuccinimide in the presence of a carbodiimide reagent such as dicyclohexyl or isopropyl carbodiimide to produce the activated polymer, methoxypolyethylene glycolyl-N-succinimidyl glutarate, which can then be reacted with the GH. This method is described in detail in Abuchowski et al., *Cancer Biochem. Biophys.*, 7: 175-186 (1984). In another example, the monomethyl substituted PEG can be reacted with glutaric anhydride followed by reaction with 4-hydroxy-3-nitrobenzene sulfonic acid (HNSA) in the presence of dicyclohexyl carbodiimide to produce the activated polymer. HNSA is described by Bhatnagar et al., *Peptides: Synthesis-Structure-Func-tion. Proceedings of the Seventh American Peptide Symposium*, Rich et al. (eds.) (Pierce Chemical Co., Rockford Ill., 1981), p. 97-100, and in Nitecki et al., *High-Technology Route to Virus Vaccines* (American Society for Microbiology:

1986) entitled "Novel Agent for Coupling Synthetic Peptides to Carriers and Its Applications."

In some embodiments, covalent binding to amino groups is accomplished by known chemistries based upon cyanuric chloride, carbonyl diimidazole, aldehyde reactive groups (PEG alkoxide plus diethyl acetal of bromoacetaldehyde; PEG plus DMSO and acetic anhydride, or PEG chloride plus the phenoxide of 4-hydroxybenzaldehyde, activated succinimidyl esters, activated dithiocarbonate PEG, 2,4,5-trichlorophenylcloroformate or P-nitrophenylcloroformate activated PEG.). Carboxyl groups can be derivatized, for example, by coupling PEG-amine using carbodiimide. Sulfhydryl groups can be derivatized, for example, by coupling to maleimido-substituted PEG (e.g. alkoxy-PEG amine plus sulfosuccinimidyl 4-(N-maleimidomethyl)cyclohexane-1-carboxylate) as described in WO 97/10847 published Mar. 27, 1997, or PEG-maleimide commercially available from Nektar Technologies, San Carlos, Calif. (formerly Shearwater Polymers, Inc.). Alternatively, free amino groups on the polypeptide (e.g. epsilon amino groups on lysine residues) can be coupled to N-hydroxysucciminidyl substituted PEG (PEG-NHS available from Nektar Technologies;) or can be thiolated with 2-imino-thiolane (Traut's reagent) and then coupled to maleimide-containing derivatives of PEG as described in Pedley et al., *Br. J. Cancer*, 70: 1126-1130 (1994).

Many inert polymers are suitable for use in pharmaceuticals. See, e.g., Davis et al., Biomedical Polymers Polymeric Materials and Pharmaceuticals for Biomedical Use, pp. 441-451 (1980). A non-proteinaceous polymer is typically a hydrophilic synthetic polymer, i.e., a polymer not otherwise found in nature, but includes polymers which exist in nature and are produced by recombinant or in vitro methods or are isolated from native sources. Hydrophilic polyvinyl polymers fall within the scope of this invention, e.g. polyvinyl alcohol and polyvinylpyrrolidone. Other useful polymers are polyalkylene ethers such as polyethylene glycol (PEG); polyoxyalkylenes such as polyoxyethylene, polyoxypropylene, and block copolymers of polyoxyethylene and polyoxypropylene (PLURONIC®); polymethacrylates; carbomers; branched or unbranched polysaccharides which comprise the saccharide monomers D-mannose, D- and L-galactose, fucose, fructose, D-xylose, L-arabinose, D-glucuronic acid, sialic acid, D-galacturonic acid, D-mannuronic acid (e.g. polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextrane sulfate, dextran, dextrins, glycogen, or the polysaccharide subunit of acid mucopolysaccharides, e.g. hyaluronic acid; polymers of sugar alcohols such as polysorbitol and polymannitol; heparin or heparon.

The polymer prior to conjugation need not be, but preferably is, water soluble, but the final conjugate is preferably water-soluble. Preferably, the conjugate exhibits a water solubility of at least about 0.01 mg/ml, and more preferably at least about 0.1 mg/ml, and still more preferably at least about 1 mg/ml. In addition, it is desirable that the polymer is not highly immunogenic in the conjugate form, nor viscous such that is incompatible with intravenous infusion, injection, or inhalation if the conjugate is intended to be administered by such routes.

The molecular weight of the polymer can range up to about 100,000 D, and preferably is at least about 500 D, or at least about 1,000 D, or at least about 5,000 D. In some embodiments, the PEG or other polymer has a molecular weight in the range of 5000 (5 k) to 20,000 (20 k) D. The molecular weight chosen can depend upon the effective size of the conjugate to be achieved, the nature (e.g. structure, such as linear or branched) of the polymer, and the degree of derivatization, i.e. the number of polymer molecules per polypeptide, and the polymer attachment site or sites on the polypeptide. In some embodiments, branched PEG's can be used to induce a large increase in effective size of the polypeptides. PEG or other polymer conjugates can be useful for, inter alia, increasing half-life, increasing solubility, stabilizing against proteolytic attack, and reducing immunogenicity of the polypeptide. In some embodiments, a single PEG molecule with molecular weight in the range of 5 k to 40 k can be conjugated to one or more polypeptides of this invention, which is suitable for, for example, administration by inhalation.

Functionalized PEG polymers as described above can be synthesized or purchased from companies such as Nektar Technologies of San Carlos, Calif. (formerly Shearwater Polymers, Inc.). Such commercially available PEG derivatives include, but are not limited to, amino-PEG, PEG amino acid esters. PEG-N-hydroxysuccinamide chemistry (NHS), PEG-hydrazide, PEG-thiol, PEG-succinate, carboxymethylated PEG, PEG-propionic acid, PEG amino acids, PEG succinimidyl succinate, PEG succinimidyl propionate, succinimidyl ester of carboxymethylated PEG, succinimidyl carbonate of PEG, succinimidyl esters of amino acid PEGs, PEG-xycarbonylimidazole, PEG-nitrophenyl carbonate, PEG tresylate, PEG-glycidyl ether, PEG-aldehyde, PEG vinylsulfone, PEG-maleimide, PEG-orthopyridyl-disulfide, heterofunctional PEGs, PEG vinyl derivatives, PEG silanes, and PEG phospholides. The reaction conditions for coupling these PEG derivatives to proteins in general are known and will vary depending on a number of factors, including, the polypeptide, the desired degree of PEGylation, and the PEG derivative utilized. Some factors involved in the choice of PEG derivatives include: the desired point of attachment (such as lysine or cysteine R-groups), hydrolytic stability and reactivity of the derivatives, stability, toxicity and antigenicity of the linkage, suitability for analysis, etc.

c. Characterization of Conjugates.

The polymer-protein conjugates may be characterized by any one of a number of assays, including SDS-PAGE, gel filtration, NMR, tryptic mapping, liquid chromatography-mass spectrophotometry, and in vitro biological assays. For example, the extent of PEG conjugation may be shown by SDS-PAGE and gel filtration, and then analyzed by NMR, which has a specific resonance peak for the methylene hydrogens of PEG. The number of PEG groups on each molecule can be calculated from the NMR spectrum or mass spectrometry. Polyacrylamide gel electrophoresis in 10% SDS is appropriately run in 10 mM Tris-HCl pH 8.0, 100 mM NaCl as elution buffer. To demonstrate which residue is PEGylated, tryptic mapping can be performed. Thus, PEGylated polypeptides can be digested with trypsin at the protein/enzyme ratio of 100 to 1 in mg basis at 37° C. for 4 hours in 100 mM sodium acetate, 10 mM Tris-HCl, 1 mM calcium chloride, pH 8.3, and acidified to pH<4 to stop digestion before separating on HPLC NUCLEOSIL® C-18 (4.6 mm×150 mm, 5.mu., 100 A). The chromatogram can be compared to that of non-PEGylated starting material. Each peak can then be analyzed by mass spectrometry to verify the size of the fragment in the peak. The fragment(s) that carried PEG groups are usually not retained on the HPLC column after injection and disappear from the chromatograph. Such disappearance from the chromatograph is an indication of PEGylation on that particular fragment. PEGylated peptides can be assayed for the ability to bind to April or BAFF by conventional methods.

In some embodiments, conjugates are purified by ion-exchange chromatography, (e.g, ion exchange HPLC). The chemistry of many of the electrophilically activated PEGs results in a reduction of amino group charge of the PEGylated product. Thus, high resolution ion exchange chromatography can be used to separate the free and conjugated proteins, and to resolve species with different levels of PEGylation. In fact, the resolution of different species (e.g. containing one or two PEG residues) is also possible due to the difference in the ionic properties of the unreacted amino acids. In one embodiment, species with difference levels of PEGylation are resolved according to the methods described in WO 96/34015 (International Application No. PCT/US96/05550 published Oct. 31, 1996). According to one embodiment, heterologous species of the conjugates are purified from one another in the same fashion.

B. Assay Methods

According to one embodiment, BAFF/BAFF receptor binding studies or APRIL/APRIL receptor binding studies can be carried out in any known assay method, such as competitive binding assays, direct and indirect sandwich assays, and immunoprecipitation assays. According to another embodiment, binding assays are carried out as described herein, using the polypeptides of the invention in place of native sequence BCMA. Cell-based assays and animal models can be used to further understand the interaction between the BCMA and its ligands and the development and pathogenesis of the conditions and diseases referred to herein. Depending on the assay, the polypeptides of this invention can be for example, a soluble polypeptide, a membrane-bound polypeptide with transmembrane and cytoplasmic region of a non-BCMA polypeptide or a native BCMA polypeptide, or a polypeptide immobilized on a solid substrate.

In one approach, mammalian cells can be transfected with a nucleic acid molecule encoding BCMA, and the ability of test polypeptide to inhibit binding APRIL or BAFF to its receptor or APRIL or BAFF activity is analyzed.

In addition, primary cultures derived from transgenic animals can be used in the cell-based assays. Techniques to derive continuous cell lines from transgenic animals are well known in the art. [see, e.g., Small et al., *Mol. Cell. Biol.,* 5:642-648 (1985)].

In one cell based assay, epitope-tagged BAFF or APRIL (e.g., AP or Flag) is added to cells that have or express a polypeptide of this invention, and analyzed for binding to the cells by FACS staining with anti-tag antibody. In another assay, the ability of a polypeptide of this invention to inhibit the BAFF or APRIL induced proliferation of B cells, T cells or tumor cells is assayed. Primary cells or cell lines can be cultured with BAFF or APRIL in the presence or absence of the test polypeptide and the proliferation of the cells can be measured by, e.g., 3H-thymidine incorporation or FACS analysis.

To test the direct role of a polypeptide in inhibiting T cell activation, an in vitro assay of antigen-specific activation of T cells can be performed. Activation of T cells by anti-CD3 antibody in vitro in the presence of test polypeptide can be examined by measuring proliferation and IL-2 production by these T cells.

Splenic cells from adult C57BL/6 mice (Jackson Laboratory) can be cultured ($1\times10^6$ per well) in various concentrations of 10 µg/ml anti-CD3 monoclonal antibody (Pharmingen) with or without different concentrations of the test polypeptide in medium as described above. Proliferation can be measured by uptake of $^3$H-thymidine. Parallel assays can also be set up to measure the effects of the test polypeptide on production of anti-CD3 antibody induced IL-2 production in a 24 hour culture system. An ELISA can be used to determine IL-2 levels in supernatants, using antibodies from Pharmingen, and using their recommended protocols.

To study the effects of the test polypeptide on in vitro stimulation of TCR transgenic cells, $1\times10^6$ cells from adult MBP-TCR transgenic mice (e.g., from Dr. Richard Flavell, Howard Hughes Medical Institute, Yale University) can be cultured in the presence of 10 µg/ml MBP-Ac1-11 (a synthetic NH2-terminal peptide of Myelin Basic Protein having amino acid sequence ASQKRPSQRSK (SEQ ID NO:27) with the first amino acid acetylated) with or without different concentrations of test polypeptide in 96-well plates in DMEM medium supplemented with 5% FCS, 2 mM glutamine, 100 U/ml penicillin, 100 µg/ml streptomycin. Proliferation can be measured by addition of 1 µCi of [$^3$H] thymidine (International Chemical and Nuclear, Irvine, Calif.) for the last 18 hours of a 5-day culture, and incorporation of radioactivity can be assayed by liquid scintillation counting. The inhibition of anti-CD3 antibody-induced proliferation of naive T cells or anti-CD3 antibody-induced IL-2 production in a dose dependent manner is an indicator that T cell activation can be blocked with the test polypeptide.

The results of the cell based in vitro assays can be further verified using in vivo animal models. A variety of well known animal models can be used to further study the polypeptides of the invention in immune related disease or cancer and to test the efficacy of the candidate therapeutic agents. The in vivo nature of such models makes them particularly predictive of responses in human patients. Animal models of immune related diseases include both non-recombinant and recombinant (transgenic) animals. Non-recombinant animal models include, for example, rodent, e.g., murine models. Such models can be generated by introducing cells into syngeneic mice using standard techniques, e.g. subcutaneous injection, tail vein injection, spleen implantation, intraperitoneal implantation, and implantation under the renal capsule.

Animal models for delayed type hypersensitivity provides an assay of cell mediated immune function as well. Delayed type hypersensitivity reactions are a T cell mediated in vivo immune response characterized by inflammation which does not reach a peak until after a period of time has elapsed after challenge with an antigen. These reactions also occur in tissue specific autoimmune diseases such as multiple sclerosis (MS) and experimental autoimmune encephalomyelitis (EAE, a model for MS). A suitable procedure is described in detail in Current Protocols in Immunology, unit 4.5.

An animal model for arthritis is collagen-induced arthritis. This model shares clinical, histological and immunological characteristics of human autoimmune rheumatoid arthritis and is an acceptable model for human autoimmune arthritis. Mouse and rat models are characterized by synovitis, erosion of cartilage and subchondral bone. The compounds of the invention can be tested for activity against autoimmune arthritis using the protocols described in Current Protocols in Immunology, above, units 15.5. See also the model using a monoclonal antibody to CD18 and VLA-4 integrins described in Issekutz, A. C. et al., *Immunology*, (1996) 88:569. For example, in one CIA model, two groups of mice (7 to 8 week old male DBA/1 mice (Jackson Laboratory)) can be immunized intradermally with 100 µg bovine collagen type-II (BCII) (Sigma Chemical Co.) emulsified in complete Freund's adjuvant (CFA) (Difco). The mice are then rechallenged with BCII in incomplete Freund's adjuvant 21 days later. A dramatic disease with clinical signs of arthritis developed in the animals that progressed to a more severe form with time. Starting on day 24, one group of mice were injected with 100 μg of a polypeptide of interest three times per week intraperitoneally for six weeks (N=9), and a second group received 100 μg of murine IgG as a control (N=10). Animals are then monitored for the clinical signs of arthritis and at the end of the study, as described below, a radiological and histopathological examination is performed.

The mice can be examined daily for signs of joint inflammation and scored as follows: 0, normal; 1, erythema and mild swelling confined to the ankle joint; 2, erythema and mild swelling extending from the ankle to metatarsal/metacarpal joints; 3, erythema and moderate swelling extending from the ankle to the metatarsophalangeal/metacarpophalengeal joints; 4, erythema and severe swelling extending from the ankle to the digits. The maximal arthritic score per foot is 4 and the maximal disease score per mouse is 16; the mean arthritic score is calculated from all animals in the group.

For radiological analysis at the end of the study, both fore- and hind-paws can be radio-graphed using X-ray Faxitron Imaging System (Faxitron X-ray Corp., Wheeling, Ill.). Data can be digitized and pictures of radiographs prepared. The radiographs can then be examined for bone erosion and soft tissue swelling. For histo-pathological analysis, paws from the mice can be excised, fixed in 10% formalin, decalcified, and embedded in paraffin. Joint sections (6-8 μm) can be prepared and stained with hematoxylin and eosin using standard histochemical methods. Microscopic evaluation of arthritic paws can be performed in a blinded fashion. Arthritic changes in the ankle, metacarpophalangeal/metatarsophalangeal, proximal interphalangeal, and joints can be examined for articular cartilage and subchondral bone erosion.

Additionally, the compositions of the invention can be tested on animal models for psoriasis like diseases. The compounds of the invention can be tested in the scid/scid mouse model described by Schon, M. P. et al., Nat. Med., (1997) 3:183, in which the mice demonstrate histopathologic skin lesions resembling psoriasis. Another suitable model is the human skin/scid mouse chimera prepared as described by Nickoloff, B. J. et al., Am. J. Path., (1995) 146:580.

Various animal models are well known for testing anticancer activity of a candidate therapeutic composition. These include human tumor xenografting into athymic nude mice or scid/scid mice, or genetic murine tumor models such as p53 knockout mice.

One model for multiple myeloma is the human plasmacytoma xenograft mouse model (LeBlanc, R., et al. (2002) Cancer Res. 2002 62(17): 4996-5000). In this assay, immunodeficient (beige-nude-xid) mice can be used in two independent experiments. The mice are injected s.c. with e.g., $3 \times 10^7$ RPMI-8226 myeloma cells. When tumors become measurable (9.2 days; range, 6-13 days after tumor injection), mice are assigned to treatment groups receiving varying concentrations of the test polypeptide or to control groups receiving the vehicle only. Significant inhibition of tumor growth, even with some complete tumor regression, is an indicator of an therapeutic inhibitor. Significant prolongation of the median overall survival compared with controls is an indicator of an therapeutic inhibitor C. Formulations The polypeptides and compositions described herein are preferably employed in a carrier. Suitable carriers and their formulations are described in Remington's Pharmaceutical Sciences, 16th ed., 1980, Mack Publishing Co., edited by Oslo et al. Typically, an appropriate amount of a pharmaceutically-acceptable salt is used in the carrier to render the formulation isotonic. Examples of the carrier include saline, Ringer's solution and dextrose solution. The pH of the solution is preferably from about 5 to about 8, and more preferably from about 7.4 to about 7.8. It will be apparent to those persons skilled in the art that certain carriers can be more preferable depending upon, for instance, the route of administration and concentration of agent being administered. The carrier can be in the form of a lyophilized formulation or aqueous solution.

Acceptable carriers, excipients, or stabilizers are preferably nontoxic to cells and/or recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; and/or non-ionic surfactants such as TWEEN™, PLURONICS™ or polyethylene glycol (PEG).

The formulation can also contain more than one active compound as necessary for the particular indication being treated, preferably those with complementary activities that do not adversely affect each other.

The polypeptides of this invention also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Oslo, A. Ed. (1980).

The formulations to be used for in vivo administration should be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and (ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods.

D. Modes of Therapy

The polypeptides described herein are useful in treating various pathological conditions, such as immune related diseases or cancer. These conditions can be treated by inhibiting a BAFF or APRIL activity or by targeting cells expressing BAFF or APRIL for death in a mammal through administration of one or more polypeptides of the invention.

Diagnosis in mammals of the various pathological conditions described herein can be made by the skilled practitioner. Diagnostic techniques are available in the art which allow, e.g., for the diagnosis or detection of cancer or immune related disease in a mammal. For instance, cancers can be identified through techniques, including but not limited to, palpation, blood analysis, x-ray, NMR and the like. Immune related diseases can also be readily identified. In systemic lupus erythematosus, the central mediator of disease is the production of auto-reactive antibodies to self proteins/tissues and the subsequent generation of immune-mediated inflammation. Multiple organs and systems are affected clinically including kidney, lung, musculoskeletal system, mucocutaneous, eye, central nervous system, cardiovascular system, gastrointestinal tract, bone marrow and blood.

Rheumatoid arthritis (RA) is a chronic systemic autoimmune inflammatory disease that mainly involves the synovial membrane of multiple joints with resultant injury to the articular cartilage. The pathogenesis is T lymphocyte dependent and is associated with the production of rheumatoid factors, auto-antibodies directed against self IgG, with the resultant formation of immune complexes that attain high levels in joint fluid and blood. These complexes in the joint can induce the marked infiltrate of lymphocytes and monocytes into the synovium and subsequent marked synovial changes; the joint space/fluid if infiltrated by similar cells with the addition of numerous neutrophils. Tissues affected are primarily the joints, often in symmetrical pattern. However, extra-articular disease also occurs in two major forms. One form is the development of extra-articular lesions with ongoing progressive joint disease and typical lesions of pulmonary fibrosis, vasculitis, and cutaneous ulcers. The second form of extra-articular disease is the so called Felty's syndrome which occurs late in the RA disease course, sometimes after joint disease has become quiescent, and involves the presence of neutropenia, thrombocytopenia and splenomegaly. This can be accompanied by vasculitis in multiple organs with formations of infarcts, skin ulcers and gangrene. Patients often also develop rheumatoid nodules in the subcutis tissue overlying affected joints; the nodules late stage have necrotic centers surrounded by a mixed inflammatory cell infiltrate. Other manifestations which can occur in RA include: pericarditis, pleuritis, coronary arteritis, intestitial pneumonitis with pulmonary fibrosis, keratoconjunctivitis sicca, and rheumatoid nodules.

Juvenile chronic arthritis is a chronic idiopathic inflammatory disease which begins often at less than 16 years of age. Its phenotype has some similarities to RA; some patients which are rhematoid factor positive are classified as juvenile rheumatoid arthritis. The disease is sub-classified into three major categories: pauciarticular, polyarticular, and systemic. The arthritis can be severe and is typically destructive and leads to joint ankylosis and retarded growth. Other manifestations can include chronic anterior uveitis and systemic amyloidosis.

Spondyloarthropathies are a group of disorders with some common clinical features and the common association with the expression of HLA-B27 gene product. The disorders include: ankylosing sponylitis, Reiter's syndrome (reactive arthritis), arthritis associated with inflammatory bowel disease, spondylitis associated with psoriasis, juvenile onset spondyloarthropathy and undifferentiated spondyloarthropathy. Distinguishing features include sacroileitis with or without spondylitis; inflammatory asymmetric arthritis; association with HLA-B27 (a serologically defined allele of the HLA-B locus of class I MHC); ocular inflammation, and absence of autoantibodies associated with other rheumatoid disease. The cell most implicated as key to induction of the disease is the CD8+ T lymphocyte, a cell which targets antigen presented by class I MHC molecules. CD8+ T cells may react against the class I MHC allele HLA-B27 as if it were a foreign peptide expressed by MHC class I molecules. It has been hypothesized that an epitope of HLA-B27 may mimic a bacterial or other microbial antigenic epitope and thus induce a CD8+ T cells response.

Systemic sclerosis (scleroderma) has an unknown etiology. A hallmark of the disease is induration of the skin; likely this is induced by an active inflammatory process. Scleroderma can be localized or systemic; vascular lesions are common and endothelial cell injury in the microvasculature is an early and important event in the development of systemic sclerosis; the vascular injury may be immune mediated. An immunologic basis is implied by the presence of mononuclear cell infiltrates in the cutaneous lesions and the presence of antinuclear antibodies in many patients. ICAM-1 is often upregulated on the cell surface of fibroblasts in skin lesions suggesting that T cell interaction with these cells may have a role in the pathogenesis of the disease. Other organs involved include: the gastrointestinal tract: smooth muscle atrophy and fibrosis resulting in abnormal peristalsis/motility; kidney: concentric subendothelial intimal proliferation affecting small arcuate and interlobular arteries with resultant reduced renal cortical blood flow, results in proteinuria, azotemia and hypertension; skeletal muscle: atrophy, interstitial fibrosis; inflammation; lung: interstitial pneumonitis and interstitial fibrosis; and heart: contraction band necrosis, scarring/fibrosis.

Idiopathic inflammatory myopathies including dermatomyositis, polymyositis and others are disorders of chronic muscle inflammation of unknown etiology resulting in muscle weakness. Muscle injury/inflammation is often symmetric and progressive. Autoantibodies are associated with most forms. These myositis-specific autoantibodies are directed against and inhibit the function of components, proteins and RNA's, involved in protein synthesis.

Sjogren's syndrome is due to immune-mediated inflammation and subsequent functional destruction of the tear glands and salivary glands. The disease can be associated with or accompanied by inflammatory connective tissue diseases. The disease is associated with autoantibody production against Ro and La antigens, both of which are small RNA-protein complexes. Lesions result in keratoconjunctivitis sicca, xerostomia, with other manifestations or associations including bilary cirrhosis, peripheral or sensory neuropathy, and palpable purpura.

Systemic vasculitis are diseases in which the primary lesion is inflammation and subsequent damage to blood vessels which results in ischemia/necrosis/degeneration to tissues supplied by the affected vessels and eventual end-organ dysfunction in some cases. Vasculitides can also occur as a secondary lesion or sequelae to other immune-inflammatory mediated diseases such as rheumatoid arthritis, systemic sclerosis, etc., particularly in diseases also associated with the formation of immune complexes. Diseases in the primary systemic vasculitis group include: systemic necrotizing vasculitis: polyarteritis nodosa, allergic angiitis and granulomatosis, polyangiitis; Wegener's granulomatosis; lymphomatoid granulomatosis; and giant cell arteritis. Miscellaneous vasculitides include: mucocutaneous lymph node syndrome (MLNS or Kawasaki's disease), isolated CNS vasculitis, Behet's disease, thromboangiitis obliterans (Buerger's disease) and cutaneous necrotizing venulitis. The pathogenic mechanism of most of the types of vasculitis listed is believed to be primarily due to the deposition of immunoglobulin complexes in the vessel wall and subsequent induction of an inflammatory response either via ADCC, complement activation, or both.

Sarcoidosis is a condition of unknown etiology which is characterized by the presence of epithelioid granulomas in nearly any tissue in the body; involvement of the lung is most common. The pathogenesis involves the persistence of activated macrophages and lymphoid cells at sites of the disease with subsequent chronic sequelae resultant from the release of locally and systemically active products released by these cell types.

Autoimmune hemolytic anemia including autoimmune hemolytic anemia, immune pancytopenia, and paroxysmal noctural hemoglobinuria is a result of production of antibodies that react with antigens expressed on the surface of red blood cells (and in some cases other blood cells including platelets as well) and is a reflection of the removal of those antibody coated cells via complement mediated lysis and/or ADCC/Fc-receptor-mediated mechanisms.

In autoimmune thrombocytopenia including thrombocytopenic purpura, and immune-mediated thrombocytopenia in other clinical settings, platelet destruction/removal occurs as a result of either antibody or complement attaching to platelets and subsequent removal by complement lysis, ADCC or FC-receptor mediated mechanisms.

Thyroiditis including Grave's disease, Hashimoto's thyroiditis, juvenile lymphocytic thyroiditis, and atrophic thyroiditis, are the result of an autoimmune response against thyroid antigens with production of antibodies that react with proteins present in and often specific for the thyroid gland. Experimental models exist including spontaneous models: rats (BUF and BB rats) and chickens (obese chicken strain); inducible models: immunization of animals with either thyroglobulin, thyroid microsomal antigen (thyroid peroxidase).

Type I diabetes mellitus or insulin-dependent diabetes is the autoimmune destruction of pancreatic islet cells; this destruction is mediated by auto-antibodies and auto-reactive T cells. Antibodies to insulin or the insulin receptor can also produce the phenotype of insulin-non-responsiveness.

Immune mediated renal diseases, including glomerulonephritis and tubulointerstitial nephritis, are the result of antibody or T lymphocyte mediated injury to renal tissue either directly as a result of the production of autoreactive antibodies or T cells against renal antigens or indirectly as a result of the deposition of antibodies and/or immune complexes in the kidney that are reactive against other, non-renal antigens. Thus other immune-mediated diseases that result in the formation of immune-complexes can also induce immune mediated renal disease as an indirect sequelae. Both direct and indirect immune mechanisms result in inflammatory response that produces/induces lesion development in renal tissues with resultant organ function impairment and in some cases progression to renal failure. Both humoral and cellular immune mechanisms can be involved in the pathogenesis of lesions.

Demyelinating diseases of the central and peripheral nervous systems, including Multiple Sclerosis; idiopathic demyelinating polyneuropathy or Guillain-Barr syndrome; and Chronic Inflammatory Demyelinating Polyneuropathy, are believed to have an autoimmune basis and result in nerve demyelination as a result of damage caused to oligodendrocytes or to myelin directly. In MS there is evidence to suggest that disease induction and progression is dependent on T lymphocytes. Multiple Sclerosis is a demyelinating disease that is T lymphocyte-dependent and has either a relapsing-remitting course or a chronic progressive course. The etiology is unknown; however, viral infections, genetic predisposition, environment, and autoimmunity all contribute. Lesions contain infiltrates of predominantly T lymphocyte mediated, microglial cells and infiltrating macrophages; CD4+ T lymphocytes are the predominant cell type at lesions. The mechanism of oligodendrocyte cell death and subsequent demyelination is not known but is likely T lymphocyte driven.

Inflammatory and Fibrotic Lung Disease, including Eosinophilic Pneumonias; Idiopathic Pulmonary Fibrosis, and Hypersensitivity Pneumonitis may involve a disregulated immune-inflammatory response. Inhibition of that response would be of therapeutic benefit.

Autoimmune or Immune-mediated Skin Disease including Bullous Skin Diseases, Erythema Multiforme, and Contact Dermatitis are mediated by auto-antibodies, the genesis of which is T lymphocyte-dependent.

Psoriasis is a T lymphocyte-mediated inflammatory disease. Lesions contain infiltrates of T lymphocytes, macrophages and antigen processing cells, and some neutrophils.

Allergic diseases, including asthma; allergic rhinitis; atopic dermatitis; food hypersensitivity; and urticaria are T lymphocyte dependent. These diseases are predominantly mediated by T lymphocyte induced inflammation, IgE mediated-inflammation or a combination of both.

Transplantation associated diseases, including Graft rejection and Graft-Versus-Host-Disease (GVHD) are T lymphocyte-dependent; inhibition of T lymphocyte function is ameliorative.

Other diseases in which intervention of the immune and/or inflammatory response have benefit are Infectious disease including but not limited to viral infection (including but not limited to AIDS, hepatitis A, B, C, D, E) bacterial infection, fungal infections, and protozoal and parasitic infections (molecules (or derivatives/agonists) which stimulate the MLR can be utilized therapeutically to enhance the immune response to infectious agents), diseases of immunodeficiency (molecules/derivatives/agonists) which stimulate the MLR can be utilized therapeutically to enhance the immune response for conditions of inherited, acquired, infectious induced (as in HIV infection), or iatrogenic (i.e. as from chemotherapy) immunodeficiency), and neoplasia.

The polypeptides of this invention can be administered in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Optionally, administration can be performed through mini-pump infusion using various commercially available devices. The polypeptides of this inventino can also be employed using gene therapy techniques which have been described in the art.

Effective dosages and schedules for administering the polypeptides of this invention can be determined empirically, and making such determinations is within the skill in the art. Single or multiple dosages can be employed. It is presently believed that an effective dosage or amount of a polypeptide of this invention used alone can range from about 1 ng/kg to about 100 mg/kg of body weight or more per day. Interspecies scaling of dosages can be performed in a manner known in the art, e.g., as disclosed in Mordenti et al., *Pharmaceut. Res.*, 8:1351 (1991).

When in vivo administration of a polypeptide of this invention thereof is employed, normal dosage amounts can vary from about 10 ng/kg to up to 100 mg/kg of mammal body weight or more per day, preferably about 1 µg/kg/day to 10 mg/kg/day, depending upon the route of administration.

Guidance as to particular dosages and methods of delivery is provided in the literature; see, for example, U.S. Pat. Nos. 4,657,760; 5,206,344; or 5,225,212. It is anticipated that different formulations will be effective for different treatment compounds and different disorders, that administration targeting one organ or tissue, for example, can necessitate delivery in a manner different from that to another organ or tissue. Those skilled in the art will understand that the dosage of polypeptide that must be administered will vary depending on, for example, the mammal which will receive the agonist or antagonist, the route of administration, and other drugs or therapies being administered to the mammal.

Depending on the type of cells and/or severity of the disease, about 1 ng/kg to 15 mg/kg (e.g. 0.1-20 mg/kg) of polypeptide is an initial candidate dosage for administration, whether, for example, by one or more separate administrations, or by continuous infusion. A typical daily dosage might range from about 1 ng/kg to 100 mg/kg or more, depending on the factors mentioned above. For repeated administrations over several days or longer, depending on the condition, the treatment is sustained until a desired suppression of disease symptoms occurs. However, other dosage regimens can be useful.

Optionally, prior to administration of any polypeptide, the mammal or patient can be tested to determine levels or activity of APRIL or BAFF. Such testing can be conducted by ELISA or FACS of serum samples or peripheral blood leukocytes.

It is contemplated that yet additional therapies can be employed in the methods. The polypeptide of this invention (and one or more other therapies) can be administered concurrently or sequentially. The one or more other therapies can include but are not limited to, administration of radiation therapy, cytokine(s), growth inhibitory agent(s), chemotherapeutic agent(s), cytotoxic agent(s), tyrosine kinase inhibitors, ras farnesyl transferase inhibitors, angiogenesis inhibitors, and cyclin-dependent kinase inhibitors. In addition, therapies based on therapeutic antibodies that target tumor antigens such as Rituxan™ or Herceptin™ as well as anti-angiogenic antibodies such as anti-VEGF.

Preparation and dosing schedules for chemotherapeutic agents can be used according to manufacturers' instructions or as determined empirically by the skilled practitioner. Preparation and dosing schedules for such chemotherapy are also described in *Chemotherapy Service Ed.*, M. C. Perry, Williams & Wilkins, Baltimore, Md. (1992). The chemotherapeutic agent can precede, or follow administration of, e.g. a polypeptide of this invention, or can be given simultaneously therewith. The polypeptide of this invention can also be combined with an anti-oestrogen compound such as tamoxifen or an anti-progesterone such as onapristone (see, EP 616812) in dosages known for such molecules.

It can be desirable to also administer antibodies against other antigens, such as antibodies which bind to CD20, CD11a, CD18, CD40, ErbB2, EGFR, ErbB3, ErbB4, or vascular endothelial factor (VEGF). Alternatively, or in addition, two or more antibodies binding the same or two or more different antigens disclosed herein can be co-administered to the patient. Sometimes, it can be beneficial to also administer one or more cytokines to the patient. In one embodiment, the antagonists herein are co-administered with a growth inhibitory agent. For example, the growth inhibitory agent can be administered first, followed by a polypeptide of the present invention.

E. Methods of Screening

The invention also encompasses methods of identifying inhibitors of BAFF or APRIL binding to their receptors. Such molecules can comprise small molecules or polypeptides, including antibodies. Examples of small molecules include, but are not limited to, small peptides or peptide-like molecules, preferably soluble peptides, and synthetic non-peptidyl organic or inorganic compounds. The screening assays for drug candidates are designed to identify compounds or molecules that bind or complex with the polypeptides identified herein, or otherwise interfere with the interaction of these polypeptides with other cellular proteins. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

Assays for, for instance, identifying inhibitors are common in that they call for contacting the drug candidate with a polypeptide of this invention under conditions and for a time sufficient to allow these two components to interact.

In binding assays, the interaction is binding and the complex formed can be isolated or detected in the reaction mixture. In a particular embodiment, the polypeptide identified herein or the drug candidate is immobilized on a solid phase, e.g., on a microtiter plate, by covalent or non-covalent attachments. Non-covalent attachment generally is accomplished by coating the solid surface with a solution of the polypeptide and drying. Alternatively, an immobilized antibody, e.g., a monoclonal antibody, specific for the polypeptide to be immobilized can be used to anchor it to a solid surface. The assay is performed by adding the non-immobilized component (e.g., drug candidate), which can be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the non-immobilized component.

Compounds or molecules that interfere with the interaction of BAFF and its receptors and APRIL and its receptors and other intra- or extracellular components can be tested as follows: usually a reaction mixture is prepared containing a polypeptide of this invention under conditions and for a time allowing for the interaction and binding of the two products. To test the ability of a candidate compound to inhibit binding, the reaction is run in the absence and in the presence of the test compound. In addition, a placebo can be added to a third reaction mixture, to serve as positive control. The binding (complex formation) between the test compound and the polypeptide of this invention is monitored. The formation of a complex in the control reaction(s) but not in the reaction mixture containing the test compound indicates that the test compound interferes with the interaction of the test compound and its reaction partner.

The polypeptides of this invention can also be evaluated to determine the strength of their activity using assays known in the art. According to one embodiment, a method of identifying a BAFF inhibitor is a NF-κb2/100 processing assay in splenic B cells. According to a further embodiment, the NF-κb2/100 processing assay is performed as follows: splenic B cells from mice are isolated using MACS beads (Miltenyi). The B cells are cultured for 24 hours in the presence or absence of recombinant BAFF (2 nM) which has been preincubated for 30 min at room temperature with the polypeptide to be tested or a control (e.g., native BCMA polypeptide—as a positive inhibitory control). Thereafter, the B cells are lysed. The lysates (10 μg) are subjected to Western blot analysis with anti-NF-κB2 or anti-βactin antibodies. See Kayagaki, N et al., (2002) *Immunity* 10:515-524. An inhibitor in this assay will decrease the processing of NF-κb2/100 to p52 protein.

In another assay, a BCMA-DR4 chimeric receptor (the extracellular domain of human DR4 replaced with that of a BCMA polypeptide) is used in an apoptosis assay. HeLa cells can be used for stable expression of BCMA-DR4. Addition of BAFF or APRIL triggers apoptosis due to activation of the BCMA-DR4 chimeric receptor. The cell based screening is based on the fact that BAFF antagonists or APRIL antagonists should prevent BAFF or APRIL induced cell death. HeLa cells expressing BCMA-DR4 would be seeded into 12-well plate 16 hours before the assay. Purified recombinant BAFF or APRIL (10 ng/ml) is first preincubated with the agents to be tested (e.g., a polypeptide of this invention) for 30 min at room temperature prior to addition to the cells expressing BCMA-DR4. 8 to 16 hours after addition of BAFF or APRIL, cell death is quantified by Trypan-Blue assay.

F Articles of Manufacture

In another embodiment of the invention, an article of manufacture containing materials useful for the treatment of the disorders described above is provided. The article of manufacture comprises a container and a label and a polypeptide or nucleic acid of this invention. Suitable containers include, for example, bottles, vials, syringes, and test tubes. The containers can be formed from a variety of materials such as glass or plastic. The container holds a composition which is effective for treating the condition and can have a sterile access port (for example the container can be an intravenous solution bag or a vial having a stopper pierceable by a hypodermic injection needle). The active agents in the composition comprises a polypeptide of this invention alone or in combination with an additional therapeutic agent. Examples of an additional therapeutic agent includes, chemotherapeutic agents, cytotoxic agents, etc. The label on, or associated with, the container indicates that the composition is used for treating the condition of choice. The article of manufacture can further comprise a second container comprising a pharmaceutically-acceptable buffer, such as phosphate-buffered saline, Ringer's solution and dextrose solution. It can further include other materials desirable from a commercial and user standpoint, including other buffers, diluents, filters, needles, syringes, and package inserts with instructions for use.

Commercially available reagents referred to in the Examples were used according to manufacturer's instructions unless otherwise indicated. The source of those cells identified in the following Examples, and throughout the specification, by ATCC accession numbers is the American Type Culture Collection, Manassas, Va. Unless otherwise noted, the present invention uses standard procedures of recombinant DNA technology, such as those described hereinabove and in the following textbooks: Sambrook et al, supra; Ausubel et at, *Current Protocols in Molecular Biology* (Green Publishing Associates and Wiley Interscience, N.Y., 1989); Innis et al., *PCR Protocols: A Guide to Methods and Applications* (Academic Press, Inc.: N.Y., 1990); Harlow et al., *Antibodies: A Laboratory Manual* (Cold Spring Harbor Press: Cold Spring Harbor, 1988); Gait, *Oligonucleotide Synthesis* (IRL Press: Oxford, 1984); Freshney, *Animal Cell Culture,* 1987; Coligan et al., *Current Protocols in Immunology,* 1991.

Throughout this specification and claims, the word "comprise," or variations such as "comprises" or "comprising," will be understood to imply the inclusion of a stated integer or group of integers but not the exclusion of any other integer or group of integers.

The foregoing written description is considered to be sufficient to enable one skilled in the art to practice the invention. The following Examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

EXAMPLES

Example 1

Materials and Methods

The reagents listed below were obtained from the following sources: o-Phenylenediamine dihydrochloride (OPD) (Sigma), Streptavidin peroxidase (POD) (Roche/Boehringer Mannheim), IgG-horse radish peroxidase (HRP) (Jackson Immuno Research Laboratories) Protease Complete (Boehringer Mannheim), anti-M13-HRP (Boehringer Mannheim), sulpho NHS-biotin (Pierce). Human BR3-Fc (Pelletier, M., et al., (2003) *J Biol Chem* 278, 33127-33133) was a kind gift from Y.-M. Hsu (Biogen). BR3-Fc contains the first 70 amino acids of human BR3 extracellular domain, carrying Val20->Asn and Leu27->Pro mutations, fused with a human IgG1 Fc domain.

$BAFF_{82-285}$ production. Human BAFF was expressed and purified as previously described (Gordon, N. C., et al., (2003) *Biochemistry* 42, 5977-5983). Briefly, a DNA fragment encoding human BAFF (residues 82-285) was cloned into the pET15b (Novagen) expression vector, creating a fusion with an N-terminal His-tag followed by a thrombin cleavage site. *E. coli* BL21(DE3) (Novagen) cultures were grown to mid-log phase at 37 C in LB medium with 50 mg/L carbenicillin and then cooled to 16° C. prior to induction with 1.0 mM IPTG. Cells were harvested by centrifugation after 12 hours of further growth and stored at −80° C. The cell pellet was resuspended in 50 mM Tris, pH 8.0, and 500 mM NaCl and sonicated on ice. After centrifugation, the supernatant was loaded onto a Ni-NTA agarose column (Qiagen). The column was washed with 50 mM Tris, pH 8.0, 500 mM NaCl, and 20 mM imidazole and then eluted with a step gradient in the same buffer with 250 mM imidazole. BAFF-containing fractions were pooled, thrombin was added, and the sample was dialyzed overnight against 20 mM Tris, pH 8.0, and 5 mM $CaCl_2$ at 4° C. The protein was further purified on a monoQ (Pharmacia) column and finally on an S-200 size exclusion column in 20 mM Tris, 150 mM NaCl, and 5 mM $MgCl_2$. The resulting BAFF protein was used as described below.

APRIL expression and production. A PCR product coding for amino acids K104-L241 of murine APRIL was subcloned into the XbaI/NotI sites of a pET-32aΔEK, a modified PET-32a vector (Novagen) with a deleted S-Tag and enterokinase site (basepairs 5602-5683) to generate an N-terminal thioredoxin (TRX) fusion protein. The pET-32a-APRIL(K104-L241) was transformed into Origami (DE3) competent cells (Novagen). Overnight cultures were diluted 1:100 and grown at room temperature (RT) in LB media with 50 μg/ml carbenicillin to an $A_{600}$ of 0.8 with vigorous shaking. IPTG was added to a final concentration of 1 mM for induction and cultures were grown overnight at 25° C. One liter of frozen cell pellet was resuspended in 100 ml Buffer A (50 mM Tris-HCl, pH 7.6, 300 mM NaCl, 0.5 mM PMSF, 2 mM benzamidine) with 5 mM imidazole and placed on ice for 30 min. Cells were homogenized by passage through a microfluidizer, and centrifuged at 15,000 rpm for 45 min. Supernatant was loaded onto a 3 ml Ni-NTA agarose column (Qiagen), washed with 10 column volumes of Buffer A with 10 mM imidazole, and eluted with 10 column volumes of Buffer A with 300 mM imidazole. Fractions containing TRX-APRIL fusion protein were pooled, concentrated and purified by Superdex 200 size exclusion chromatography.

Baculovirus expression and purification of BCMA ECD. DNA coding for residues 4-53 (M4 to N53) of the human BCMA extracellular domain (ECD) was amplified by PCR and subcloned into the vector pET15b (Novagen) using the NdeI and XhoI restriction sites to introduce an N-terminal His tag, and a thrombin cleavage sequence preceding the BCMA coding region. This His-tagged BCMA construct was subcloned into the baculovirus transfer vector pAcGP67B (Pharmingen) using the BamHI and NotI restriction sites. The transfer vector was co-transfected with BaculoGold DNA into Sf9 cells and recombinant virus subsequently isolated and amplified to facilitate protein production. After three days of growth of virally infected Hi5 cells at 27° C., his-tagged protein was purified from the culture medium by chromatography on Ni-NTA resin as described previously (Hymowitz, S. G., et al, (2001) Embo J 20, 5332-5341), followed by gel filtration on a Superdex 75 column. BCMA eluted from the Superdex 75 column as a monomer. N-terminal sequencing and mass spectrometry were used to confirm the proper identity of the purified protein and the presence of both glycosylated and non-glycosylated species in the purified protein pool, respectively.

Expression and purification of BCMA-Z fusion proteins. Plasmid BCMA-Z, designed to express a protein fusion of BCMA ECD (residues 5-50) and the Z domain of Staphylococcal protein A (Nilsson, B., et al., (1987) Protein Eng 1, 107-113) was constructed by using PCR to replace the amber stop and gene 3 portion of BCMA1-g3 with the Z domain fragment from plasmid pZCT (Starovasnik, M. A., et al., (1999) Protein Sci 8, 1423-1431). For these experiments, the Z domain contained the following sequence:

(SEQ ID NO: 29)
AQHDEAVDNKFNKEQQNAFYEILHLPNLNEEQRNAFIQSLKDDPSQSANL

LAEAKKLNDAQAPK

Oligonucleotide-directed mutagenesis was performed as described (Kunkel, T. A., et al., (1987) Methods Enzymol 154, 367-382) to generate point mutations in the BCMA sequence and all constructs were verified by DNA sequencing. BCMA-Z and mutant BCMA-Z fusion proteins were expressed by secretion from E. coli and purified by chromatography on IgG-Sepharose as described previously (Starovasnik, M. A., et al., (1996) Biochemistry 35, 15558-15569). BCMA-Z and mutant BCMA-Z fusion proteins were further purified by size exclusion chromatography on a HiPrep 16/60 Sephacryl S-100 HR column. BCMA-Z had an elution volume from the S-100 column between that of soluble human tissue factor (MW=24800) and E. coli thioredoxin (MW=11675). A molar mass of 12,000, consistent with the monomer MW of 13017 calculated from the amino acid sequence, was calculated from light scattering data collected on a miniDAWN detector (Wyatt Technologies). Amino acid analysis was performed on the purified BCMA-Z to determine the extinction coefficient ($\epsilon_{280}$=9832 M$^{-1}$ cm$^{-1}$).

Competitive displacement ELISA. BCMA, BCMA mutants and BR3 polypeptides were tested for binding to either APRIL or BAFF in a competition ELISA assay. A 100 µl solution of carbonate buffer (pH 9.6) containing 2 µg/ml target ligand, either APRIL or BAFF, was coated on Nunc Maxisorp 96 well plates overnight at 4° C. The plate was washed with PBS and blocked for 1 hr with 200 µl of 0.2% BSA in PBS. In one set of experiments, BCMA-Z was added for a final concentration of 0.2 µg/ml to three-fold serial dilutions of ligand that were prepared in a 96 well plate containing PBS/0.05% Tween-20 and incubated for 1 hr at room temperature. After washing the coated plate with PBS/0.05% Tween-20, 100 µl/well of each dilution was transferred to the washed plate and incubated for 1 hr at room temperature. The plate was then washed with PBS/0.05% Tween-20 and incubated with 100 µl/well of 1:3000 dilution of IgG-HRP for 1 hr at room temperature to detect bound BCMA-Z through the Z domain-IgG interaction. After washing plate with PBS/0.05% Tween-20 followed by final wash in PBS, the plate was incubated for 5 min at room temperature with 100 µl/well PBS substrate solution containing 0.8 mg/ml OPD (Sigma) and 0.01% $H_2O_2$. The reaction was quenched with 100 µl/well of 1M $H_3PO_4$ and the plate was read at 492 nm. See FIG. 1A. To account for background signal, 100 µl/well of each dilution was also transferred to uncoated wells blocked with 0.2% BSA in PBS and then processed as described above.

In a variation of the above ELISA, three-fold serial dilutions of receptors were prepared in PBS/0.05% Tween-20 with 7 pM biotinylated BCMA-Z (when APRIL was the target) or 0.3 pM biotinylated "miniBR3", BR3 residues 17-42, (when BAFF was the target). MiniBR3 was prepared and biotinylated as described previously (Gordon, N. C., et al., (2003) Biochemistry 42, 5977-5983). For BCMA-Z biotinylation, 20 µg of purified BCMA-Z was incubated with a 3-fold molar excess of biotin-sulphoNHS (Pierce) in PBS at 25° C. for 3 hrs and then quenched with a 10-fold molar excess of Tris-HCl, pH 7.5. After washing the NUNC plate coated with either APRIL or BAFF with PBS/Tween-20, 100 µl/well of each receptor dilution was transferred and incubated for 1 hr at room temperature. The plate was washed with PBS/Tween-20 and incubated with 100 µl/well of 0.1 U/ml Streptavidin-POD (Boehringer Mannheim) for 15 min. The peroxidase signal was developed and detected as described above. To account for background signal, 100 µl/well of each dilution was also transferred to uncoated wells blocked with 0.2% BSA in PBS and then processed as described above.

Measurement of binding constants for receptors to ligands. Surface plasmon resonance (SPR) measurements on a BIAcore 3000 instrument (Pharmacia Biosensor) were used to measure binding affinities of receptors to immobilized APRIL and BAFF. CM5 chips from BIAcore were docked according to manufacturer instructions. Then, BIAcore system was primed with 0.2 µm filtered buffer containing 10 mM Hepes pH 7.2, 150 mM NaCl, 0.005% Tween20. After buffer priming, the flow cells were normalized with 70% glycerol. Each flow cell surface was activated individually in preparation for linkage of the ligand to the chip with a 1:1 mixture of EDC(N-ethyl-N'-(3-dimethyl aminopropyl)-carbodiimide hydrochloride) and NHS(N-hydroxysuccinimide). In this instance, the ligand is the immobilized component (e.g., APRIL or BAFF) and the analyte (e.g., BCMA or BR3) is the component whose binding is being measured. Generally, the ligand to be immobilized (30 µg/ml in 10 mM NaOAc, pH 5 buffer) was injected into the system at 40 µl/min. Once approximately 400 RU was generated, the flow cell was blocked with ethanolamine. For use as a control, one activated flow cell that had not been conjugated with anything was also blocked with ethanolamine. The system was then primed again.

50 µl samples of analyte ranging in concentration from 6.25 nM to 200 nM in 2-fold increments were injected over flow cells at a flow rate of 30 µl/min. The ligand-receptor complex was allowed to dissociate by washing the flow cell at 30 µl/min for 600 seconds. Alternatively, if several binding measurements over the same flow cell were to be performed, the ligand-receptor complex was allowed to dissociate by washing the flow cell at 30 µl/min for 900 seconds. Sensorgrams were recorded for each binding assay. A 1:1 Langmuir binding equation was used to simultaneously fit the association and dissociation rates of the ligand-analyte interactions. $k_a$, $k_d$, $K_D$ were calculated using curve fit analysis software provided with the BiaCore instrument Example 2

Binding Assays with Monomers and Dimers of BCMA

Previous reports on the interaction of BCMA with BAFF utilizing dimeric BCMA constructs (BCMA-Fc) have indicated a high affinity interaction with $K_D$ values of about 1 nM (Marsters, S. A., et al., (2000) *Curr Biol* 10, 785-788; Yu, G., et al., (2000) *Nat Immunol* 1, 252-256). More recently, studies with monovalent BCMA-Fc have indicated a much weaker affinity for BAFF (Pelletier, M., et al., (2003) *J Biol Chem* 278, 33127-33133). In this study, monomeric BCMAs were produced and their affinities for both BAFF and APRIL were measured. Monomeric BCMA was used in the form of a BCMA ECD purified from baculovirus expression or a protein containing a BCMA ECD fused to the Z domain of Protein A (BCMA-Z) purified from secretions of *E. coli* as in Example 1 Although human BCMA and human BAFF were used in these experiments, murine APRIL was used since the murine protein is much better behaved than the human protein in vitro. Murine and human APRIL share >80% sequence identity and the putative receptor-binding residues are absolutely conserved. APRIL was expressed and purified as a thioredoxin fusion protein as described in Example 1. All binding experiments were done with the intact fusion protein since removal of the thioredoxin by limited proteolysis resulted in reduced solubility. The binding affinity for monomeric human BCMA-Z to murine APRIL and human BAFF was measured by competition ELISA as described in Example 1.

Figure 1B:
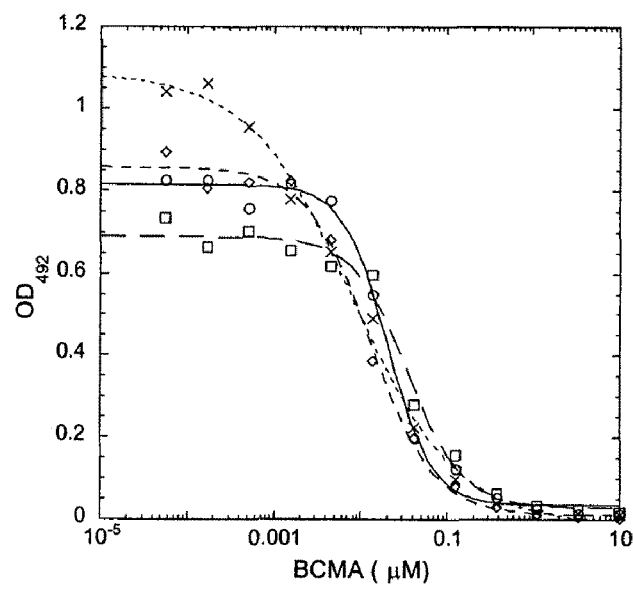
Figure 1C:
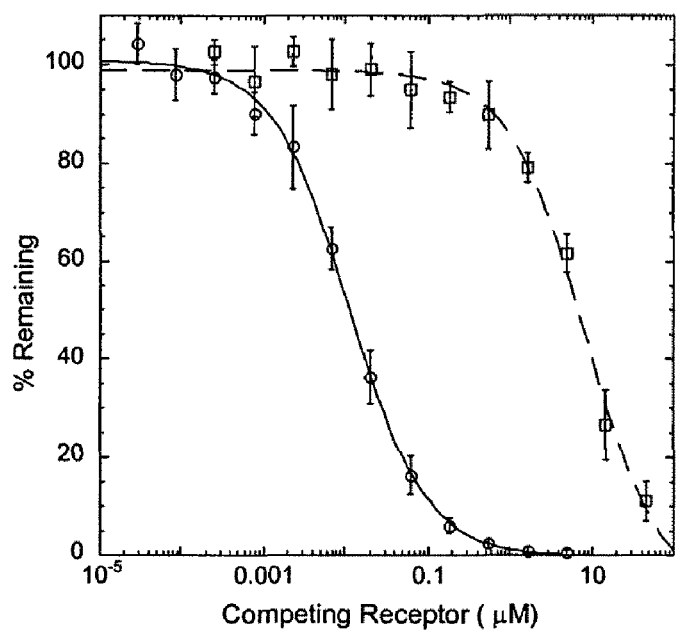

APRIL in solution was able to compete for binding to BCMA-Z with immobilized APRIL with an $IC_{50}$ of 20 nM whereas BAFF in solution competed for BCMA-Z binding with immobilized BAFF with an $IC_{50}$ of >65 µM (FIG. 1A). Comparison of APRIL binding affinity for BCMA-Z and BCMA from baculovirus expression in a competition ELISA shows that the Z domain does not influence the measured affinity (FIG. 1B). This equivalent binding allowed the remaining BCMA binding measurements to be made using BCMA-Z. A competition ELISA measuring BCMA-Z binding to APRIL and BAFF using biotinylated BCMA-Z (for APRIL binding) or biotinylated miniBR3 (Gordon, N. C., et al., (2003) *Biochemistry* 42, 5977-5983) (for BAFF binding) confirms that the affinity measurements of BCMA-Z binding to receptors (FIG. 1C) are consistent with the ligand competition data: $IC_{50}$ values of BCMA-Z binding to APRIL ($IC_{50}$=11 nM) are about 1000-fold higher in affinity than BCMA-Z binding to BAFF ($IC_{50}$=8 µM for BAFF).

Figure 2A:
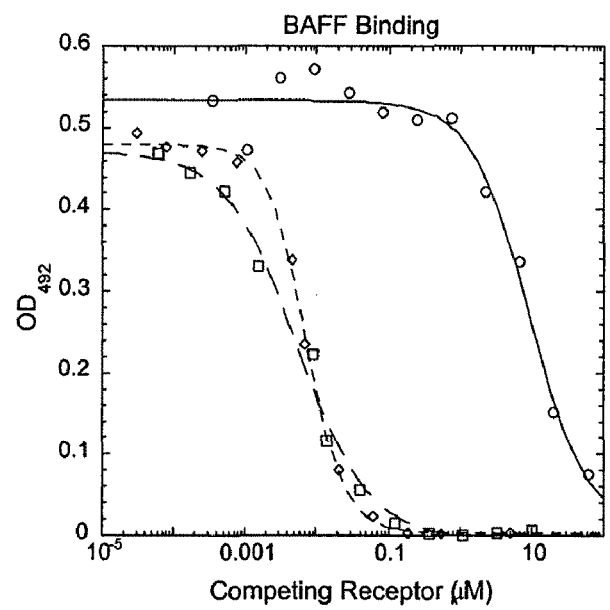
FIG. 2A-B. Comparison of monovalent and bivalent receptors for binding to immobilized ligand. A. Displacement of biotinylated mini-BR3 binding to immobilized BAFF by BCMA-Z (circle), BCMA-Fc (square), or BR3-Fc (diamond). B. Inhibition of biotinylated BCMA-Z binding to immobilized APRIL by BCMA-Z (circle), BCMA-Fc (square), or BR3-Fc (diamond).
Figure 2B:
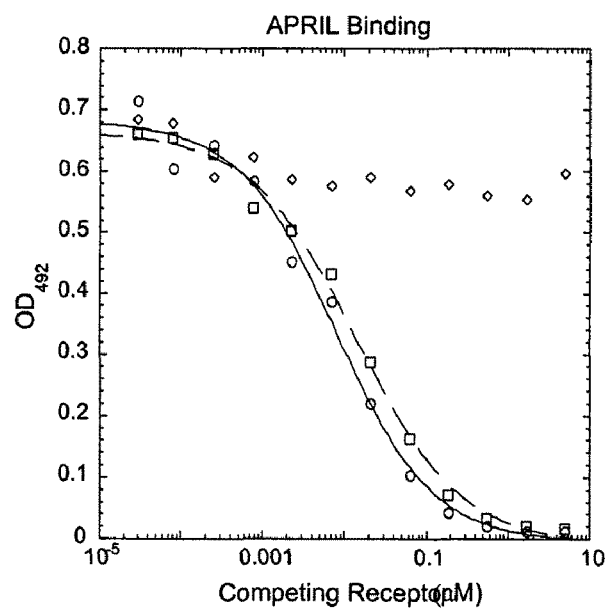

Since previously reported binding affinities of BCMA-BAFF interaction have been reported to be in the low nM range (Marsters, S. A., et al., (2000) *Curr Biol* 10, 785-788; Yu, G., et al., (2000) *Nat Immunol* 1, 252-256; Pelletier, M., et al., (2003) *J Biol Chem* 278, 33127-33133), a comparison of various receptor constructs and ligands was done to examine the effects of avidity on receptor binding to APRIL and BAFF. FIG. 2 compares binding affinities of BCMA-Z, BCMA-Fc, and BR3-Fc to either APRIL (FIG. 2A) or BAFF (FIG. 2B). These data reveal that the monovalent BCMA-Z binds to BAFF ($IC_{50}$=9 µM) with a 1000-fold reduced affinity compared to APRIL ($IC_{50}$=7 nM), while BCMA-Fc, a bivalent construct, binds to both APRIL and BAFF with low nM affinity ($IC_{50}$=5 nM and 13 nM, respectively). BR3-Fc binds BAFF, its predicted physiological ligand, with $IC_{50}$=7 nM, but has no measurable affinity for APRIL.

The ligand binding affinity of BCMA was also measured by surface plasmon resonance. APRIL and BAFF were selected for immobilization due to non-specific interactions of APRIL with the sensor chip surface when used in the mobile phase. Table 5 summarizes the kinetics data for BCMA-Z and BCMA-Fc.

TABLE 5

| Receptor-Ligand | $k_a$ ($\times 10^{-5} M^{-1} s^{-1}$) | $k_d$ ($\times 10^3 s^{-1}$) | $K_D$ (nM) |
|---|---|---|---|
| BCMA-Fc-APRIL | 31.2 | 0.1 | 0.2 |
| BCMA-Z-APRIL | 8.5 | 4.7 | 5.5 |
| BCMA-Fc-BAFF | 6.8 | 3.4 | 4.9 |
| BCMA-Z-BAFF | NMB | NMB | NMB |
| BCMA(baculovirus)-BAFF | NMB | NMB | NMB |

Table 5. Binding constants for receptor binding to ligands. Association ($k_a$) and dissociation ($k_d$) rate constants, and dissociation constants ($K_D$) were calculated by nonlinear regression analysis using a 1:1 binding model. NMB signifies no measurable binding.

BCMA-Z bound to immobilized APRIL with a $K_D$ of 5.5 nM whereas binding to BAFF was not detectable. BAFF-binding by BCMA ECD produced via baculovirus expression was also undetectable. In contrast, BCMA-Fc bound to both BAFF ($K_D$=4.9 nM) and APRIL ($K_D$=0.2 nM) with high affinity, consistent with the competition ELISA result. BCMA-Fc binding to immobilized APRIL gave a faster on-rate with a slower off-rate than measured for the BCMA-Z-APRIL interaction, as expected for a bivalent molecule where avidity contributes to binding.

Monovalent BCMA binds APRIL with high affinity. In contrast, the affinity for BAFF is 1000-fold weaker than for APRIL. Since the BCMA produced in *E. coli* binds APRIL with high affinity, and is equivalent to material produced by expression in insect cells, the weak affinity for BAFF cannot be explained by a misfolding of BCMA-Z. This study is believed to be the first report of a high affinity interaction between monovalent BCMA and APRIL. Consistent with earlier studies (Marsters, S. A., et al., (2000) *Curr Biol* 10, 785-788; Yu, G., et al., (2000) *Nat Immunol* 1, 252-256; Pelletier, M., et al., (2003) *J Biol Chem* 278, 33127-33133), the bivalent protein (BCMA-Fc) binds BAFF with an apparent high affinity. Ah avidity component originating from a bivalent receptor interacting with a ligand having three binding sites can enhance the apparent affinity. Thus, it is likely that BAFF may bind with high affinity to cells expressing BCMA only if the receptors are pre-organized on the cell surface. Although it has been proposed that FAS and TNFR1 can form homo-oligomers on the cell surface in the absence of ligand (Chan, F. K., et al., (2000) *Science* 288, 2351-2354), BCMA appears to lack the pre-ligand assembly domain ("PLAD") necessary for this association. Under normal physiological conditions, endogenous BCMA may naturally operate only as a receptor for APRIL and not for BAFF.

Example 3

BCMA Mutational Analysis

A shotgun alanine scan (Weiss, G. A., et al., (2000) *Proc Natl Acad Sci USA* 97, 8950-8954) of the single extracellular cysteine rich domain (CRD) of BCMA was used to determine the contribution of individual amino acid side chains to the binding of either APRIL or BAFF. This was carried out by generating phage display libraries expressing the BCMA mutants made by shotgun alanine scan and screening phage display libraries for those that bound to APRIL and/or BAFF.

Library construction. An initial vector for phage display of the BCMA extracellular domain was prepared by PCR subcloning of the fragment encoding residues 5-50 (A5 to K51) into the phagemid sTF-g3 (Lee, G. F., and Kelley, R. F. (1998) *J Biol Chem* 273, 4149-4154). The resulting construct (BCMA1-g3) contained residues 5-50 fused at the C-terminus to a tripeptide (G-S-A) linker and an amber stop codon followed by the C-terminal half of the M13 p3 coat protein. The bacterial signal sequence stII was joined to the N-terminus of BCMA with an inserted Ser residue comprising the P1' cleavage site for the signal peptidase. Expression was driven by the alkaline phosphatase promoter. Phagemid BCMA2-g3 was prepared by using site-directed mutagenesis (Kunkel, T. A., et al., (1987) *Methods Enzymol* 154, 367-382) to insert the peptide epitope (MADPNRFRGKDLGG) (SEQ ID NO:32) for an antibody (3C8:2F4, Genentech, Inc.) between the P1 and P1' residues of the signal sequence cleavage site. In order to generate phage libraries that were completely represented by the phage pool, the ECD was divided into two distinct libraries as described below.

BCMA2-g3 phagemid was used to prepare two "shotgun alanine" scanning libraries essentially as described previously (Weiss, G. A., et al., (2000) *Proc Natl Acad Sci USA* 97, 8950-8954). In these libraries, certain wild-type codons were replaced by degenerate codons within amino acid positions 7-36 in the BCMA ECD (except cysteines and alanines) resulting in either the wild-type amino acid or alanine or a few alternative amino acids being expressed at the selected sites. More specifically, each library, prepared separately, contained shotgun codons at the following positions: library 1 has shotgun codons at positions 7, 9, 10, 11, 12, 13, 14, 15, 16, 17, 18, 19, library 2 has shotgun codons at positions 22, 23, 25, 26, 27, 29, 30, 31, 32, 33, 34, 35, 36. These sites were chosen for mutagenesis on the basis of their proximity to BAFF in the BCMA-BAFF crystal structure (Liu, Y., et al., (2003) *Nature* 423, 49-56) and because of their structural equivalence to residues found important for BAFF-binding in a shotgun scan of BR3 (Gordon, N. C., et al., (2003) *Biochemistry* 42, 5977-5983). The shotgun codon substituted at each wild-type position was as follows:

| Amino acid | Shotgun codon* | Shotgun substitutions |
|---|---|---|
| C | KST | A/C/G/S |
| D | GMT | A/D |
| E | GMA | A/E |
| F | KYT | A/F/S/V |
| G | GST | A/G |
| H | SMT | A/H/D/P |
| I | RYT | A/I/T/V |
| K | RMA | A/K/E/T |
| L | SYT | A/L/P/V |
| M | RYG | A/M/T/V |
| N | RMC | A/N/D/T |
| P | SCA | A/P |
| Q | SMA | A/Q/E/P |
| R | SST | A/R/G/P |
| S | KCC | A/S |
| T | RCT | A/T |
| V | GYT | A/V |
| W | KSG | A/W/G/S |
| Y | KMT | A/Y/D/S |

For each amino acid, the appropriate shotgun codon ideally encoded only the wt amino acid or alanine, but the nature of the genetic code necessitates the occurrence of two other amino acids for some shotgun substitutions. Single-letter amino acid and nucleotide abbreviations are used. *DNA degeneracies are represented by IUB code (K=G/T, M=A/C, N=A/C/G/T, R=A/G, S=G/C, W=A/T, Y=C/T). Thus, for positions where the wild-type residue is Arg, Asn, Gln, His, Ile, Leu, Phe, or Tyr, the shotgun code allows for two additional amino acid substitutions. Each library contained at least $1 \times 10^{11}$ phage/ml, allowing for complete representation of the theoretical diversity ($>10^5$-fold excess) [library 1 codes $1 \times 10^6$ unique sequences, library 2 codes $5.2 \times 10^5$ unique sequences].

Library sorting and analysis. The BCMA phage libraries were individually subjected to two types of selection: target ligand selection (BAFF or APRIL), and display selection by binding to an antibody (e.g., 3C8:2F4 (Genentech, Inc.)) that recognizes an epitope tag N-terminally displayed on all BCMA library members (Skelton, N. J., et al., (2003) *J Biol Chem* 278, 7645-7654). Display selection is important for normalizing BAFF- and APRIL-binding selection with respect to expression differences between libraries. BAFF, APRIL, or anti-tag antibody, 3C8:2F4, were immobilized on 96-well Nunc Maxisorp immunoplates (Sidhu, S. S. (2001) *Biomol Eng* 18, 57-63). BSA-coated wells were used to determine non-specific background binding. Phage was diluted to $1 \times 10^9$ phage/ml in PBS/0.05% Tween 20/0.2% BSA and bound at room temperature for 2 hours with gentle shaking. After incubation, phage solutions were discarded and bound phage were washed ten times with PBS/0.05% Tween 20. Bound phage were eluted by incubating each well with 100 µl of 100 mM HCl for 5 minutes at room temperature. Phage eluted from each target were neutralized with 2M Tris base and propagated in *E. coli* XL1-Blue in the presence of M13K07 helper phage; amplified phage were used for selection against the same target in the previous round. Phage sorting was stopped, generally at round 2 or 3, when 100-fold enrichment was obtained. Enrichment was calculated from the ratio of the phage titer eluted from the target-coated wells to the phage titer eluted from the BSA-coated wells. Individual clones from each library and selection target were then grown in a 96-well format in 400 µl of 2YT medium supplemented with carbenicillin and KO7 helper phage.

Phage ELISA assays (Sidhu, S. S., Weiss, G. A., and Wells, J. A. (2000) *J Mol Biol* 296, 487-495) were performed to detect phage-displayed variants of BCMA ECD capable of binding BAFF, APRIL or anti-tag antibody. Generally, the phage ELISA assays were carried out as described below.

Cultures of *E. coli* XL1-Blue harboring phagemids were grown for eight hours at 37° C. in 1 ml of 2YT, 50 mg/ml carbenicillin, 10 mg/ml tetracycline. The cultures were transferred to 30 ml of the same medium, supplemented with M13-KO7 helper phage (10^10 phage/ml) at the appropriate concentration, and grown overnight at 37° C. Phage were harvested from the culture supernatant by precipitation twice with 20% PEG/NaCl and resuspended in 1.0 ml of BSA blocking buffer (phosphate-buffered saline, 0.2% (w/v) BSA, 0.1% (v/v) Tween 20). Phage concentrations were determined spectrophotometrically (268=1.2×10 8M−1 cm−1).

Maxisorp immunoplates (96-well) were coated with capture target protein for two hours at room temperature (100 l at 5 g/ml in 50 mM carbonate buffer (pH 9.6)). The plates were then blocked for one hour with 0.2% BSA in phosphate-buffered saline (PBS) at room temperature and washed eight times with PBS, 0.05% Tween 20. Phage particles were serially diluted into BSA blocking buffer and 100 μl was transferred to coated wells. After one hour at room temperature, plates were washed eight times with PBS, 0.05% Tween 20, incubated with 100 μl of 1:3000 horseradish peroxidase/anti-M13 antibody conjugate in BSA blocking buffer for 30 minutes, and then washed eight times with PBS, 0.05% Tween 20 and twice with PBS. Plates were developed using an o-phenylenediamine dihydrochloride/$H_2O_2$ solution (100 μl), stopped with 2.5 M $H_2SO_4$ (50 μl), and absorbance measured at 492 nm.

All clones tested that were found to be positive in their respective ELISAs were then sequenced as described previously (Sidhu, S. S. (2001) *Biomol Eng* 18, 57-63). Sequence data without ambiguity in the BCMA ECD sequence were translated and aligned. For selection of binding to BAFF, 40 and 47 sequences were analyzed from libraries 1 and 2, respectively. For selection of binding to APRIL, 44 and 46 sequences were analyzed from libraries 1 and 2, respectively. For the display selection, binding to anti-tag antibody, a minimum of 40 sequences was analyzed for each library. To quantify the effect of each mutation on ligand binding, normalized frequency ratios (F) for each amino acid position was calculated from a ratio of ligand selection to display efficiency selection, as described previously (Skelton, N. J., et al., (2003) *J Biol Chem* 278, 7645-7654).

Figure 3:
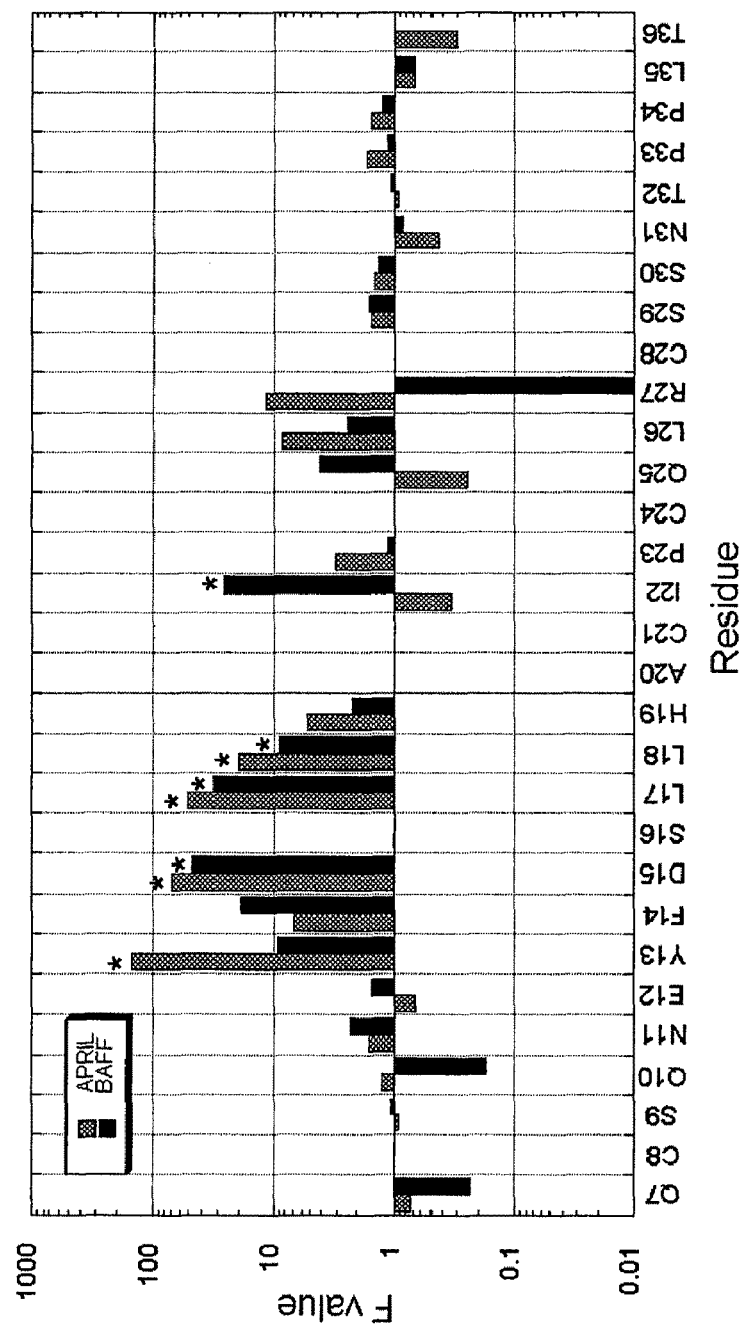
FIG. 3. Shotgun alanine-scan mutagenesis of BCMA for binding to BAFF or APRIL. The normalized frequency ratios (F) observed for each of the scanned positions in BCMA obtained from sequences of positive clones after two rounds of selection for binding to BAFF (solid) or APRIL (hatched). F values were calculated as described in experimental procedures for alanine substitutions. Those bars with an asterisk (*) above indicate values that represent a lower limit since Ala was not observed at these positions.

F values describe the effect of mutation on target binding, while accounting for differences in display efficiencies. This is generally accomplished by comparing the number of clones with the wild type residue at each position with the number of clones with each designed mutant at the same position (either alanine or homolog) and categorizing the substitutions as those that reduce (ratio>1), do not affect (ratio=approx. 1), or improve (ratio<1) binding to peptide. To control for variation in expression or display level for different library members, the libraries were also selected for binding to an immobilized antibody (e.g., 3C8:2F4) capable of recognizing an epitope tag that was displayed at the N terminus of all library members. A normalized frequency of occurrence (F) was derived by dividing the function selection of wt/mutant ratio by the display selection wt/mutant ratio. The normalized wild-type/alanine ratios (F) obtained at each position for both BAFF and APRIL selection are shown in FIG. 3.

Due to the relatively small pool of enriched sequences analyzed, only F values representing a greater than 10-fold effect are considered significant. The Tyr13 position in BCMA tolerated some alanine, as well as aspartate and serine, substitution for BAFF-binding but was absolutely conserved for APRIL-binding. The F values for Phe14 indicate a significant contribution to BAFF-binding but a more modest effect on affinity for APRIL. For both BAFF and APRIL binding, amino acids Asp15 and Leu17 are absolutely critical in that only wild-type residues were selected. The Asp15 and Leu17 form a part of a D×L motif present at the tip of a type I b-turn in BCMA (Kayagaki, N., et al., (2002) *Immunity* 17, 515-524; Liu, Y., et al., (2003) *Nature* 423, 49-56).

A conservative substitution of Leu 18 to Val was observed for both APRIL and BAFF selection, however alanine was not observed at this position. Ala substitution of Ile22 was not tolerated for binding to BAFF but was compatible with APRIL binding. The Gln25 to Ala replacement appeared to have opposite effects on APRIL and BAFF binding but the difference in F value was barely significant. In contrast, Ala substitution of Arg27 was strongly preferred for binding to BAFF and disfavored for APRIL binding. Other replacements in the C-terminal portion of BCMA had no effect on ligand binding.

Figure 4B:
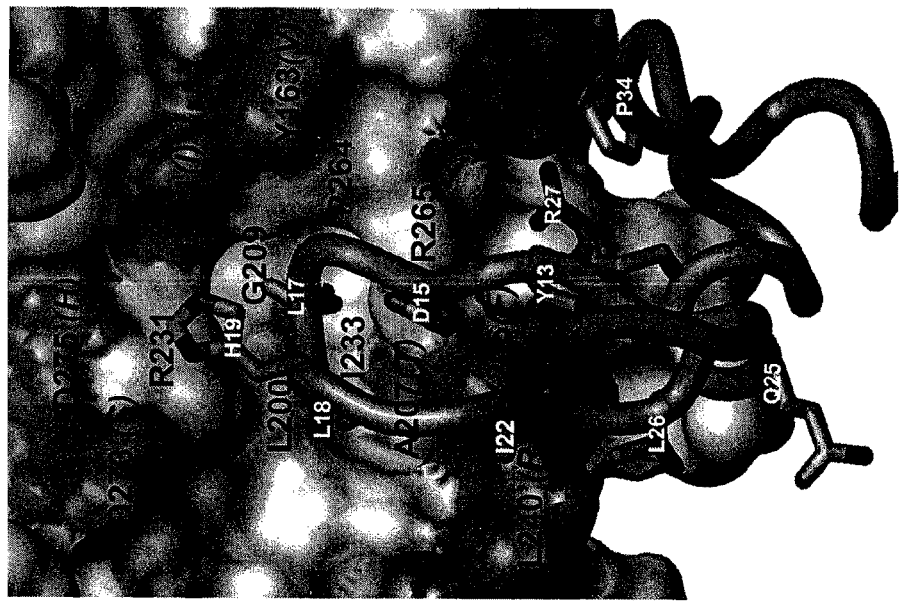
FIG. 4A-B. Functional and structural epitopes for ligand-binding by BCMA. A. Summary of BAFF- and APRIL-binding determinants mapped onto the structure of BCMA (PDB code 1OQD, (Liu, Y, et al. (2003) Nature 423:49-56). All side chains evaluated in the shotgun alanine-scan are shown. Side chains labeled F14, I22 and Q25 show >10-fold decrease on binding to BAFF when substituted by alanine; those labeled R27 and Y13 show >10-fold decrease on binding to APRIL when substituted by alanine; those labeled D15, L17 and L18 show >10-fold decrease on binding to both BAFF and APRIL when substituted by alanine. B. Close-up of the BAFF-BCMA contact region from the ligand-receptor co-crystal structure (PDB code 1OQD, (Liu, Y., et al., supra)); BAFF contact residues are labeled in black font while those for BCMA are labeled in white font. BCMA is shown as a ribbon; only side chains that contact BAFF are shown, with the addition of Gln25. BAFF is shown in a surface representation, with the portion of the surface that contacts BCMA labeled in large bold print; residues labeled I223, L200', G209, R231, P264 and R265 of BAFF are identical between BAFF and APRIL; residues labeled Y163(V), Y206(F), A207(T), L211(I), L240'(R), E266(A), D273'(S) and D275'(H) are residues that differ between BAFF and APRIL, with the APRIL residue type shown parenthetically using single amino acid code. The apostrophe indicates that the residue is contributed by an adjacent monomer of the trimer.
Figure 4A:
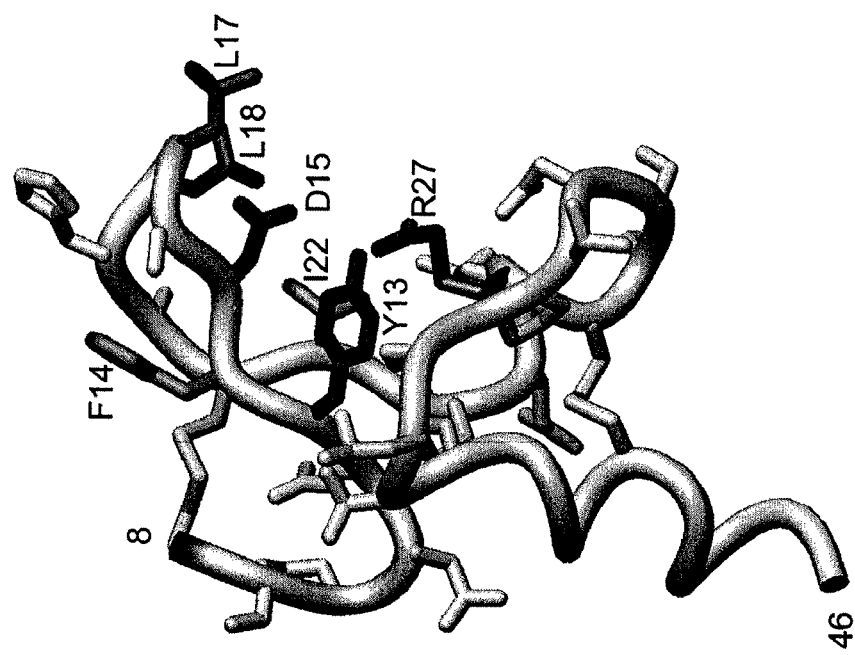

These results suggest that this portion of BCMA is bound in a cavity on APRIL that is similar to the pocket on BAFF for binding BCMA and BR3 (Liu, Y., et al. (2002) *Cell* 108, 383-394; Kim, H. M., et al. (2003) *Nat Struct Biol* 10, 342-348; Oren, D. A., et al. (2002) *Nat Struct Biol* 9, 288-29232-34). FIG. 4A shows the structure of residues 8 to 46 of BCMA.

In the structures determined for the BR3-BAFF or BCMA-BAFF (FIG. 4B) complexes, the leucine residue of the D×L motif (Leu28 in BR3, Leu 17 in BCMA) interacts with BAFF residues Ala207, Leu211, Ile233, and Pro264, with Gly209 forming the bottom of the pocket. The Asp residue of the D×L motif (Asp26 in BR3, Asp15 in BCMA) makes a salt bridge with BAFF residue Arg265 and the conformation of the Asp may be stabilized through a hydrogen bond with BAFF residue Tyr206. High-resolution structures for APRIL by itself or in complex with BCMA are not available; however, APRIL is expected to have a similar binding pocket for the leucine side chain since, as shown in FIG. 4B, the key residues are conserved (Gly209, Ile233, Pro264) or conservatively substituted (A207T, L211V). Arg265 is conserved in APRIL, thus allowing formation of a salt bridge with Asp15.

Example 4

Further Studies in BCMA-Ligand Binding Specificity

NNS library construction and sorting. Mutagenesis results for residues Ile22, Gln25, and Arg27 in Example 3 suggest these positions are likely candidates for providing ligand specificity since Ala substitution had opposite effects on BAFF and APRIL binding. Positions Leu18, Ile22, Gln25, and Arg27 were selected for further phage optimization studies by incorporation of NNS degenerate codons at these positions in a BCMA2-g3 phagemid followed by selection for ligand binding (NNS degenerate codon as defined by IUB code (Sidhu, S. S., et al. (2000) *Methods Enzymol* 328, 333-363). The library contained $1\times10^{10}$ phage/ml allowing complete representation of the library, theoretically $1\times10^6$ unique members.

Because each amino acid position selected for NNS codon introduction has the potential of all 20 amino acids from 31 triplet codons, the data was weighed according to codon degeneracy by calculating the ratio of percent occurrence to percent degeneracy of the amino acid at a given position as suggested previously (LaBean, T. H., and Kauffman, S. A. (1993) *Protein Sci* 2, 1249-1254). The normalized F' value corrects for display bias and calculated as the percent occurrence to percent degeneracy ratio for ligand selection divided by the percent occurrence to percent degeneracy ratio for display efficiency. Percent occurrence is calculated by dividing the number of times a particular amino acid appeared at a particular position by the total number of amino acids sequenced at that position followed by multiplying by 100, Percent degeneracy is calculated by dividing the degeneracy in code for a particular amino acid (see chart below) divided by the total degeneracy possible at that position followed by multiplying by 100 (e.g., if only A, G and I were selected, total degeneracy possible would be 5).

| degeneracy | a.a. |
|---|---|
| 2 | A |
| 1 | C |
| 1 | D |
| 1 | E |
| 2 | F |
| 2 | G |
| 1 | H |
| 1 | I |
| 1 | K |
| 3 | L |
| 1 | M |
| 1 | N |
| 2 | P |
| 1 | Q |
| 3 | R |
| 3 | S |
| 2 | T |
| 2 | V |
| 1 | W |
| 1 | Y |

This new phage library was subjected to three rounds of sorting against either BAFF or APRIL and compared to the display target antibody.

A large F' value for an amino acid at a given position indicates that the amino acid is a favorable substitution for binding to the target ligand. As shown in Table 6, the substitutions that result in the maximum difference in F' (Sidhu, S. S., et al., (2000) *Methods Enzymol* 328, 333-363, LaBean, T. H., and Kauffman, S. A. (1993) *Protein Sci* 2, 1249-1254) between APRIL binding and BAFF binding are I22K, Q25D, and R27Y. The I22K substitution produced a >12-fold preference for APRIL binding over BAFF binding; Q25D and R27Y resulted in >13-fold and 9.5-fold preference for BAFF binding relative to APRIL binding, respectively. The L18I substitution was a relatively conservative substitution.

TABLE 6

| a.a. | F' BAFF | | | | F' APRIL | | | |
|---|---|---|---|---|---|---|---|---|
| | L18 | I22 | Q25 | R27 | L18 | I22 | Q25 | R27 |
| A | 0 | 6 | 0 | 1 | 0 | 0 | 0 | 0 |
| C | 0 | 0 | 0 | 0 | 0 | 0 | 0 | 0 |
| D | 0 | 0 | 13 | 0 | 0 | 0 | 0 | 0 |
| E | 0 | 0 | 1 | 0 | 0 | 0 | 1 | 0 |
| F | 0 | 0 | 0 | 1 | 0 | 0 | 0 | 0 |
| G | 0 | 0 | 2 | 0 | 0 | 0 | 3 | 0 |
| H | 0 | 0 | 0 | 5 | 0 | 0 | 0 | 0 |
| I | 18 | 6 | 9 | 5 | 8 | 6 | 0 | 0 |
| K | 0 | 0 | 1 | 0 | 0 | 12 | 1 | 0 |
| L | 4 | 1 | 0 | 1 | 9 | 0 | 1 | 0 |
| M | 0 | 0 | 0 | 1 | 0 | 6 | 6 | 1 |
| N | 0 | 0 | 0 | 0 | 0 | 0 | 6 | 0 |
| P | 3 | 0 | 0 | 0 | 0 | 0 | 3 | 0 |
| Q | 0 | 0 | 9 | 0 | 0 | 0 | 12 | 0 |

TABLE 6-continued

| a.a. | F' BAFF | | | | F' APRIL | | | |
|---|---|---|---|---|---|---|---|---|
| | L18 | I22 | Q25 | R27 | L18 | I22 | Q25 | R27 |
| R | 0 | 1 | 2 | 0 | 0 | 0 | 4 | 53 |
| S | 0 | 0 | 1 | 4 | 0 | 1 | 4 | 0 |
| T | 6 | 0 | 2 | 1 | 0 | 1 | 0 | 0 |
| V | 5 | 7 | 1 | 1 | 2 | 6 | 0 | 1 |
| W | 0 | 0 | 0 | 5 | 0 | 0 | 0 | 0 |
| Y | 0 | 0 | 9 | 19 | 0 | 0 | 6 | 2 |

Table 6. Residue preferences at BCMA positions 18, 22, 25, 27 for binding to BAFF or APRIL. A library having complete randomization (NNS codons) at these 4 sites was prepared and sorted for binding to BAFF or APRIL. The normalized F' values for each of the scanned positions in BCMA obtained from sequences of positive clones after three rounds of selection for binding to BAFF or APRIL. Normalized frequency values (F') are calculated from the target/display ratio taking into consideration codon degeneracy as described in experimental procedures. In boldface are the F' values that are greater than 10-fold change in frequency. A zero value indicates a position were the amino acid was not observed in screened clones.

Example 5

Competitive Binding Assays with Mutant BCMA-Z Fusions

In order to confirm the effects on ligand binding indicated by the phage display results, point mutants were produced as BCMA-Z fusion proteins, purified, and assayed for BAFF and APRIL binding by competitive displacement ELISA (Table 7).

TABLE 7

| | IC$_{50}$ values | |
|---|---|---|
| BCMA-Z | BAFF (µM) | APRIL (nM) |
| wt | 8 ± 5 | 11 ± 3 |
| Y13A | 12 | 5100 |
| Y13S | 6 | 8400 |
| Y13F | 3 | 5700 |
| I22K | >100 | 38 |
| Q25D | 36 | 32 |
| R27Y | 4 | 400 |
| Q25D/R27Y | 0.7 | 350 |

Table 7. Competitive displacement assay of BCMA-Z mutants binding to APRIL or BAFF. IC$_{50}$ values shown are for BCMA-Z wt (mean±s.d of four data sets) or BCMA-Z point mutants competing with biotinylated BCMA-Z for binding to immobilized APRIL or BAFF or competition with biotinylated BR3 for binding to BAFF (not shown).

These data show that Tyr13 is critical for BCMA binding to APRIL since Ala, Ser, or Phe substitutions of this residue all increased the IC$_{50}$ by at least 400-fold (Table 7). The substitution of Tyr13 with Ala, Ser, or Phe, produced only small changes in affinity for BAFF. Consistent with the phage display results, the single amino acid substitution of I22K in BCMA-Z caused a greater than 10-fold reduction in affinity for BAFF but only about a 3-fold penalty for APRIL binding. Table 7 also shows that the single substitution of Q25D in BCMA-Z did not significantly improve binding to BAFF relative to APRIL, while the single amino acid substitution of R27Y reduced APRIL binding 40-fold, compared to wild-type. The double mutant Q25D/R27Y produced a receptor that could bind both APRIL and BAFF with nearly the same affinity. These substitutions gave non-additive contributions to binding since the effect measured for the double mutant was greater than the sum of effects measured for the single mutants. For example, the Q25D substitution resulted in decreased affinity for BAFF but when combined with R27Y it gave an increased affinity.

Surface plasmon resonance was used to independently measure the binding constants of the mutant BCMA-Z proteins for APRIL (Table 8).

TABLE 8

| BCMA-Z | $k_a$ ($\times 10^{-5}$ M$^{-1}$s$^{-1}$) | $k_d$ ($\times 10^3$ s$^{-1}$) | $K_D$ (nM) |
|---|---|---|---|
| wt | 8.5 | 4.7 | 5.5 |
| I22K | 11.0 | 6.9 | 6.3 |
| Q25D | 7.9 | 5.9 | 7.5 |
| R27Y | 0.1 | 25 | 6500 |

Table 8. BCMA-Z binding to immobilized APRIL by surface plasmon resonance. The rate constants and dissociation constants (KD) were calculated by nonlinear regression analysis using a 1:1 binding model.

Consistent with ELISA $IC_{50}$ measurements, BCMA-Z wild-type, I22K, and Q25D all bound APRIL in the low nM range. R27Y BCMA-Z binding to APRIL showed a 1000-fold reduction in affinity. The decreased affinity of this mutant results primarily from a decrease in the on-rate of binding, which leads to poor fitting to a 1:1 binding model and likely underestimates the actual $K_D$. The SPR data for BCMA-Z Q25D/R27Y binding to APRIL was not well described by a 1:1 binding model such that the rate and equilibrium constants could not be calculated.

Residues outside of the D×L motif confer specificity of BCMA for APRIL and BR3 for BAFF. The BAFF-BCMA crystal structure (Liu, Y., et al., (2003) Nature 423, 49-56) shows that the hydroxyl group of Tyr13 has the potential to form hydrogen bonds with Asp15 and Arg27 on BCMA, and/or Tyr206 on BAFF (FIG. 4). These results indicate that none of these potential hydrogen bonds are important for BAFF-binding. In contrast, the hydroxyl group is clearly essential for high-affinity APRIL binding. Interestingly, the residue corresponding to Tyr206 in APRIL is a phenylalanine, suggesting that the importance of Tyr13 likely results from an intra-molecular hydrogen bond within BCMA. Given the key role of Asp15 in the interface, the importance of Tyr13 to APRIL binding may be due to an indirect effect of influencing the position of Asp15; in BAFF, such a role could be accomplished by Tyr206 on the ligand.

Arg27 of BCMA is also important for specifying APRIL versus BAFF-binding. Again, mutation of this position has little effect on BAFF-binding but disrupts APRIL-binding significantly (Tables 3 and 4). In the BAFF-BCMA crystal structure, Arg27 forms a salt bridge with Glu266, yet the R27Y mutant indicates that this salt-bridge is not required for BAFF association. This conclusion is consistent with the observation of a high-affinity BAFF-BR3 interaction, since BR3 has a leucine (Leu38) in the position analogous to Arg27. Since APRIL has Glu266 replaced with Ala, it is unclear why Arg27 of BCMA is required for high-affinity binding to APRIL. Further understanding of this effect will require determination of the BCMA-APRIL complex structure. In addition to the contributions from Leu38 interactions, the specificity of BR3 for BAFF over APRIL could be explained by the substitution of a cysteine residue (Cys24 which makes a disulfide bond with Cys35) for the residue equivalent to Tyr13. Indeed, the C24Y mutation in BR3 increases affinity for APRIL (Liu, Y., et al. (2003) Nature 423, 49-56) and hydrophobic residues at position 38 in BR3 are important for BAFF-binding (Gordon, N. C., et al., (2003) Biochemistry 42, 5977-5983).

In addition to BCMA residues Tyr13 and Arg27, the results from phage display experiments suggest that Ile22 and Gln25 are important for determining ligand specificity. Ile22 makes a hydrophobic contact with BAFF and thus the I22K substitution results in a weaker affinity for BAFF. The contact residues for Ile22 on BAFF, Tyr206 and Leu240, are replaced with Phe and Arg in APRIL. Given the positive charge on APRIL residue Arg240, it is surprising that the I22K substitution has no effect on affinity for APRIL. The side chain of Gln25 is not in contact with BAFF and thus the Q25D single mutation has no significant effect on APRIL or BAFF binding. However, Q25D did increase affinity for BAFF when combined with R27Y such that a dual specificity BCMA variant was obtained. Given that Arg27 and Gln25 point in opposite directions, the origin of this non-additive effect is unclear.

Example 6

BCMA(I22K)-Fc Fusion

A BCMA(I22K)-Fc immunoadhesin having the sequence described in FIG. 6 and a BCMA(wt)-Fc were engineered by ligating nucleic acid sequences encoding residues A5 to G51 of BCMA (wt or I22K mutant) upstream of nucleic acid sequences encoding an Fc domain of IgG1. The fusion proteins were expressed in HEK293 cells and purified by affinity chromatography. Secreted Fc fusion proteins from HEK293 growth media were bound to Protein A Sepharose and washed with 10 column volumes of PBS. Bound Fc fusions were eluted from the resin with glycine pH 3.0 and then neutralized with 2M Tris base.

BCMA-Fc wt and I22K mutant constructs were tested for binding to either APRIL or BAFF in a competition ELISA assay. A 100 μl solution of carbonate buffer (pH 9.6) containing 2 μg/ml target ligand, either APRIL or BAFF, was coated on Nunc Maxisorp 96 well plates overnight at 4° C. The plate was washed with PBS and blocked for 1 hr with 200 μl of 0.2% BSA in PBS at room temperature. Three-fold serial dilutions of BCMA-Fc constructs were prepared in PBS/0.05% Tween-20 with 7 μM biotinylated BCMA-Z (when APRIL was the target) or 0.3 μM biotinylated "miniBR3", BR3 residues 17-42, (when BAFF was the target). MiniBR3 was prepared and biotinylated as described previously (Gordon, 2003). For BCMA-Z biotinylation, 20 μg of purified BCMA-Z was incubated with a 3-fold molar excess of biotin-sulphoNHS (Pierce) in PBS at 25° C. for 3 hrs and then quenched with a 10-fold molar excess of Tris-HCl, pH 7.5. After washing the NUNC plate coated with either APRIL or BAFF with PBS/0.05% Tween-20, 100 μl/well of each receptor dilution was transferred to the washed plate and incubated for 1 hr at room temperature. The plate was washed with PBS/Tween-20 and incubated with 100 μl/well of 0.1 U/ml Streptavidin-POD (Boehringer Mannheim) for 15 minutes at room temperature. After washing the plate with PBS/0.05% Tween-20 followed by a final wash in PBS, the plate was incubated for 5 min with 100 μl/well PBS substrate solution containing 0.8 mg/ml OPD (Sigma) and 0.01% $H_2O_2$. The reaction was quenched with 100 μl/well of 1M $H_3PO_4$ and the plate was read at 492 nm.

Figure 7:
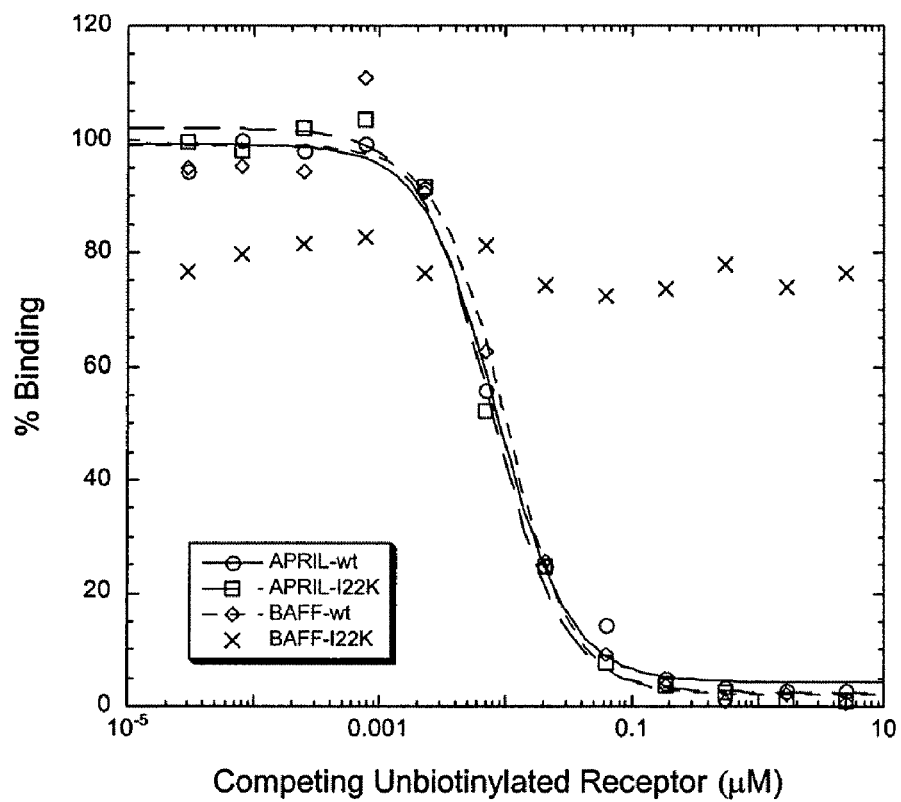
FIG. 7. Competitive displacement assay: BCMA-Fc binding to APRIL and BAFF and BCMA-I22K-Fc binding to APRIL and BAFF in the presence of increasing amounts of unbiotinylated BCMA-Fc or BCMA-I2K-Fc receptor, respectively.

FIG. 7 shows that the IC50 for wt BCMA-Fc binding to APRIL and BAFF, as well as BCMA-I22K-Fc binding to APRIL are in the 7-10 nM range. There was no apparent binding of BCMA-I22K-Fc to BAFF.

What is claimed:

1. An isolated polypeptide that binds APRIL comprising the following sequence:

C-S-Q-N-E-Y-F-D-S-L $X_{11}$-H-A-C-$X_{15}$-P-C-$X_{18}$-L-$X_{20}$-C-S-S-N-T-P-P-L-T-C-Q-R-Y-C (SEQ ID NO: 34) wherein $X_{11}$ is L, I, or V; wherein $X_{15}$ is I, A, or K; wherein $X_{18}$ is Q or D; and wherein $X_{20}$ is R or Y and wherein the sequence does not comprise the sequence

CSQNEYFDSLLHACIPCQLRCSSNTPPLTCQRYC. (SEQ ID NO: 35)

2. The isolated polypeptide according to claim 1, wherein if $X_{20}$ is Y, then $X_{18}$ is D.

3. The isolated polypeptide according to claim 1, wherein $X_{15}$ is K.

4. The isolated polypeptide according to claim 1, wherein $X_{18}$ is Q.

5. The isolated polypeptide according to claim 1, wherein $X_{20}$ is R.

6. The isolated polypeptide according to claim 1, wherein the polypeptide comprises an amino acid sequence that is 85% or more identical to a CRD sequence of a native BCMA SEQ ID NO: 35.

7. The isolated polypeptide according to claim 1, wherein the sequence is selected from the group consisting of:

CSQNEYFDSLLHACKPCQLRCSSNTPPLTCQRYC, (SEQ ID NO: 6)

CSQNEYFDSLLHACKPCDLRCSSNTPPLTCQRYC, (SEQ ID NO: 7)

CSQNEYFDSLLHACKPCDLYCSSNTPPLTCQRYC, and (SEQ ID NO: 8)

CSQNEYFDSLVHACKPCQLRCSSNTPPLTCQRYC. (SEQ ID NO: 9)

8. The isolated polypeptide according to claim 1, wherein the polypeptide further comprises the sequence NSVKGT linked carboxy-terminal to the polypeptide set forth in SEQ ID NO: 34.

9. The isolated polypeptide according to claim 1, wherein the polypeptide further comprises a sequence that is heterologous to a native BCMA polypeptide positioned at the N-terminus, C-terminus, or both the N-terminus and C-terminus of the polypeptide.

10. The isolated polypeptide according to claim 1, wherein the polypeptide further comprises the Fc domain of an IgG1 protein.

11. The isolated polypeptide according to claim 10, wherein the polypeptide comprises the amino acid sequence set forth in SEQ ID NO: 31.

12. The isolated polypeptide according to claim 1, wherein the polypeptide further comprises a leucine zipper.

13. The isolated polypeptide according to claim 1, wherein the polypeptide is attached to a non-proteinaceous polymer comprising polyethylene glycol.

14. The isolated polypeptide according to claim 1, wherein the polypeptide is an antibody.

15. The isolated polypeptide according to claim 14, wherein the antibody is selected from the group consisting of a F(ab) antibody, F(ab')2 antibody, and a scFv antibody.

16. The isolated polypeptide according to claim 1, wherein the polypeptide is attached to an agent selected from the group consisting of a growth inhibitory agent, a cytotoxic agent, a detection agent, an agent that improves the bioavailability of the polypeptide, and an agent that improves the half-life of the polypeptide.

17. The isolated polypeptide according to claim 16, wherein said cytotoxic agent is selected from the group consisting of a toxin, an antibiotic, and a radioactive isotope.

18. The isolated polypeptide according to claim 1, wherein $X_{11}$ is L, $X_{15}$ is K and $X_{18}$ is Q.

19. The isolated polypeptide according to claim 1, wherein said polypeptide binds to BCMA with decreased affinity as compared to a native BCMA polypeptide.

20. The isolated polypeptide according to claim 1, wherein said polypeptide binds to APRIL with increased affinity as compared to a native BCMA polypeptide.

21. A nucleic acid molecule encoding the polypeptide according to claim 1.

22. A vector comprising the nucleic acid molecule according to claim 21.

23. A host cell comprising the nucleic acid molecule according to claim 21 or a vector comprising the nucleic acid molecule.

24. A composition comprising the isolated polypeptide according to claim 1, optionally further comprising a pharmaceutically acceptable carrier.

25. A composition comprising the polypeptide according to claim 1, optionally further comprising a second therapeutic agent selected from the group consisting of an agent for treating an immune-related disease, a chemotherapeutic agent, and a cytotoxic agent.

26. A method for producing a polypeptide comprising the step of culturing a host cell comprising the vector according to claim 22 under conditions suitable for expressing the polypeptide from the vector.

* * * * *

```
                              SEQUENCE LISTING

<160> NUMBER OF SEQ ID NOS: 35

<210> SEQ ID NO 1
<211> LENGTH: 34
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Formula I
<220> FEATURE:
<221> NAME/KEY: MISC_FEATURE
<222> LOCATION: (2)..(5)
<223> OTHER INFORMATION: Xaa is any amino acid except cysteine
<220> FEATURE:
<221> NAME/KEY: MISC_FEATURE
<222> LOCATION: (7)..(7)
<223> OTHER INFORMATION: Xaa is any amino acid except cysteine
<220> FEATURE:
<221> NAME/KEY: MISC_FEATURE
<222> LOCATION: (9)..(9)
<223> OTHER INFORMATION: Xaa is any amino acid except cysteine
<220> FEATURE:
<221> NAME/KEY: MISC_FEATURE
<222> LOCATION: (11)..(11)
<223> OTHER INFORMATION: Xaa is any amino acid residue except Ala
      and cysteine
<220> FEATURE:
<221> NAME/KEY: MISC_FEATURE
<222> LOCATION: (12)..(13)
<223> OTHER INFORMATION: Xaa is any amino acid except cysteine
<220> FEATURE:
<221> NAME/KEY: MISC_FEATURE
<222> LOCATION: (16)..(16)
<223> OTHER INFORMATION: Xaa is any amino acid except cysteine
<220> FEATURE:
<221> NAME/KEY: MISC_FEATURE
<222> LOCATION: (18)..(20)
<223> OTHER INFORMATION: Xaa is any amino acid except cysteine
<220> FEATURE:
<221> NAME/KEY: MISC_FEATURE
<222> LOCATION: (22)..(29)
<223> OTHER INFORMATION: Xaa is any amino acid except cysteine
<220> FEATURE:
<221> NAME/KEY: MISC_FEATURE
<222> LOCATION: (31)..(33)
<223> OTHER INFORMATION: Xaa is any amino acid except cysteine

<400> SEQUENCE: 1

Cys Xaa Xaa Xaa Xaa Tyr Xaa Asp Xaa Leu Xaa Xaa Xaa Cys Lys Xaa
1               5                   10                  15

Cys Xaa Xaa Xaa Cys Xaa Xaa Xaa Xaa Xaa Xaa Xaa Xaa Cys Xaa Xaa
            20                  25                  30

Xaa Cys

<210> SEQ ID NO 2
<211> LENGTH: 40
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Formula I
<220> FEATURE:
<221> NAME/KEY: MISC_FEATURE
<222> LOCATION: (2)..(5)
<223> OTHER INFORMATION: Xaa is any amino acid except cysteine
<220> FEATURE:
<221> NAME/KEY: MISC_FEATURE
<222> LOCATION: (7)..(7)
```

```
<223> OTHER INFORMATION: Xaa is any amino acid except cysteine
<220> FEATURE:
<221> NAME/KEY: MISC_FEATURE
<222> LOCATION: (9)..(9)
<223> OTHER INFORMATION: Xaa is any amino acid except cysteine
<220> FEATURE:
<221> NAME/KEY: MISC_FEATURE
<222> LOCATION: (11)..(11)
<223> OTHER INFORMATION: Xaa is any amino acid residue except
      Ala and cysteine
<220> FEATURE:
<221> NAME/KEY: MISC_FEATURE
<222> LOCATION: (12)..(13)
<223> OTHER INFORMATION: Xaa is any amino acid except cysteine
<220> FEATURE:
<221> NAME/KEY: MISC_FEATURE
<222> LOCATION: (16)..(16)
<223> OTHER INFORMATION: Xaa is any amino acid except cysteine
<220> FEATURE:
<221> NAME/KEY: MISC_FEATURE
<222> LOCATION: (18)..(20)
<223> OTHER INFORMATION: Xaa is any amino acid except cysteine
<220> FEATURE:
<221> NAME/KEY: MISC_FEATURE
<222> LOCATION: (22)..(29)
<223> OTHER INFORMATION: Xaa is any amino acid except cysteine
<220> FEATURE:
<221> NAME/KEY: MISC_FEATURE
<222> LOCATION: (31)..(33)
<223> OTHER INFORMATION: Xaa is any amino acid except cysteine

<400> SEQUENCE: 2

Cys Xaa Xaa Xaa Xaa Tyr Xaa Asp Xaa Leu Xaa Xaa Xaa Cys Lys Xaa
1               5                   10                  15

Cys Xaa Xaa Xaa Cys Xaa Xaa Xaa Xaa Xaa Xaa Xaa Cys Xaa Xaa
            20                  25                  30

Xaa Cys Asn Ser Val Lys Gly Thr
        35                  40

<210> SEQ ID NO 3
<211> LENGTH: 34
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Formula I
<220> FEATURE:
<221> NAME/KEY: MISC_FEATURE
<222> LOCATION: (2)..(5)
<223> OTHER INFORMATION: Xaa is any amino acid except cysteine
<220> FEATURE:
<221> NAME/KEY: MISC_FEATURE
<222> LOCATION: (7)..(7)
<223> OTHER INFORMATION: Xaa is any amino acid except cysteine
<220> FEATURE:
<221> NAME/KEY: MISC_FEATURE
<222> LOCATION: (9)..(9)
<223> OTHER INFORMATION: Xaa is any amino acid except cysteine
<220> FEATURE:
<221> NAME/KEY: MISC_FEATURE
<222> LOCATION: (11)..(11)
<223> OTHER INFORMATION: Xaa is Leu, Val or Ile
<220> FEATURE:
<221> NAME/KEY: MISC_FEATURE
<222> LOCATION: (12)..(13)
<223> OTHER INFORMATION: Xaa is any amino acid except cysteine
<220> FEATURE:
<221> NAME/KEY: MISC_FEATURE
<222> LOCATION: (16)..(16)
<223> OTHER INFORMATION: Xaa is any amino acid except cysteine
<220> FEATURE:
<221> NAME/KEY: MISC_FEATURE
<222> LOCATION: (18)..(20)
<223> OTHER INFORMATION: Xaa is any amino acid except cysteine
<220> FEATURE:
```

```
<221> NAME/KEY: MISC_FEATURE
<222> LOCATION: (22)..(29)
<223> OTHER INFORMATION: Xaa is any amino acid except cysteine
<220> FEATURE:
<221> NAME/KEY: MISC_FEATURE
<222> LOCATION: (31)..(33)
<223> OTHER INFORMATION: Xaa is any amino acid except cysteine

<400> SEQUENCE: 3

Cys Xaa Xaa Xaa Xaa Tyr Xaa Asp Xaa Leu Xaa Xaa Xaa Cys Lys Xaa
1               5                   10                  15

Cys Xaa Xaa Xaa Cys Xaa Xaa Xaa Xaa Xaa Xaa Xaa Xaa Cys Xaa Xaa
            20                  25                  30

Xaa Cys

<210> SEQ ID NO 4
<211> LENGTH: 34
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Formula I
<220> FEATURE:
<221> NAME/KEY: MISC_FEATURE
<222> LOCATION: (2)..(5)
<223> OTHER INFORMATION: Xaa is any amino acid except cysteine
<220> FEATURE:
<221> NAME/KEY: MISC_FEATURE
<222> LOCATION: (7)..(7)
<223> OTHER INFORMATION: Xaa is any amino acid except cysteine
<220> FEATURE:
<221> NAME/KEY: MISC_FEATURE
<222> LOCATION: (9)..(9)
<223> OTHER INFORMATION: Xaa is any amino acid except cysteine
<220> FEATURE:
<221> NAME/KEY: MISC_FEATURE
<222> LOCATION: (11)..(11)
<223> OTHER INFORMATION: Xaa is any amino acid residue except
      Ala and cysteine
<220> FEATURE:
<221> NAME/KEY: MISC_FEATURE
<222> LOCATION: (12)..(13)
<223> OTHER INFORMATION: Xaa is any amino acid except cysteine
<220> FEATURE:
<221> NAME/KEY: MISC_FEATURE
<222> LOCATION: (16)..(16)
<223> OTHER INFORMATION: Xaa is any amino acid except cysteine
<220> FEATURE:
<221> NAME/KEY: MISC_FEATURE
<222> LOCATION: (18)..(18)
<223> OTHER INFORMATION: Xaa is selected from the group consisting
      of Gln, Asp and Ala
<220> FEATURE:
<221> NAME/KEY: MISC_FEATURE
<222> LOCATION: (19)..(20)
<223> OTHER INFORMATION: Xaa is any amino acid except cysteine
<220> FEATURE:
<221> NAME/KEY: MISC_FEATURE
<222> LOCATION: (22)..(29)
<223> OTHER INFORMATION: Xaa is any amino acid except cysteine
<220> FEATURE:
<221> NAME/KEY: MISC_FEATURE
<222> LOCATION: (31)..(33)
<223> OTHER INFORMATION: Xaa is any amino acid except cysteine

<400> SEQUENCE: 4

Cys Xaa Xaa Xaa Xaa Tyr Xaa Asp Xaa Leu Xaa Xaa Xaa Cys Lys Xaa
1               5                   10                  15

Cys Xaa Xaa Xaa Cys Xaa Xaa Xaa Xaa Xaa Xaa Xaa Xaa Cys Xaa Xaa
            20                  25                  30

Xaa Cys
```

<210> SEQ ID NO 5
<211> LENGTH: 34
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Formula I
<220> FEATURE:
<221> NAME/KEY: MISC_FEATURE
<222> LOCATION: (2)..(5)
<223> OTHER INFORMATION: Xaa is any amino acid except cysteine
<220> FEATURE:
<221> NAME/KEY: MISC_FEATURE
<222> LOCATION: (7)..(7)
<223> OTHER INFORMATION: Xaa is any amino acid except cysteine
<220> FEATURE:
<221> NAME/KEY: MISC_FEATURE
<222> LOCATION: (9)..(9)
<223> OTHER INFORMATION: Xaa is any amino acid except cysteine
<220> FEATURE:
<221> NAME/KEY: MISC_FEATURE
<222> LOCATION: (11)..(11)
<223> OTHER INFORMATION: Xaa is any amino acid residue except
    Ala and cysteine
<220> FEATURE:
<221> NAME/KEY: MISC_FEATURE
<222> LOCATION: (12)..(13)
<223> OTHER INFORMATION: Xaa is any amino acid except cysteine
<220> FEATURE:
<221> NAME/KEY: MISC_FEATURE
<222> LOCATION: (16)..(16)
<223> OTHER INFORMATION: Xaa is any amino acid except cysteine
<220> FEATURE:
<221> NAME/KEY: MISC_FEATURE
<222> LOCATION: (18)..(18)
<223> OTHER INFORMATION: Xaa is any amino acid except cysteine
<220> FEATURE:
<221> NAME/KEY: MISC_FEATURE
<222> LOCATION: (22)..(29)
<223> OTHER INFORMATION: Xaa is any amino acid except cysteine
<220> FEATURE:
<221> NAME/KEY: MISC_FEATURE
<222> LOCATION: (31)..(33)
<223> OTHER INFORMATION: Xaa is any amino acid except cysteine

<400> SEQUENCE: 5

Cys Xaa Xaa Xaa Xaa Tyr Xaa Asp Xaa Leu Xaa Xaa Xaa Cys Lys Xaa
1               5                   10                  15

Cys Xaa Asp Tyr Cys Xaa Xaa Xaa Xaa Xaa Xaa Xaa Cys Xaa Xaa
            20                  25                  30

Xaa Cys

<210> SEQ ID NO 6
<211> LENGTH: 34
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Formula I

<400> SEQUENCE: 6

Cys Ser Gln Asn Glu Tyr Phe Asp Ser Leu Leu His Ala Cys Lys Pro
1               5                   10                  15

Cys Gln Leu Arg Cys Ser Ser Asn Thr Pro Pro Leu Thr Cys Gln Arg
            20                  25                  30

Tyr Cys

<210> SEQ ID NO 7
<211> LENGTH: 34

```
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Formula I

<400> SEQUENCE: 7

Cys Ser Gln Asn Glu Tyr Phe Asp Ser Leu Leu His Ala Cys Lys Pro
1               5                   10                  15

Cys Asp Leu Arg Cys Ser Ser Asn Thr Pro Pro Leu Thr Cys Gln Arg
            20                  25                  30

Tyr Cys

<210> SEQ ID NO 8
<211> LENGTH: 34
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Formula I

<400> SEQUENCE: 8

Cys Ser Gln Asn Glu Tyr Phe Asp Ser Leu Leu His Ala Cys Lys Pro
1               5                   10                  15

Cys Asp Leu Tyr Cys Ser Ser Asn Thr Pro Pro Leu Thr Cys Gln Arg
            20                  25                  30

Tyr Cys

<210> SEQ ID NO 9
<211> LENGTH: 34
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Formula I

<400> SEQUENCE: 9

Cys Ser Gln Asn Glu Tyr Phe Asp Ser Leu Val His Ala Cys Lys Pro
1               5                   10                  15

Cys Gln Leu Arg Cys Ser Ser Asn Thr Pro Pro Leu Thr Cys Gln Arg
            20                  25                  30

Tyr Cys

<210> SEQ ID NO 10
<211> LENGTH: 34
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Formula II
<220> FEATURE:
<221> NAME/KEY: MISC_FEATURE
<222> LOCATION: (2)..(5)
<223> OTHER INFORMATION: Xaa is any amino acid except cysteine; and
      provided that the Formula II does not comprise the sequence
      CSQNEYFDSLLHACIPCQLRCSSNTPPLTCQRYC
<220> FEATURE:
<221> NAME/KEY: MISC_FEATURE
<222> LOCATION: (6)..(6)
<223> OTHER INFORMATION: Xaa is selected from the group consisting
      of Tyr, Ala, Asp, Ser and Phe
<220> FEATURE:
<221> NAME/KEY: MISC_FEATURE
<222> LOCATION: (7)..(7)
```

<223> OTHER INFORMATION: Xaa is any amino acid except cysteine; and
      provided that the Formula II does not com

```
<222> LOCATION: (2)..(5)
<223> OTHER INFORMATION: Xaa is any amino acid except cysteine; and
      provided that the Formula II does not comprise the sequence
      CSQNEYFDSLLHACIPCQLR CSSNTPPLTCQRYC
<220> FEATURE:
<221> NAME/KEY: MISC_FEATURE
<222> LOCATION: (6)..(6)
<223> OTHER INFORMATION: Xaa is selected from the group consisting
      of Tyr, Ala, Asp, Ser and Phe
<220> FEATURE:
<221> NAME/KEY: MISC_FEATURE
<222> LOCATION: (7)..(7)
<223> OTHER INFORMATION: Xaa is any amino acid except cysteine; and
      provided that the Formula II does not comprise the sequence
      CSQNEYFDSLLHACIPCQLRCSSNTPPLTCQRYC
<220> FEATURE:
<221> NAME/KEY: MISC_FEATURE
<222> LOCATION: (9)..(9)
<223> OTHER INFORMATION: Xaa is any amino acid except cysteine; and
      provided that the Formula II does not comprise the sequence
      CSQNEYFDSLLHACIPCQLRCSSNTPPLTCQRYC
<220> FEATURE:
<221> NAME/KEY: MISC_FEATURE
<222> LOCATION: (11)..(11)
<223> OTHER INFORMATION: Xaa is Leu, Val or Ile
<220> FEATURE:
<221> NAME/KEY: MISC_FEATURE
<222> LOCATION: (12)..(13)
<223> OTHER INFORMATION: Xaa is any amino acid except cysteine; and
      provided that the Formula II does not comprise the sequence
      CSQNEYFDSLLHACIPCQLRCSSNTPPLTCQRYC
<220> FEATURE:
<221> NAME/KEY: MISC_FEATURE
<222> LOCATION: (15)..(15)
<223> OTHER INFORMATION: Xaa is any amino acid residue except Ala
      or Lys
<220> FEATURE:
<221> NAME/KEY: MISC_FEATURE
<222> LOCATION: (16)..(16)
<223> OTHER INFORMATION: Xaa is any amino acid except cysteine; and
      provided that the Formula II does not comprise the sequence
      CSQNEYFDSLLHACIPCQLRCSSNTPPLTCQRYC
<220> FEATURE:
<221> NAME/KEY: MISC_FEATURE
<222> LOCATION: (18)..(18)
<223> OTHER INFORMATION: Xaa is selected from the group consisting of
      Gln, Asp and Ala
<220> FEATURE:
<221> NAME/KEY: MISC_FEATURE
<222> LOCATION: (19)..(19)
<223> OTHER INFORMATION: Xaa is any amino acid except cysteine; and
      provided that the Formula II does not comprise the sequence
      CSQNEYFDSLLHACIPCQLRCSSNTPPLTCQRYC
<220> FEATURE:
<221> NAME/KEY: MISC_FEATURE
<222> LOCATION: (20)..(20)
<223> OTHER INFORMATION: Xaa is selected from the group consisting
      of Tyr and Ala
<220> FEATURE:
<221> NAME/KEY: MISC_FEATURE
<222> LOCATION: (22)..(29)
<223> OTHER INFORMATION: Xaa is any amino acid except cysteine; and
      provided that the Formula II does not comprise the sequence
      CSQNEYFDSLLHACIPCQLR
      CSSNTPPLTCQRYC
<220> FEATURE:
<221> NAME/KEY: MISC_FEATURE
<222> LOCATION: (31)..(33)
<223> OTHER INFORMATION: Xaa is any amino acid except cysteine; and
      provided that the Formula II does not comprise the sequence
      CSQNEYFDSLLHACIPCQLRCSSNTPPLTCQRYC

<400> SEQUENCE: 11

Cys Xaa Xaa Xaa Xaa Xaa Xaa Asp Xaa Leu Xaa Xaa Xaa Cys Xaa Xaa
1               5                   10                  15

Cys Xaa Xaa Xaa Cys Xaa Xaa Xaa Xaa Xaa Xaa Xaa Xaa Cys Xaa Xaa
            20                  25                  30
```

Xaa Cys

```
<210> SEQ ID NO 12
<211> LENGTH: 34
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Formula II
<220> FEATURE:
<221> NAME/KEY: MISC_FEATURE
<222> LOCATION: (2)..(5)
<223> OTHER INFORMATION: Xaa is any amino acid except cysteine; and
      provided that the Formula II does not comprise the sequence
      CSQNEYFDSLLHACIPCQLRCSSNTPPLTCQRYC
<220> FEATURE:
<221> NAME/KEY: MISC_FEATURE
<222> LOCATION: (6)..(6)
<223> OTHER INFORMATION: Xaa is selected from the group consisting of
      Tyr, Ala, Asp, Ser and Phe
<220> FEATURE:
<221> NAME/KEY: MISC_FEATURE
<222> LOCATION: (7)..(7)
<223> OTHER INFORMATION: Xaa is any amino acid except cysteine; and
      provided that the Formula II does not comprise the sequence
      CSQNEYFDSLLHACIPCQLRCSSNTPPLTCQRYC
<220> FEATURE:
<221> NAME/KEY: MISC_FEATURE
<222> LOCATION: (9)..(9)
<223> OTHER INFORMATION: Xaa is any amino acid except cysteine; and
      provided that the Formula II does not comprise the sequence
      CSQNEYFDSLLHACIPCQLRCSSNTPPLTCQRYC
<220> FEATURE:
<221> NAME/KEY: MISC_FEATURE
<222> LOCATION: (11)..(11)
<223> OTHER INFORMATION: Xaa is any amino acid residue except Ala
<220> FEATURE:
<221> NAME/KEY: MISC_FEATURE
<222> LOCATION: (12)..(13)
<223> OTHER INFORMATION: Xaa is any amino acid except cysteine; and
      provided that the Formula II does not comprise the sequence
      CSQNEYFDSLLHACIPCQLRCSSNTPPLTCQRYC
<220> FEATURE:
<221> NAME/KEY: MISC_FEATURE
<222> LOCATION: (15)..(15)
<223> OTHER INFORMATION: Xaa is Ile, Val or Ala
<220> FEATURE:
<221> NAME/KEY: MISC_FEATURE
<222> LOCATION: (16)..(16)
<223> OTHER INFORMATION: Xaa is any amino acid except cysteine; and
      provided that the Formula II does not comprise the sequence
      CSQNEYFDSLLHACIPCQLRCSSNTPPLTCQRYC
<220> FEATURE:
<221> NAME/KEY: MISC_FEATURE
<222> LOCATION: (18)..(18)
<223> OTHER INFORMATION: Xaa is selected from the group consisting of
      Gln, Asp and Ala
<220> FEATURE:
<221> NAME/KEY: MISC_FEATURE
<222> LOCATION: (19)..(19)
<223> OTHER INFORMATION: Xaa is any amino acid except cysteine;
      and provided that the Formula II does not comprise the sequence
      CSQNEYFDSLLHACIPCQLRCSSNTPPLTCQRYC
<220> FEATURE:
<221> NAME/KEY: MISC_FEATURE
<222> LOCATION: (20)..(20)
<223> OTHER INFORMATION: Xaa is selected from the group consisting
      of Tyr and Ala
<220> FEATURE:
<221> NAME/KEY: MISC_FEATURE
<222> LOCATION: (22)..(29)
<223> OTHER INFORMATION: Xaa is any amino acid except cysteine; and
      provided that the Formula II does not comprise the sequence
      CSQNEYFDSLLHACIPCQLRCSSNTPPLTCQRYC
<220> FEATURE:
<221> NAME/KEY: MISC_FEATURE
<222> LOCATION: (31)..(33)
<223> OTHER INFORMATION: Xaa is any amino acid except cysteine;
``` and provided that the Formula II does not comprise the sequence
CSQNEYFDSLLHACIPCQLRCSSNTPPLTCQRYC

<400> SEQUENCE: 12

Cys Xaa Xaa Xaa Xaa Xaa Asp Xaa Leu Xaa Xaa Xaa Cys Xaa Xaa
1               5                   10                  15

Cys Xaa Xaa Xaa Cys Xaa Xaa Xaa Xaa Xaa Xaa Xaa Cys Xaa Xaa
            20                  25                  30

Xaa Cys

<210> SEQ ID NO 13
<211> LENGTH: 34
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Formula II

<400> SEQUENCE: 13

Cys Ser Gln Asn Glu Ala Phe Asp Ser Leu Leu His Ala Cys Ile Pro
1               5                   10                  15

Cys Gln Leu Arg Cys Ser Ser Asn Thr Pro Pro Leu Thr Cys Gln Arg
            20                  25                  30

Tyr Cys

<210> SEQ ID NO 14
<211> LENGTH: 34
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Formula II

<400> SEQUENCE: 14

Cys Ser Gln Asn Glu Ser Phe Asp Ser Leu Leu His Ala Cys Ile Pro
1               5                   10                  15

Cys Gln Leu Arg Cys Ser Ser Asn Thr Pro Pro Leu Thr Cys Gln Arg
            20                  25                  30

Tyr Cys

<210> SEQ ID NO 15
<211> LENGTH: 34
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Formula II

<400> SEQUENCE: 15

Cys Ser Gln Asn Glu Phe Phe Asp Ser Leu Leu His Ala Cys Ile Pro
1               5                   10                  15

Cys Gln Leu Arg Cys Ser Ser Asn Thr Pro Pro Leu Thr Cys Gln Arg
            20                  25                  30

Tyr Cys

<210> SEQ ID NO 16
<211> LENGTH: 34
<212> TYPE: PRT
<213> ORGANISM: Artificial Sequence
<220> FEATURE:
<223> OTHER INFORMATION: Synthetic Construct

```
<220> FEATURE:
<223> OTHER INFORMATION: Formula II

<400> SEQUENCE: 16

Cys Ser Gln Asn Glu Tyr Phe Asp Ser Leu Leu His Ala Cys Ile Pro
1               5                   10                  15

Cys Asp Leu Arg Cys Ser Ser Asn Thr Pro Pro Leu Thr Cys Gln Arg
            20                  25                  30

Tyr Cys

<210> SEQ ID NO 17
<211> LENGTH: 34
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Formula II

<400> SEQUENCE: 17

Cys Ser Gln Asn Glu Tyr Phe Asp Ser Leu Leu His Ala Cys Ile Pro
1               5                   10                  15

Cys Gln Leu Tyr Cys Ser Ser Asn Thr Pro Pro Leu Thr Cys Gln Arg
            20                  25                  30

Tyr Cys

<210> SEQ ID NO 18
<211> LENGTH: 34
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Formula II

<400> SEQUENCE: 18

Cys Ser Gln Asn Glu Tyr Phe Asp Ser Leu Leu His Ala Cys Ile Pro
1               5                   10                  15

Cys Asp Leu Tyr Cys Ser Ser Asn Thr Pro Pro Leu Thr Cys Gln Arg
            20                  25                  30

Tyr Cys

<210> SEQ ID NO 19
<211> LENGTH: 40
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Formula II
<220> FEATURE:
<221> NAME/KEY: MISC_FEATURE
<222> LOCATION: (2)..(5)
<223> OTHER INFORMATION: Xaa is any amino acid except cysteine;
      and provided that the Formula II does not comprise the sequence
      CSQNEYFDSLLHACIPCQLRCSSNTPPLTCQRYC
<220> FEATURE:
<221> NAME/KEY: MISC_FEATURE
<222> LOCATION: (6)..(6)
<223> OTHER INFORMATION: Xaa is selected from the group consisting of
      Tyr, Ala, Asp, Ser and Phe
<220> FEATURE:
<221> NAME/KEY: MISC_FEATURE
<222> LOCATION: (7)..(7)
<223> OTHER INFORMATION: Xaa is any amino acid except cysteine; and
      provided that the Formula II does not comprise the sequence
      CSQNEYFDSLLHACIPCQLRCSSNTPPLTCQRYC
<220> FEATURE:
```

```
<221> NAME/KEY: MISC_FEATURE
<222> LOCATION: (9)..(9)
<223> OTHER INFORMATION: Xaa is any amino acid except cysteine; and
      provided that the Formula II does not comprise the sequence
      CSQNEYFDSLLHACIPCQLRCSSNTPPLTCQRYC
<220> FEATURE:
<221> NAME/KEY: MISC_FEATURE
<222> LOCATION: (11)..(11)
<223> OTHER INFORMATION: Xaa is any amino acid residue except Ala
<220> FEATURE:
<221> NAME/KEY: MISC_FEATURE
<222> LOCATION: (12)..(13)
<223> OTHER INFORMATION: Xaa is any amino acid except cysteine; and
      provided that the Formula II does not comprise the sequence
      CSQNEYFDSLLHACIPCQLRCSSNTPPLTCQRYC
<220> FEATURE:
<221> NAME/KEY: MISC_FEATURE
<222> LOCATION: (15)..(15)
<223> OTHER INFORMATION: Xaa is any amino acid residue except Ala
      or Lys
<220> FEATURE:
<221> NAME/KEY: MISC_FEATURE
<222> LOCATION: (16)..(16)
<223> OTHER INFORMATION: Xaa is any amino acid except cysteine; and
      provided that the Formula II does not comprise the sequence
      CSQNEYFDSLLHACIPCQLRCSSNTPPLTCQRYC
<220> FEATURE:
<221> NAME/KEY: MISC_FEATURE
<222> LOCATION: (18)..(18)
<223> OTHER INFORMATION: Xaa is selected from the group consisting of
      Gln, Asp and Ala
<220> FEATURE:
<221> NAME/KEY: MISC_FEATURE
<222> LOCATION: (19)..(19)
<223> OTHER INFORMATION: Xaa is any amino acid except cysteine; and
      provided that the Formula II does not comprise the sequence
      CSQNEYFDSLLHACIPCQLRCSSNTPPLTCQRYC
<220> FEATURE:
<221> NAME/KEY: MISC_FEATURE
<222> LOCATION: (20)..(20)
<223> OTHER INFORMATION: Xaa is selected from the group consisting
      of Tyr and Ala
<220> FEATURE:
<221> NAME/KEY: MISC_FEATURE
<222> LOCATION: (22)..(29)
<223> OTHER INFORMATION: Xaa is any amino acid except cysteine; and
      provided that the Formula II does not comprise the sequence
      CSQNEYFDSLLHACIPCQLRCSSNTPPLTCQRYC
<220> FEATURE:
<221> NAME/KEY: MISC_FEATURE
<222> LOCATION: (31)..(33)
<223> OTHER INFORMATION: Xaa is any amino acid except cysteine; and
      provided that the Formula II does not comprise the sequence
      CSQNEYFDSLLHACIPCQLRCSSNTPPLTCQRYC

<400> SEQUENCE: 19

Cys Xaa Xaa Xaa Xaa Xaa Xaa Asp Xaa Leu Xaa Xaa Xaa Cys Xaa Xaa
1               5                   10                  15

Cys Xaa Xaa Xaa Cys Xaa Xaa Xaa Xaa Xaa Xaa Xaa Xaa Cys Xaa Xaa
            20                  25                  30

Xaa Cys Asn Ser Val Lys Gly Thr
        35                  40

<210> SEQ ID NO 20
<211> LENGTH: 184
<212> TYPE: PRT
<213> ORGANISM: Homo sapiens

<400> SEQUENCE: 20

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30
```

```
Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
 50                  55                  60

Ile Ile Ser Leu Ala Val Phe Val Leu Met Phe Leu Leu Arg Lys Ile
 65                  70                  75                  80

Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
                100                 105                 110

Ile Ile Leu Pro Arg Gly Leu Glu Tyr Thr Val Glu Glu Cys Thr Cys
                115                 120                 125

Glu Asp Cys Ile Lys Ser Lys Pro Lys Val Asp Ser Asp His Cys Phe
130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
                180
```

<210> SEQ ID NO 21
<211> LENGTH: 52
<212> TYPE: PRT
<213> ORGANISM: Artificial Sequence
<220> FEATURE:
<223> OTHER INFORMATION: Synthetic Construct
<220> FEATURE:
<223> OTHER INFORMATION: BMCA ECD (1-52)

<400> SEQUENCE: 21

```
Met Leu Gln Met Ala Gly Gln Cys Ser Gln Asn Glu Tyr Phe Asp Ser
 1               5                  10                  15

Leu Leu His Ala Cys Ile Pro Cys Gln Leu Arg Cys Ser Ser Asn Thr
                20                  25                  30

Pro Pro Leu Thr Cys Gln Arg Tyr Cys Asn Ala Ser Val Thr Asn Ser
        35                  40                  45

Val Lys Gly Thr
 50
```

<210> SEQ ID NO 22
<211> LENGTH: 38
<212> TYPE: PRT
<213> ORGANISM: Artificial Sequence
<220> FEATURE:
<223> OTHER INFORMATION: Synthetic Construct
<220> FEATURE:
<223> OTHER INFORMATION: BMCA CRD (8-41)

<400> SEQUENCE: 22

```
Ser Gln Asn Glu Tyr Phe Asp Ser Leu Leu His Ala Cys Ile Pro Cys
 1               5                  10                  15

Gln Leu Arg Cys Ser Ser Asn Thr Pro Pro Leu Thr Cys Gln Arg Tyr
                20                  25                  30

Cys Asn Ala Ser Val Thr
                35
```

<210> SEQ ID NO 23
<211> LENGTH: 285
<212> TYPE: PRT
<213> ORGANISM: Homo sapiens

<400> SEQUENCE: 23

Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys Leu Leu
        35                  40                  45

Ala Ala Thr Leu Leu Ala Leu Leu Ser Cys Cys Leu Thr Val Val
    50                  55                  60

Ser Phe Tyr Gln Val Ala Ala Leu Gln Gly Asp Leu Ala Ser Leu Arg
65                  70                  75                  80

Ala Glu Leu Gln Gly His His Ala Glu Lys Leu Pro Ala Gly Ala Gly
                85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Gly Asn Ser Ser Gln Asn
        115                 120                 125

Ser Arg Asn Lys Arg Ala Val Gln Gly Pro Glu Thr Val Thr Gln
130                 135                 140

Asp Cys Leu Gln Leu Ile Ala Asp Ser Glu Thr Pro Thr Ile Gln Lys
145                 150                 155                 160

Gly Ser Tyr Thr Phe Val Pro Trp Leu Leu Ser Phe Lys Arg Gly Ser
                165                 170                 175

Ala Leu Glu Glu Lys Glu Asn Lys Ile Leu Val Lys Glu Thr Gly Tyr
            180                 185                 190

Phe Phe Ile Tyr Gly Gln Val Leu Tyr Thr Asp Lys Thr Tyr Ala Met
        195                 200                 205

Gly His Leu Ile Gln Arg Lys Lys Val His Val Phe Gly Asp Glu Leu
    210                 215                 220

Ser Leu Val Thr Leu Phe Arg Cys Ile Gln Asn Met Pro Glu Thr Leu
225                 230                 235                 240

Pro Asn Asn Ser Cys Tyr Ser Ala Gly Ile Ala Lys Leu Glu Glu Gly
                245                 250                 255

Asp Glu Leu Gln Leu Ala Ile Pro Arg Glu Asn Ala Gln Ile Ser Leu
            260                 265                 270

Asp Gly Asp Val Thr Phe Phe Gly Ala Leu Lys Leu Leu
        275                 280                 285

<210> SEQ ID NO 24
<211> LENGTH: 309
<212> TYPE: PRT
<213> ORGANISM: Mus musculus

<400> SEQUENCE: 24

Met Asp Glu Ser Ala Lys Thr Leu Pro Pro Cys Leu Cys Phe Cys
1               5                   10                  15

Ser Glu Lys Gly Glu Asp Met Lys Val Gly Tyr Asp Pro Ile Thr Pro
            20                  25                  30

Gln Lys Glu Glu Gly Ala Trp Phe Gly Ile Cys Arg Asp Gly Arg Leu
        35                  40                  45

Leu Ala Ala Thr Leu Leu Leu Ala Leu Leu Ser Ser Phe Thr Ala
    50                  55                  60

Met Ser Leu Tyr Gln Leu Ala Ala Leu Gln Ala Asp Leu Met Asn Leu
65                  70                  75                  80

```
Arg Met Glu Leu Gln Ser Tyr Arg Gly Ser Ala Thr Pro Ala Ala Ala
            85                  90                  95

Gly Ala Pro Glu Leu Thr Ala Gly Val Lys Leu Leu Thr Pro Ala Ala
           100                 105                 110

Pro Arg Pro His Asn Ser Ser Arg Gly His Arg Asn Arg Arg Ala Phe
           115                 120                 125

Gln Gly Pro Glu Glu Thr Glu Gln Asp Val Asp Leu Ser Ala Pro Pro
       130                 135                 140

Ala Pro Cys Leu Pro Gly Cys Arg His Ser Gln His Asp Asp Asn Gly
145                 150                 155                 160

Met Asn Leu Arg Asn Ile Ile Gln Asp Cys Leu Gln Leu Ile Ala Asp
               165                 170                 175

Ser Asp Thr Pro Thr Ile Arg Lys Gly Thr Tyr Thr Phe Val Pro Trp
           180                 185                 190

Leu Leu Ser Phe Lys Arg Gly Asn Ala Leu Glu Glu Lys Glu Asn Lys
       195                 200                 205

Ile Val Val Arg Gln Thr Gly Tyr Phe Phe Ile Tyr Ser Gln Val Leu
210                 215                 220

Tyr Thr Asp Pro Ile Phe Ala Met Gly His Val Ile Gln Arg Lys Lys
225                 230                 235                 240

Val His Val Phe Gly Asp Glu Leu Ser Leu Val Thr Leu Phe Arg Cys
               245                 250                 255

Ile Gln Asn Met Pro Lys Thr Leu Pro Asn Asn Ser Cys Tyr Ser Ala
           260                 265                 270

Gly Ile Ala Arg Leu Glu Glu Gly Asp Glu Ile Gln Leu Ala Ile Pro
       275                 280                 285

Arg Glu Asn Ala Gln Ile Ser Arg Asn Gly Asp Asp Thr Phe Phe Gly
290                 295                 300

Ala Leu Lys Leu Leu
305

<210> SEQ ID NO 25
<211> LENGTH: 250
<212> TYPE: PRT
<213> ORGANISM: Homo sapiens

<400> SEQUENCE: 25

Met Pro Ala Ser Ser Pro Phe Leu Leu Ala Pro Lys Gly Pro Pro Gly
1               5                   10                  15

Asn Met Gly Gly Pro Val Arg Glu Pro Ala Leu Ser Val Ala Leu Trp
            20                  25                  30

Leu Ser Trp Gly Ala Ala Leu Gly Ala Val Ala Cys Ala Met Ala Leu
        35                  40                  45

Leu Thr Gln Gln Thr Glu Leu Gln Ser Leu Arg Arg Glu Val Ser Arg
    50                  55                  60

Leu Gln Gly Thr Gly Gly Pro Ser Gln Asn Gly Glu Gly Tyr Pro Trp
65                  70                  75                  80

Gln Ser Leu Pro Glu Gln Ser Ser Asp Ala Leu Glu Ala Trp Glu Asn
                85                  90                  95

Gly Glu Arg Ser Arg Lys Arg Arg Ala Val Leu Thr Gln Lys Gln Lys
            100                 105                 110

Lys Gln His Ser Val Leu His Leu Val Pro Ile Asn Ala Thr Ser Lys
        115                 120                 125

Asp Asp Ser Asp Val Thr Glu Val Met Trp Gln Pro Ala Leu Arg Arg
    130                 135                 140
```

Gly Arg Gly Leu Gln Ala Gln Gly Tyr Gly Val Arg Ile Gln Asp Ala
145                 150                 155                 160

Gly Val Tyr Leu Leu Tyr Ser Gln Val Leu Phe Gln Asp Val Thr Phe
                165                 170                 175

Thr Met Gly Gln Val Val Ser Arg Glu Gly Gln Gly Arg Gln Glu Thr
            180                 185                 190

Leu Phe Arg Cys Ile Arg Ser Met Pro Ser His Pro Asp Arg Ala Tyr
        195                 200                 205

Asn Ser Cys Tyr Ser Ala Gly Val Phe His Leu His Gln Gly Asp Ile
    210                 215                 220

Leu Ser Val Ile Ile Pro Arg Ala Arg Ala Lys Leu Asn Leu Ser Pro
225                 230                 235                 240

His Gly Thr Phe Leu Gly Phe Val Lys Leu
                245                 250

<210> SEQ ID NO 26
<211> LENGTH: 240
<212> TYPE: PRT
<213> ORGANISM: Mus musculus

<400> SEQUENCE: 26

Met Pro Ala Ser Ser Pro Gly His Met Gly Gly Ser Val Arg Glu Pro
1               5                   10                  15

Ala Leu Ser Val Ala Leu Trp Leu Ser Trp Gly Ala Val Leu Gly Ala
            20                  25                  30

Val Thr Cys Ala Val Ala Leu Leu Ile Gln Gln Thr Glu Leu Gln Ser
        35                  40                  45

Leu Arg Arg Glu Val Ser Arg Leu Gln Arg Ser Gly Gly Pro Ser Gln
    50                  55                  60

Lys Gln Gly Glu Arg Pro Trp Gln Ser Leu Trp Gln Gln Ser Pro Asp
65                  70                  75                  80

Val Leu Glu Ala Trp Lys Asp Gly Ala Lys Ser Arg Arg Arg Arg Ala
                85                  90                  95

Val Leu Thr Gln Lys His Lys Lys Lys His Ser Val Leu His Leu Val
            100                 105                 110

Pro Val Asn Ile Thr Ser Lys Asp Ser Asp Val Thr Glu Val Met Trp
        115                 120                 125

Gln Pro Val Leu Arg Arg Gly Arg Gly Leu Glu Ala Gln Gly Asp Ile
    130                 135                 140

Val Arg Val Trp Asp Thr Gly Ile Tyr Leu Leu Tyr Ser Gln Val Leu
145                 150                 155                 160

Phe His Asp Val Thr Phe Thr Met Gly Gln Val Val Ser Arg Glu Gly
                165                 170                 175

Gln Gly Arg Arg Glu Thr Leu Phe Arg Cys Ile Arg Ser Met Pro Ser
            180                 185                 190

Asp Pro Asp Arg Ala Tyr Asn Ser Cys Tyr Ser Ala Gly Val Phe His
        195                 200                 205

Leu His Gln Gly Asp Ile Ile Thr Val Lys Ile Pro Arg Ala Asn Ala
    210                 215                 220

Lys Leu Ser Leu Ser Pro His Gly Thr Phe Leu Gly Phe Val Lys Leu
225                 230                 235                 240

<210> SEQ ID NO 27
<211> LENGTH: 11
<212> TYPE: PRT
<213> ORGANISM: Artificial Sequence
<220> FEATURE:

-continued

```
<223> OTHER INFORMATION: Synthetic Construct
<220> FEATURE:
<223> OTHER INFORMATION: MBP-Ac1-11 (a synthetic NH2-terminal peptide
      of Myelin Basic Protein)

<400> SEQUENCE: 27

Ala Ser Gln Lys Arg Pro Ser Gln Arg Ser Lys
1               5                   10

<210> SEQ ID NO 28
<211> LENGTH: 34
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Formula I
<220> FEATURE:
<221> NAME/KEY: MISC_FEATURE
<222> LOCATION: (2)..(5)
<223> OTHER INFORMATION: Xaa is any amino acid except cysteine
<220> FEATURE:
<221> NAME/KEY: MISC_FEATURE
<222> LOCATION: (7)..(7)
<223> OTHER INFORMATION: Xaa is any amino acid except cysteine
<220> FEATURE:
<221> NAME/KEY: MISC_FEATURE
<222> LOCATION: (9)..(9)
<223> OTHER INFORMATION: Xaa is any amino acid except cysteine
<220> FEATURE:
<221> NAME/KEY: MISC_FEATURE
<222> LOCATION: (11)..(11)
<223> OTHER INFORMATION: Xaa is any amino acid residue except Ala
      and cysteine
<220> FEATURE:
<221> NAME/KEY: MISC_FEATURE
<222> LOCATION: (12)..(13)
<223> OTHER INFORMATION: Xaa is any amino acid except cysteine
<220> FEATURE:
<221> NAME/KEY: MISC_FEATURE
<222> LOCATION: (16)..(16)
<223> OTHER INFORMATION: Xaa is any amino acid except cysteine
<220> FEATURE:
<221> NAME/KEY: MISC_FEATURE
<222> LOCATION: (18)..(19)
<223> OTHER INFORMATION: Xaa is any amino acid except cysteine
<220> FEATURE:
<221> NAME/KEY: MISC_FEATURE
<222> LOCATION: (22)..(29)
<223> OTHER INFORMATION: Xaa is any amino acid except cysteine
<220> FEATURE:
<221> NAME/KEY: MISC_FEATURE
<222> LOCATION: (31)..(33)
<223> OTHER INFORMATION: Xaa is any amino acid except cysteine

<400> SEQUENCE: 28

Cys Xaa Xaa Xaa Xaa Tyr Xaa Asp Xaa Leu Xaa Xaa Xaa Cys Lys Xaa
1               5                   10                  15

Cys Xaa Xaa Arg Cys Xaa Xaa Xaa Xaa Xaa Xaa Xaa Cys Xaa Xaa
            20                  25                  30

Xaa Cys

<210> SEQ ID NO 29
<211> LENGTH: 64
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Z-domain of Staphylococcal protein A

<400> SEQUENCE: 29

Ala Gln His Asp Glu Ala Val Asp Asn Lys Phe Asn Lys Glu Gln Gln
```

```
                 1               5              10              15

Asn Ala Phe Tyr Glu Ile Leu His Leu Pro Asn Leu Asn Glu Gln
                    20              25              30

Arg Asn Ala Phe Ile Gln Ser Leu Lys Asp Asp Pro Ser Gln Ser Ala
                35              40              45

Asn Leu Leu Ala Glu Ala Lys Lys Leu Asn Asp Ala Gln Ala Pro Lys
            50              55              60

<210> SEQ ID NO 30
<211> LENGTH: 26
<212> TYPE: PRT
<213> ORGANISM: Artificial Sequence
<220> FEATURE:
<223> OTHER INFORMATION: Synthetic Construct
<220> FEATURE:
<223> OTHER INFORMATION: MiniBR3

<400> SEQUENCE: 30

Thr Pro Cys Val Pro Ala Glu Cys Phe Asp Leu Leu Val Arg His Cys
1               5                  10                  15

Val Ala Cys Gly Leu Leu Arg Thr Pro Arg
                20              25

<210> SEQ ID NO 31
<211> LENGTH: 296
<212> TYPE: PRT
<213> ORGANISM: Artificial Sequence
<220> FEATURE:
<223> OTHER INFORMATION: Synthetic Construct
<220> FEATURE:
<223> OTHER INFORMATION: BCMA-(I22K)-Fc fusion

<400> SEQUENCE: 31

Met Ser Ala Leu Leu Ile Leu Ala Leu Val Gly Ala Ala Val Ala Ser
1               5                  10                  15

Thr Ala Gly Gln Cys Ser Gln Asn Glu Tyr Phe Asp Ser Leu Leu His
                20              25              30

Ala Cys Lys Pro Cys Gln Leu Arg Cys Ser Ser Asn Thr Pro Pro Leu
            35              40              45

Thr Cys Gln Arg Tyr Cys Asn Ala Ser Val Thr Asn Ser Val Lys Gly
        50              55              60

Val Thr Asp Lys Ala Ala His Tyr Thr Leu Cys Pro Pro Cys Pro Ala
65              70              75              80

Pro Glu Leu Leu Gly Gly Pro Ser Val Phe Leu Phe Pro Pro Lys Pro
                85              90              95

Lys Asp Thr Leu Met Ile Ser Arg Thr Pro Glu Val Thr Cys Val Val
            100             105             110

Val Asp Val Ser His Glu Asp Pro Glu Val Lys Phe Asn Trp Tyr Val
        115             120             125

Asp Gly Val Glu Val His Asn Ala Lys Thr Lys Pro Arg Glu Glu Gln
            130             135             140

Tyr Asn Ser Thr Tyr Arg Val Val Ser Val Leu Thr Val Leu His Gln
145             150             155             160

Asp Trp Leu Asn Gly Lys Glu Tyr Lys Cys Lys Val Ser Asn Lys Ala
                165             170             175

Leu Pro Ala Pro Ile Glu Lys Thr Ile Ser Lys Ala Lys Gly Gln Pro
            180             185             190

Arg Glu Pro Gln Val Tyr Thr Leu Pro Pro Ser Arg Glu Glu Met Thr
        195             200             205
```

```
Lys Asn Gln Val Ser Leu Thr Cys Leu Val Lys Gly Phe Tyr Pro Ser
    210                 215                 220

Asp Ile Ala Val Glu Trp Glu Ser Asn Gly Gln Pro Glu Asn Asn Tyr
225                 230                 235                 240

Lys Thr Thr Pro Pro Val Leu Asp Ser Asp Gly Ser Phe Phe Leu Tyr
                245                 250                 255

Ser Lys Leu Thr Val Asp Lys Ser Arg Trp Gln Gln Gly Asn Val Phe
            260                 265                 270

Ser Cys Ser Val Met His Glu Ala Leu His Asn His Tyr Thr Gln Lys
        275                 280                 285

Ser Leu Ser Leu Ser Pro Gly Lys
    290                 295

<210> SEQ ID NO 32
<211> LENGTH: 14
<212> TYPE: PRT
<213> ORGANISM: Artificial Sequence
<220> FEATURE:
<223> OTHER INFORMATION: Synthetic Construct
<220> FEATURE:
<223> OTHER INFORMATION: peptide epitope

<400> SEQUENCE: 32

Met Ala Asp Pro Asn Arg Phe Arg Gly Lys Asp Leu Gly Gly
1               5                   10

<210> SEQ ID NO 33
<211> LENGTH: 34
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Formula II
<220> FEATURE:
<221> NAME/KEY: MISC_FEATURE
<222> LOCATION: (2)..(5)
<223> OTHER INFORMATION: Xaa is any amino acid except cysteine; and
      provided that the Formula II does not comprise the sequence
      CSQNEYFDSLLHACIPCQLRCSSNTPPLTCQRYC
<220> FEATURE:
<221> NAME/KEY: MISC_FEATURE
<222> LOCATION: (6)..(6)
<223> OTHER INFORMATION: Xaa is selected from the group consisting of
      Tyr, Ala, Asp, Ser and Phe
<220> FEATURE:
<221> NAME/KEY: MISC_FEATURE
<222> LOCATION: (7)..(7)
<223> OTHER INFORMATION: Xaa is any amino acid except cysteine; and
      provided that the Formula II does not comprise the sequence
      CSQNEYFDSLLHACIPCQLRCSSNTPPLTCQRYC
<220> FEATURE:
<221> NAME/KEY: MISC_FEATURE
<222> LOCATION: (9)..(9)
<223> OTHER INFORMATION: Xaa is any amino acid except cysteine; and
      provided that the Formula II does not comprise the sequence
      CSQNEYFDSLLHACIPCQLRCSSNTPPLTCQRYC
<220> FEATURE:
<221> NAME/KEY: MISC_FEATURE
<222> LOCATION: (11)..(11)
<223> OTHER INFORMATION: Xaa is any amino acid residue except Ala
<220> FEATURE:
<221> NAME/KEY: MISC_FEATURE
<222> LOCATION: (12)..(13)
<223> OTHER INFORMATION: Xaa is any amino acid except cysteine; and
      provided that the Formula II does not comprise the sequence
      CSQNEYFDSLLHACIPCQLRCSSNTPPLTCQRYC
<220> FEATURE:
<221> NAME/KEY: MISC_FEATURE
<222> LOCATION: (15)..(15)
<223> OTHER INFORMATION: Xaa is any amino acid residue except Ala or Lys
<220> FEATURE:
```

```
<221> NAME/KEY: MISC_FEATURE
<222> LOCATION: (16)..(16)
<223> OTHER INFORMATION: Xaa is any amino acid except cysteine; and
      provided that the Formula II does not comprise the sequence
      CSQNEYFDSLLHACIPCQLRCSSNTPPLTCQRYC
<220> FEATURE:
<221> NAME/KEY: MISC_FEATURE
<222> LOCATION: (18)..(18)
<223> OTHER INFORMATION: Xaa is Asp
<220> FEATURE:
<221> NAME/KEY: MISC_FEATURE
<222> LOCATION: (19)..(19)
<223> OTHER INFORMATION: Xaa is any amino acid except cysteine; and
      provided that the Formula II does not comprise the sequence
      CSQNEYFDSLLHACIPCQLRCSSNTPPLTCQRYC
<220> FEATURE:
<221> NAME/KEY: MISC_FEATURE
<222> LOCATION: (20)..(20)
<223> OTHER INFORMATION: Xaa is Tyr
<220> FEATURE:
<221> NAME/KEY: MISC_FEATURE
<222> LOCATION: (22)..(29)
<223> OTHER INFORMATION: Xaa is any amino acid except cysteine; and
      provided that the Formula II does not comprise the sequence
      CSQNEYFDSLLHACIPCQLRCSSNTPPLTCQRYC
<220> FEATURE:
<221> NAME/KEY: MISC_FEATURE
<222> LOCATION: (31)..(33)
<223> OTHER INFORMATION: Xaa is any amino acid except cysteine; and
      provided that the Formula II does not comprise the sequence
      CSQNEYFDSLLHACIPCQLRCSSNTPPLTCQRYC

<400> SEQUENCE: 33

Cys Xaa Xaa Xaa Xaa Xaa Xaa Asp Xaa Leu Xaa Xaa Xaa Cys Xaa Xaa
1               5                   10                  15

Cys Xaa Xaa Xaa Cys Xaa Xaa Xaa Xaa Xaa Xaa Xaa Xaa Cys Xaa Xaa
            20                  25                  30

Xaa Cys

<210> SEQ ID NO 34
<211> LENGTH: 34
<212> TYPE: PRT
<213> ORGANISM: Artificial Sequence
<220> FEATURE:
<223> OTHER INFORMATION: Synthetic Construct
<220> FEATURE:
<223> OTHER INFORMATION: Formula II
<220> FEATURE:
<221> NAME/KEY: MISC_FEATURE
<222> LOCATION: (11)..(11)
<223> OTHER INFORMATION: Xaa is Leu, Ile, or Val
<220> FEATURE:
<221> NAME/KEY: MISC_FEATURE
<222> LOCATION: (15)..(15)
<223> OTHER INFORMATION: Xaa is Ile, Ala, or Lys
<220> FEATURE:
<221> NAME/KEY: MISC_FEATURE
<222> LOCATION: (18)..(18)
<223> OTHER INFORMATION: Xaa is Gln or Asp
<220> FEATURE:
<221> NAME/KEY: MISC_FEATURE
<222> LOCATION: (20)..(20)
<223> OTHER INFORMATION: Xaa is Arg or Tyr

<400> SEQUENCE: 34

Cys Ser Gln Asn Glu Tyr Phe Asp Ser Leu Xaa His Ala Cys Xaa Pro
1               5                   10                  15

Cys Xaa Leu Xaa Cys Ser Ser Asn Thr Pro Pro Leu Thr Cys Gln Arg
            20                  25                  30

Tyr Cys

<210> SEQ ID NO 35
```

```
<211> LENGTH: 34
<212> TYPE: PRT
<213> ORGANISM: Homo Sapiens
<220> FEATURE:
<223> OTHER INFORMATION: BCMA 8-41

<400> SEQUENCE: 35

Cys Ser Gln Asn Glu Tyr Phe Asp Ser Leu Leu His Ala Cys Ile Pro
1               5                   10                  15

Cys Gln Leu Arg Cys Ser Ser Asn Thr Pro Pro Leu Thr Cys Gln Arg
            20                  25                  30

Tyr Cys
```